(12) United States Patent
Durocher et al.

(10) Patent No.: US 10,808,017 B2
(45) Date of Patent: Oct. 20, 2020

(54) UBIQUITIN VARIANTS AND USES THEROF AS 53BP1 INHIBITORS

(71) Applicants: The Governing Council of the University of Toronto, Toronto (CA); Sinai Health System, Toronto (CA)

(72) Inventors: Daniel Durocher, Toronto (CA); Sachdev Sidhu, Toronto (CA); Wei Zhang, Mississauga (CA); Frank Sicheri, Toronto (CA); Marella Canny, Lubbock, TX (US)

(73) Assignees: The Governing Council of the University of Toronto, Toronto (CA); Sinai Health System, Toronto (CA)

( * ) Notice: Subject to any disclaimer, the term of this patent is extended or adjusted under 35 U.S.C. 154(b) by 0 days.

(21) Appl. No.: 16/073,501

(22) PCT Filed: Jan. 31, 2017

(86) PCT No.: PCT/CA2017/000020
§ 371 (c)(1),
(2) Date: Jul. 27, 2018

(87) PCT Pub. No.: WO2017/132746
PCT Pub. Date: Aug. 10, 2017

(65) Prior Publication Data
US 2019/0010196 A1   Jan. 10, 2019

Related U.S. Application Data

(60) Provisional application No. 62/289,627, filed on Feb. 1, 2016.

(51) Int. Cl.
| | | |
|---|---|---|
| *C07K 14/47* | (2006.01) | |
| *C12N 15/00* | (2006.01) | |
| *C12N 9/22* | (2006.01) | |
| *C12N 15/113* | (2010.01) | |
| *C12N 15/62* | (2006.01) | |
| *A61K 38/00* | (2006.01) | |

(52) U.S. Cl.
CPC ............. *C07K 14/47* (2013.01); *C12N 9/22* (2013.01); *C12N 15/00* (2013.01); *C12N 15/113* (2013.01); *C12N 15/62* (2013.01); *A61K 38/00* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2006/0115839 A1 | 6/2006 | Halazonetis | |
| 2013/0225436 A1* | 8/2013 | Sidhu | C07K 14/47 |
| | | | 506/9 |

FOREIGN PATENT DOCUMENTS

| | | |
|---|---|---|
| GB | 2419954 A | 10/2006 |
| WO | WO 2003/072557 | 9/2003 |

OTHER PUBLICATIONS

Fradet-Turcotte et al., "53BP1 is a reader of the DNA-damage-induced H2A Lys 15 ubiquitin mark", Nature, vol. 499(7456):50-4, Jul. 2013.
Jackson et al., "Regulation of DNA damage responses by ubiquitin and SUMO", Cell, vol. 49(5):795-807, Mar. 2013.
Orthwein et al., "A mechanism for the suppression of homologous recombination in G1 cells", Nature, vol. 528(7582):422-6, Dec. 2015.
Wan et al., "Crystal structure of a 53P1 tudor domain in complex with a ubiquitin 2 variant", Protein Database, Accession No. 5J26, Mar. 2016.
International Search Report and Written Opinion issued on corresponding International Patent Application No. PCT/CA2017/00020, dated May 1, 2017.
Bennardo N, et al. Alternative-NHEJ is a mechanistically distinct pathway of mammalian chromosome break repair. PLoS Genet. Jun. 27, 2008;4(6):e1000110.
Botuyan MV, et al. Structural basis for the methylation state-specific recognition of histone H4-K20 by 53BP1 and Crb2 in DNA repair. Cell. Dec. 29, 2006;127(7):1361-73.
Buchberger A, et al. The UBX domain: a widespread ubiquitin-like module. J Mol Biol. Mar. 16, 2001;307(1):17-24.
Burt A. Site-specific selfish genes as tools for the control and genetic engineering of natural populations. Proc Biol Sci. May 7, 2003;270(1518):921-8.
Canny et al., A genetically encoded inhibitor of 53P1 to stimulate homology-based gene editing, bioRxiv 060954; doi: https://doi.org/10.1101/060954; Jun. 2016.
Chandrasegaran S & Carroll D. Origins of Programmable Nucleases for Genome Engineering. J Mol Biol. Feb. 27, 2016;428(5 Pt B):963-89.
Chapman Jr, et al. Playing the end game: DNA double-strand break repair pathway choice. Mol Cell. Aug. 24, 2012;47(4):497-510.
Chistiakov DA, et al. Ligase IV syndrome. European journal of medical genetics. Adv Exp Med Biol. 2010;685:175-85.
Chu VT, et al. Increasing the efficiency of homology-directed repair for CRISPR-Cas9-induced precise gene editing in mammalian cells. Nat Biotechnol. May 2015;33(5):543-8.
Cox DB, et al. Therapeutic genome editing: prospects and challenges. Nat Med. Feb. 2015;21(2):121-31.

(Continued)

*Primary Examiner* — Christina Bradley
(74) *Attorney, Agent, or Firm* — Howson & Howson LLP

(57) ABSTRACT

53BP1 inhibitors, compositions comprising the inhibitors and methods of using same are provided. The inhibitors can be used in combination with gene editing systems.

24 Claims, 16 Drawing Sheets
Specification includes a Sequence Listing.

(56) References Cited

OTHER PUBLICATIONS

Database GNPD, Accession No. 5J26: Crystal Structure of a 53bp1 Tudor Domain in Complex with a Ubiquitin Variant, Dec. 2016.
Dikic I, et al. Ubiquitin-binding domains—from structures to functions. Nat Rev Mol Cell Biol. Oct. 2009;10(10):659-71.
Doudna JA & Charpentier E. Genome editing. The new frontier of genome engineering with CRISPR-Cas9. Science. Nov. 28, 2014;346(6213):1258096.
Ernst A, et al. A strategy for modulation of enzymes in the ubiquitin system. Science. Feb. 1, 2013;339(6119):590-5.
Escribano-Díaz C, et al. A Cell Cycle-Dependent Regulatory Circuit Composed of 53BP1-RIF1 and BRCA1-CtIP Controls DNA Repair Pathway Choice. Mol Cell. Mar. 7, 2013;49(5):872-83.
Feng L, et al. RIF1 counteracts BRCA1-mediated end resection during DNA repair. J Biol Chem. Apr. 19, 2013;288(16):11135-43.
Gaëlle C, et al. The Tudor Tandem of 53BP1: A New Structural Motif Involved in DNA and RG-Rich Peptide Binding. Structure. Sep. 2004;12(9):1551-62.
Gunn A & Stark JM. I-SceI-Based Assays to Examine Distinct Repair Outcomes of Mammalian Chromosomal Double Strand Breaks. Methods Mol Biol. 2012;920:379-91.
Hart T, et al. High-Resolution CRISPR Screens Reveal Fitness Genes and Genotype-Specific Cancer Liabilities. Cell. Dec. 3, 2015;163(6):1515-26.
Leahy JJ, et al. Identification of a highly potent and selective DNA-dependent protein kinase (DNA-PK) inhibitor (NU7441) by screening of chromenone libraries. Bioorg Med Chem Lett. Dec. 20, 2004;14(24):6083-7.
Lieber MR. The mechanism of double-strand DNA break repair by the nonhomologous DNA end-joining pathway. Annu Rev Biochem. 2010;79:181-211.
Maruyama T, et al. Increasing the efficiency of precise genome editing with CRISPR-Cas9 by inhibition of nonhomologous end joining.
Moynahan ME, et al. Brca1 controls homology-directed DNA repair. Mol Cell. Oct. 1999;4(4):511-8.
Munck JM, et al. Chemosensitization of cancer cells by KU-0060648, a dual inhibitor of DNA-PK and PI-3K. Mol Cancer Ther. Aug. 2012;11(8):1789-98.
Nijnik A, et al. DNA repair is limiting for haematopoietic stem cells during ageing. Nature. Jun. 7, 2007;447(7145):686-90.
O'Donnell L, et al. The MMS22L-TONSL complex mediates recovery from replication stress and homologous recombination. Mol Cell. Nov. 24, 2010;40(4):619-31.
Panier S & Boulton SJ.Double-strand break repair: 53BP1 comes into focus. Nat Rev Mol Cell Biol. Jan. 2014;15(1):7-18.
Pinder J, et al. Nuclear domain 'knock-in' screen for the evaluation and identification of small molecule enhancers of CRISPR-based genome editing. Nucleic Acids Res. Oct. 30, 2015;43(19):9379-92.
San Filippo J, et al. Mechanism of eukaryotic homologous recombination. Annu Rev Biochem. 2008;77:229-57.
Sanjana NE et al. Improved vectors and genome-wide libraries for CRISPR screening. Nat Methods. Aug. 2014;11(8):783-784.
Sfeir A & Symington LS. Microhomology-Mediated End Joining: A Back-up Survival Mechanism or Dedicated Pathway? Trends Biochem Sci. Nov. 2015;40(11):701-714.
Srivastava M et al. An inhibitor of nonhomologous end-joining abrogates double-strand break repair and impedes cancer progression. Cell. Dec. 21, 2012;151(7):1474-87.
Symington LS & Gautier J. Double-strand break end resection and repair pathway choice. Annu Rev Genet. 2011;45:247-71.
Tonikian R, et al. Identifying specificity profiles for peptide recognition modules from phage-displayed peptide libraries. Nat Protoc. 2007;2(6):1368-86.
Vijay-Kumar S, et al. Structure of ubiquitin refined at 1.8 A resolution. J Mol Biol. Apr. 5, 1987;194(3):531-44.
Willmore E, et al. A novel DNA-dependent protein kinase inhibitor, NU7026, potentiates the cytotoxicity of topoisomerase II poisons used in the treatment of leukemia. Blood. Jun. 15, 2004;103(12):4659-65.
Xie A, et al. Distinct roles of chromatin-associated proteins MDC1 and 53BP1 in mammalian double-strand break repair. Mol Cell. Dec. 28, 2007;28(6):1045-57.
Xia et al., Negative Cell Cycle Regulation and DNA Damage-inducible Phosphorylation of the BRCT Protein 53BP2, The Journal of Biological Chemistry, 276(4):2708-2718, Jan. 2001.
Search Report issued in European Patent Application No. 17746656.2, dated Jun. 4, 2019.
Applicant's Response filed Jan. 14, 2020 in European Patent Application No. 17746656.2.

\* cited by examiner

FIG 1A
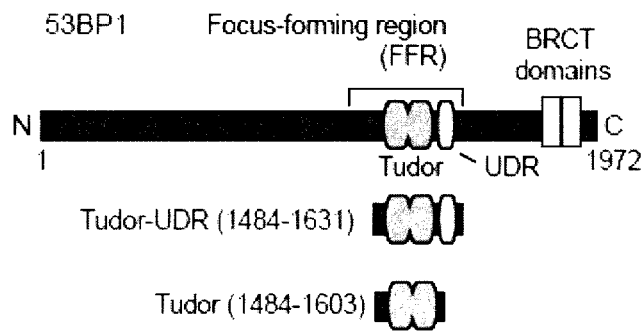
FIG 1B
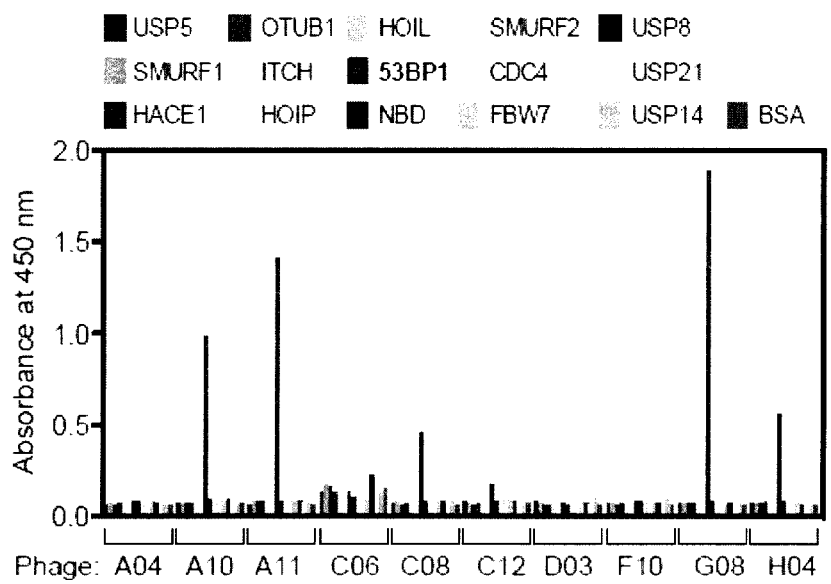
FIG 1C

FIG 5A
53BP1 Tudor domain bound to H4K20me2 peptide
FIG 5B
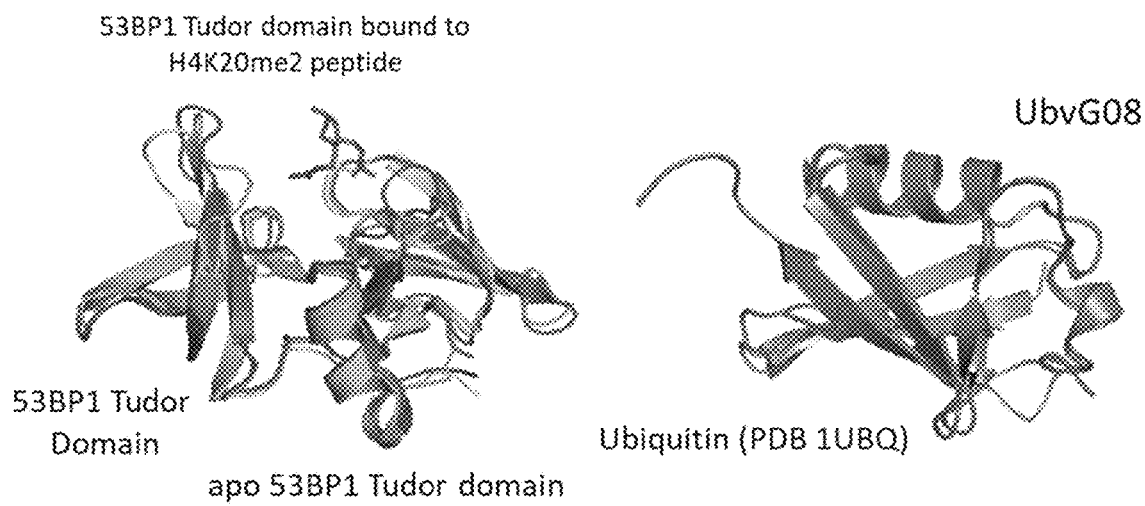
53BP1 Tudor Domain
apo 53BP1 Tudor domain
UbvG08
Ubiquitin (PDB 1UBQ)
FIG 5C
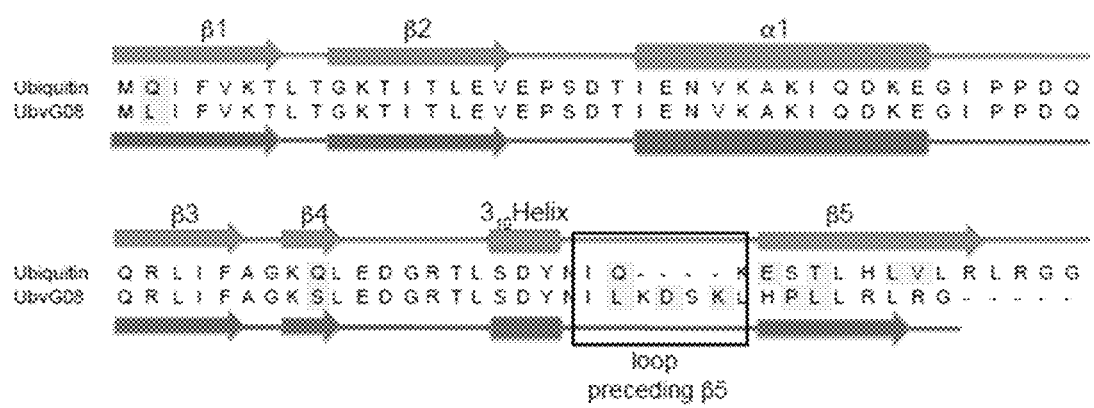
loop preceding β5
FIG 5D                                    FIG 5E
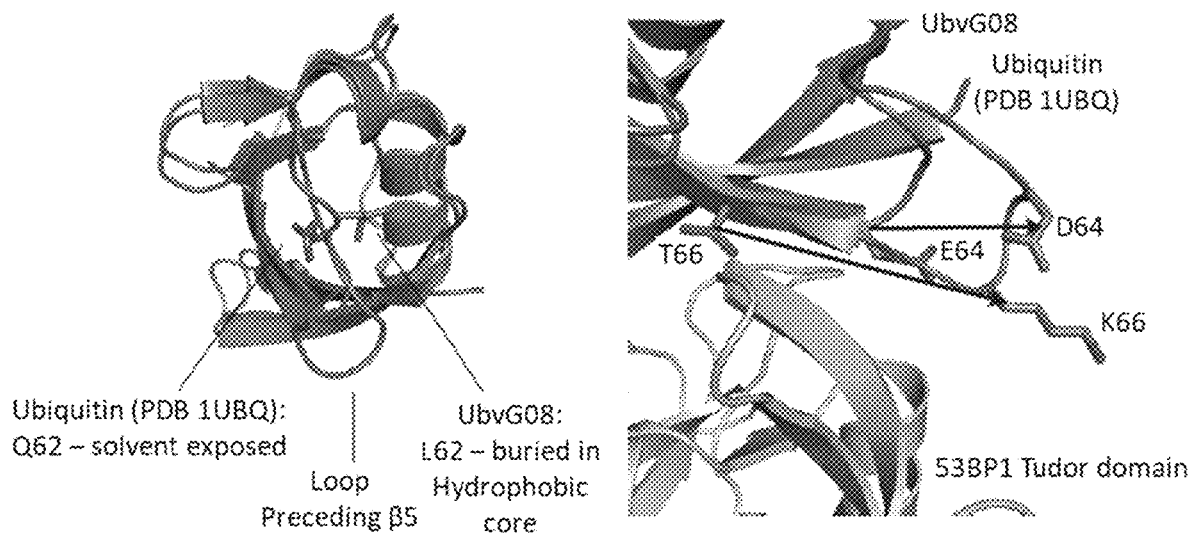
Ubiquitin (PDB 1UBQ): Q62 – solvent exposed
UbvG08: L62 – buried in Hydrophobic core
Loop Preceding β5
UbvG08
Ubiquitin (PDB 1UBQ)
T66  E64  D64
K66
53BP1 Tudor domain

U2OS DR-GFP

U2OS EJ2-GFP

FIG 11A
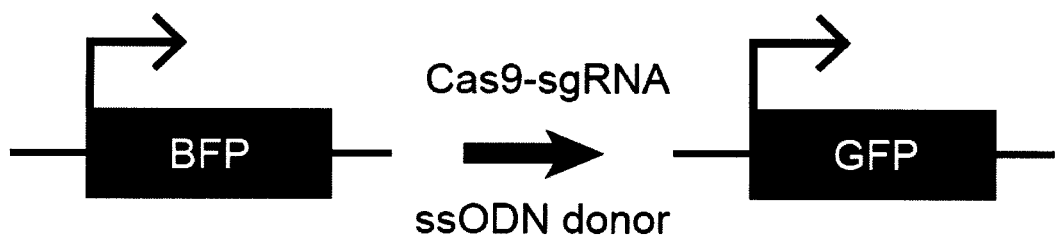
FIG 11B
Optimal ssODN donor
FIG 11C
Suboptimal ssODN donor
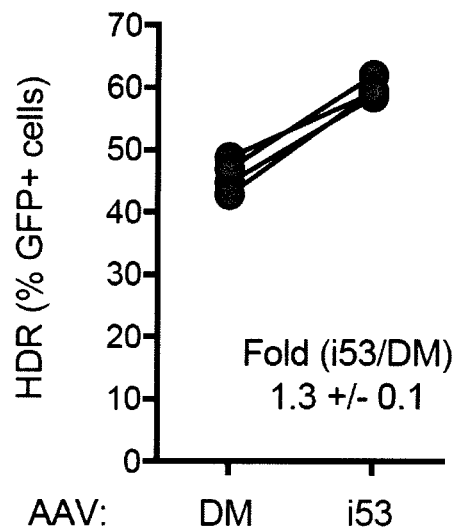
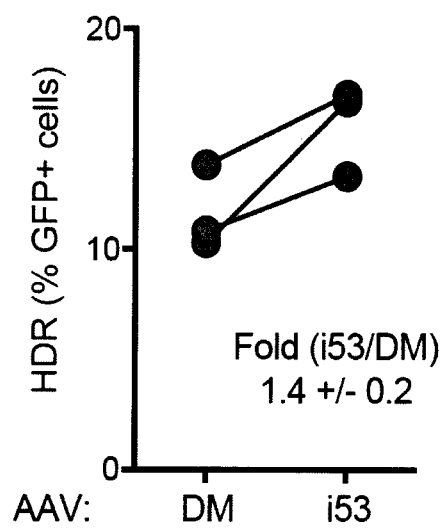

UBIQUITIN VARIANTS AND USES THEROF AS 53BP1 INHIBITORS

CROSS-REFERENCE TO RELATED APPLICATIONS

This is a National Stage Entry under 35 U.S.C. 371 of International Patent Application No. PCT/CA2017/000020, filed Jan. 31, 2017, which claims priority to U.S. Provisional Patent Application No. 62/289,627, filed Feb. 1, 2016. These applications are incorporated by reference herein.

Applicant hereby incorporates by reference the Sequence Listing material filed in electronic form herewith. This file is labeled "MTS59PCT_Seq_Listing_ST25.txt".

TECHNICAL FIELD

The present application relates to 53BP1 inhibitors, compositions comprising the inhibitors and methods of using the inhibitors.

BACKGROUND

The dominant pathway that mends two-ended DNA double-strand breaks (DSBs), such as those created by programmable nucleases, is non-homologous end-joining (NHEJ). NHEJ limits homologous recombination (HR; also known as HDR for homology-directed repair) first by being a fast-acting repair pathway that seals broken ends through a DNA ligase IV-dependent reaction [8]. Secondly, in NHEJ the Ku70/Ku80 heterodimer binds to DNA ends with high affinity to block their processing by the nucleases that generate the single-stranded DNA (ssDNA) tails that are necessary for the initiation of HR [8, 9]. A chromatin-based ubiquitin (Ub)-dependent signaling cascade [10] is also initiated by the detection of DSBs that modulates DSB repair pathway "choice" [11]. This pathway is largely controlled by an antagonism between p53-binding protein 1 (53BP1), a pro-NHEJ factor, and BRCA1, the well-known breast and ovarian tumor suppressor and HR factor [11]. 53BP1 limits HR in part by blocking long-range DNA end resection but also by inhibiting BRCA1 recruitment to DSB sites [6, 12]. 53BP1 promotes NHEJ over HR by suppressing formation of 3' single-stranded DNA tails, which is the rate-limiting step in the initiation of HR. Since loss of 53BP1 results in increased HR levels [15], it is desirable to identify inhibitors of 53BP1 that selectively stimulate homology-directed repair and can be used in gene editing reactions where the engagement of the HR pathway is required.

SUMMARY

The present disclosure relates to inhibitors of 53BP1 which bind and occlude the tandem Tudor domain of 53BP1 [32], blocking its ability to accumulate at sites of DNA damage. The inhibitors enhance gene targeting and chromosomal gene conversion, two HR reactions. The inhibitors can also activate HR in G1 cells when combined with the activation of end-resection and KEAP1 inhibition. The inhibitors also stimulate homology-directed repair with single-stranded oligonucleotides (ssODNs). 53BP1 inhibition may be used as a tool to enhance precise genome editing by canonical HR pathways.

In an aspect, the disclosure relates to a polypeptide comprising Met Gln Ile Phe Val Lys Thr Leu Thr Gly Lys Thr Ile Thr Leu Glu Val Glu Pro Ser Asp Thr Ile Glu Asn Val Lys Ala Lys Ile Gln Asp Lys Glu Gly Ile Pro Pro Asp Gln Gln Arg Leu Ile Phe Ala Gly Lys Gln Leu Glu Asp Gly Arg Thr Leu Ser Asp Tyr Asn Ile Gln Lys Glu Ser Thr Leu His Leu Val Leu Arg Leu Arg Gly Gly [FIG. 1c Ub WT; hereinafter referred to as SEQ ID NO: 1] with modifications at selected amino acids, in particular modifications at more than 1, 2, 3, 4, 5, 6, 7, 8, 9, 10, 11, 12, 13, 14, 15, 16, 17, 18, 19 or 20 amino acids.

In an aspect, a polypeptide disclosed herein exhibits binding affinity to 53BP1 tandem Tudor domain. In an aspect, a polypeptide disclosed herein binds to 53BP1 tandem Tudor domain.

In an aspect, the disclosure relates to a 53BP1 binding polypeptide comprising three, four, five, six, seven or more amino acid modifications compared to a wild-type ubiquitin polypeptide (SEQ ID NO:1) wherein said polypeptide inhibits 53BP1 activity. In an aspect, herein the polypeptide selectively inhibits 53BP1.

In an aspect, the disclosure relates to a polypeptide comprising: a) an amino acid sequence having at least one amino acid modification at an amino acid position corresponding to a position of SEQ ID NO: 1 selected from the group consisting of positions 2, 4, 6, 8, 10, 11, 12, 14, 44, 46, 47, 48, 49, 62, 63, 64, 66, 68, 69, 70, 71, 72, 73, 74, 75, and 76, and combinations thereof; or, b) an amino acid sequence having at least 1, 2, 3, 4, 5, 6, 7, 8, 9, 10, 11, 12, 13, 14, 15, 16, 17, 18, 19 or 20, of any of the amino acid modifications of (a).

In an aspect, the modifications comprise amino acid replacements at the position corresponding to position 2. In an aspect, the modifications comprise amino acid replacements at positions corresponding to positions 2 and 66. In an aspect, the modifications comprise amino acid replacements at positions corresponding to positions 2 and 49. In an aspect, the modifications comprise amino acid replacements at positions corresponding to positions 2, 49 and 66. In an aspect, the modifications comprise amino acid replacements at positions corresponding to positions 2, 62, 64, 66, 69 and 70. In an aspect, the modifications comprise amino acid replacements at positions corresponding to positions 2, 62, 64, 66, 69, 70 and 75. In an aspect, the modifications comprise amino acid replacements at positions corresponding to positions 2, 62, 64, 66, 69, 70, 75 and 76. In an aspect, the modifications comprise amino acid replacements at positions corresponding to positions 2, 49, 62, 64, 66, 69 and 70. In an aspect, the modifications comprise amino acid replacements at positions corresponding to positions 2, 44, 49, 62, 64, 66, 69 and 70.

In an aspect, the modifications comprise amino acid replacements at positions corresponding to positions 8, 9, 10, 12, and 47. In an aspect, the modifications comprise amino acid replacements at positions corresponding to positions 8, 9, 68 and 72. In an aspect, the modifications comprise amino acid replacements at positions corresponding to positions 8, 9, 10, 47, 48 and 68. In an aspect, the modifications comprise amino acid replacements at positions corresponding to positions 8, 9, 10, 12, 47, 49, 62 and 72. In an aspect, the modifications comprise amino acid replacements at positions corresponding to positions 4, 8, 9, 10, 12, 47, 48, 49, 62, 63, 64, 68, 72, 73, 74, 75 and 76.

In an aspect, the modifications comprise amino acid replacements at positions corresponding to positions 2, 8, 9, 47, 49, 66 and 72. In an aspect, the modifications comprise amino acid replacements at positions corresponding to positions 2, 8, 9, 47, 49, 66, 68 and 72. In an aspect, the modifications comprise amino acid replacements at positions corresponding to positions 6, 8, 9, 46, 66, 68 and 72.

In an aspect, the modifications comprise amino acid replacements at positions corresponding to positions 6, 8, 9, 11, 14, 46, 47, 49, 66 and 68. In an aspect, the modifications comprise amino acid replacements at positions corresponding to positions 6, 8, 9, 11, 14, 46, 47, 49, 66, 68 and 72. In an aspect, the modifications comprise amino acid replacements at positions corresponding to positions 2, 6, 8, 9, 11, 14, 46, 47, 49, 66, 68 and 72.

In an aspect, the modifications comprise amino acid replacements at positions corresponding to positions 2, 8, 9, 47, 49 and 72. In an aspect, the modifications comprise amino acid replacements at positions corresponding to positions 2, 8, 9, 10, 12, 47, 49 and 72. In an aspect, the modifications comprise amino acid replacements at positions corresponding to positions 6, 8, 9, 10, 11, 12, 14, 46, 47, 49, 68 and 72. In an aspect, the modifications comprise amino acid replacements at positions corresponding to positions 6, 8, 9, 10, 11, 12, 14, 46, 47, 49, 66, 68 and 72. In an aspect, the modifications comprise amino acid replacements at positions corresponding to positions 6, 8, 9, 10, 11, 12, 14, 46, 47, 49, 64, 66, 68 and 72.

In an aspect, the modifications comprise amino acid replacements at positions corresponding to positions 2, 8, 9, 10, 12 and 47. In an aspect, the modifications comprise amino acid replacements at positions corresponding to positions 2, 4, 8, 9, 10, 12, 47, 48, 68, 71, 74 and 75. In an aspect, the modifications comprise amino acid replacements at positions corresponding to positions 2, 4, 8, 9, 10, 12, 47, 48, 68, 71, 74 and 75. n an aspect, the modifications comprise amino acid replacements at positions corresponding to positions 2, 4, 8, 9, 10, 12, 47, 48, 68, 71, 74, 75 and 76. In an aspect, the modifications comprise amino acid replacements at positions corresponding to positions 2, 4, 8, 9, 10, 12, 44, 47, 48, 68, 71, 74, 75 and 76.

In an aspect, the disclosure provides a polypeptide comprising a ubiquitin-like folding motif that has a binding affinity to 53BP1 tandem Tudor domain comprising modifications at Leu8, Thr9, Gly47, Lys48, and His68 of SEQ ID NO: 1, or a solvate or salt thereof.

In an aspect, the disclosure provides a polypeptide comprising a ubiquitin-like folding motif that has a binding affinity to 53BP1 tandem Tudor domain comprising modifications at Leu8, Thr9, His68, and Arg72 of SEQ ID NO: 1, or a solvate or salt thereof.

In an aspect, the disclosure provides a polypeptide comprising a ubiquitin-like folding motif that has a binding affinity to 53BP1 tandem Tudor domain comprising modifications at Lys6, Leu8, Thr9, Ala46, Thr66, His68 and Arg72 of SEQ ID NO: 1, or a solvate or salt thereof.

In an aspect, the disclosure provides a polypeptide comprising a ubiquitin-like folding motif that has a binding affinity to 53BP1 tandem Tudor domain comprising modifications at Gln2, Gln49 and Thr66 of SEQ ID NO: 1, or a solvate or salt thereof.

In an aspect, the disclosure provides a polypeptide comprising a ubiquitin-like folding motif that has a binding affinity to 53BP1 tandem Tudor domain comprising modifications at Gln2, Phe4, Lys6, Leu8, Thr9, Gly10, Ala46, Gly47, Lys48, Gln62, Thr66, His68, Arg72, and Gly75 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln62, Glu64, Thr66, Leu69 and Val70 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln49, Gln62, Glu64, Thr66, Leu69 and Val70 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln62, Glu64, Thr66, Leu69, Val70 and Gly75 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln62, Glu64, Thr66, Leu69, Val70 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln49, Gln62, Glu64, Thr66, Leu69, Val70 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln62, Glu64, Thr66, Leu69, Val70, Gly75 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Gln49, Gln62, Glu64, Thr66, Leu69, Val70, Gly75 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Lys6, Leu8, Thr9, Lys 11, Thr14, Ala46, Gly47, Gln49, Thr66 and His68 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Lys6, Leu8, Thr9, Gly10, Lys11, Thr12, Thr14, Ala46, Gly47, Gln49, Glu64, Thr66, His68 and Arg72 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Lys6, Leu8, Thr9, Lys11, Thr14, Ala46, Gly47, Gln49, Thr66, His68 and Arg72 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Phe4, Leu8, Thr9, Gly10, Thr12, Gly47, Lys48, Gln49, Gln62, Lys63, Glu64, His68, Arg72, Leu73, Arg74, Gly75, and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Lys6, Leu8, Thr9, Lys11, Thr14, Ala46, Gly47, Gln49, Thr66, His68 and Arg72 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Lys6, Leu8, Thr9, Gly10, Lys11, Thr12, Thr14, Ala46, Gly47, Gln49, Thr66, His68 and Arg72 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Phe4, Leu8, Thr9, Gly10, Thr12, Gly47, Lys48, His68, Leu71, Arg74 and Gly75 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Phe4, Leu8, Thr9, Gly10, Thr12, Gly47, Lys48, His68, Leu71, Arg74, Gly75 and Gly76 of SEQ ID NO: 1, or a solvate or salt thereof.

In an aspect, a polypeptide disclosed herein has a quantifiable binding affinity to the 53BP1 Tudor domain of 0.5 to $15 \times 10^{-9}$ M, 0.5 to $25 \times 10^{-9}$ M, 0.5 to $50 \times 10^{-9}$ M, 0.5 to $100 \times 10^{-9}$ M, 0.5 to $200 \times 10^{-9}$ M, 1 to $200 \times 10^{-9}$ M, 1 to $300 \times 10^{-9}$ M, 1 to $400 \times 10^{-9}$ M, 1 to $500 \times 10^{-9}$ M, 100 to $300 \times 10^{-9}$ M, 100 to $250 \times 10$ M, or 200 to $250 \times 10^{-9}$ M.

In an aspect, a modified polypeptide disclosed herein has at least 60%, 70%, 80%, 90%, 95% or 99% identity in its amino acid sequence to SEQ ID NO: 1.

In an aspect, a polypeptide disclosed herein is additionally modified at Ile44.

In an aspect, the disclosure provides a modified ubiquitin polypeptide comprising a ubiquitin-like folding motif that has a binding affinity to 53BP1 tandem Tudor domain comprising modifications at Gln2, Ile44, Gln62, Glu64, Thr66, Leu69 and Val70 of SEQ ID NO: 1, or a solvate or salt thereof In an aspect, the disclosure provides a modified ubiquitin polypeptide comprising a ubiquitin-like folding motif that has a binding affinity to 53BP1 tandem Tudor domain comprising modifications at Gln2, Ile44, Gln49, Gln62, Glu64, Thr66, Leu69 and Val70 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Ile44, Gln62, Glu64, Thr66, Leu69, Val70, and Gly75 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Ile44, Gln62, Glu64, Thr66, Leu69, Val70, and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Ile44, Gln49, Gln62, Glu64, Thr66, Leu69, Val70 and Gly75 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Ile44, Gln49, Gln62, Glu64, Thr66, Leu69, Val70 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Ile44, Gln62, Glu64, Thr66, Leu69, Val70, Gly75 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Ile44, Gln49, Gln62, Glu64, Thr66, Leu69, Val70, Gly75 and Gly76 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Phe4, Leu8, Thr9, Gly10, Thr12, Ile44, Gly47, Lys48, His68, Leu71, Arg74 and Gly75 of SEQ ID NO: 1, or a solvate or salt thereof.

In an aspect, the disclosure provides a modified ubiquitin polypeptide comprising a ubiquitin-like folding motif that has a binding affinity to 53BP1 tandem Tudor domain comprising modifications at Gln2, Phe4, Leu8, Thr9, Gly10, Thr12, Ile44, Gly47, Lys48, His68, Leu71, Arg74, Gly75 and Gly76 of SEQ ID NO: 1, or a solvate or salt thereof.

In an aspect, the disclosure provides a polypeptide comprising the amino acid sequence Met $Xaa_2$ Ile $Xaa_4$ Val $Xaa_6$ Thr $Xaa_8$ $Xaa_9$ $Xaa_{10}$ $Xaa_{11}$ $Xaa_{12}$ Ile $Xaa_{14}$ Leu Glu Val Glu Pro Ser Asp Thr Ile Glu Asn Val Lys Ala Lys Ile Gln Asp Lys Glu Gly Ile Pro Pro Asp Gln Gln Arg Leu $Xaa_{44}$ Phe $Xaa_{46}$ $Xaa_{47}$ $Xaa_{48}$ $Xaa_{49}$ Leu Glu Asp Gly Arg Thr Leu Ser Asp Tyr Asn Ile $Xaa_{62}$ $Xaa_{63}$ $Xaa_{64}$ Ser $Xaa_{66}$ $Xaa_{67}$ $Xaa_{68}$ $Xaa_{69}$ $Xaa_{70}$ $Xaa_{71}$ $Xaa_{72}$ $Xaa_{73}$ $Xaa_{74}$ $Xaa_{75}$ $Xaa_{76}$, wherein $Xaa_2$ is Gln, Leu, or Arg, $Xaa_4$ is Phe, Tyr or Ile, $Xaa_6$ is Lys or Thr, $Xaa_8$ is Leu, Phe or Asp, $Xaa_9$ is Thr, Ala or Met, $Xaa_{10}$ is Gly, Arg or Trp, $Xaa_{11}$ is Lys or Met, $Xaa_{12}$ is Thr, Pro or Arg, $Xaa_{14}$ is Thr or Ser, $Xaa_{44}$ is Ile, Ala or Tyr, $Xaa_{46}$ is Ala or Gly, $Xaa_{47}$ is Gly, Glu, Asp or Ala, $Xaa_{48}$ is Lys, Met or Ser, $Xaa_{49}$ is Gln, Arg, Asp or Ser, $Xaa_{62}$ is Gln, Lys, or Leu, $Xaa_{63}$ is Lys or Asn, $Xaa_{64}$ is Glu or Asp, $Xaa_{66}$ is Thr, Ser or Lys, $Xaa_{67}$ is Leu or Lys, $Xaa_{68}$ is His, Phe, Asn, or Leu, $Xaa_{69}$ is Leu or Pro, $Xaa_{70}$ is Val or Leu, $Xaa_{71}$ is Leu or Val, $Xaa_{72}$ is Arg, Lys or Asn, $Xaa_{73}$ is Leu or Asn, $Xaa_{74}$ is Arg, Ser or Leu, $Xaa_{75}$ is Gly, Val or Arg or is absent, $Xaa_{76}$ is Gly, Thr or Val or is absent [SEQ ID NO: 48], wherein one or more amino acid(s) designated Xaa is an amino acid different from the amino acid sequence of SEQ ID NO: 1. In an aspect, at least 2, 3, 4, 5, 6, 7, 8, 9, 10, 11, 12, 13, 14, 15, 16, 17, 18, 19 or 20 amino acids are different from the amino acid sequence of SEQ ID NO: 1.

In an aspect, the disclosure provides a polypeptide comprising the amino acid sequence Met $Xaa_2$ Ile $Xaa_4$ Val $Xaa_6$ Thr $Xaa_8$ $Xaa_9$ $Xaa_{10}$ $Xaa_{11}$ $Xaa_{12}$ Ile $Xaa_{14}$ Leu Glu Val Glu Pro Ser Asp Thr Ile Glu Asn Val Lys Ala Lys Ile Gln Asp Lys Glu Gly Ile Pro Pro Asp Gln Gln Arg Leu $Xaa_{44}$ Phe $Xaa_{46}$ $Xaa_{47}$ $Xaa_{48}$ $Xaa_{49}$ Leu Glu Asp Gly Arg Thr Leu Ser Asp Tyr Asn Ile $Xaa_{62}$ $Xaa_{63}$ $Xaa_{64}$ Ser $Xaa_{66}$ $Xaa_{67}$ $Xaa_{68}$ $Xaa_{69}$ $Xaa_{70}$ $Xaa_{71}$ $Xaa_{72}$ $Xaa_{73}$ $Xaa_{74}$ $Xaa_{75}$ $Xaa_{76}$, wherein one or more of the modifications listed below are selected: $Xaa_2$ is Leu or Arg, $Xaa_4$ is Tyr or Ile, $Xaa_6$ is Thr, $Xaa_8$ is Phe or Asp, $Xaa_9$ is Ala or Met, $Xaa_{10}$ is Arg or Trp, $Xaa_{11}$ is Met, $Xaa_{12}$ is Pro or Arg, $Xaa_{14}$ is Ser, $Xaa_{44}$ is Ala or Tyr, $Xaa_{46}$ is Gly, $Xaa_{47}$ is Glu, Asp or Ala, $Xaa_{48}$ is Met or Ser, $Xaa_{49}$ is Arg, Asp or Ser, $Xaa_{62}$ is Lys or Leu, $Xaa_{63}$ is Asn, $Xaa_{64}$ is Asp, $Xaa_{66}$ is Ser or Lys, $Xaa_{67}$ is Leu or Lys, $Xaa_{68}$ is Phe, Asn, or Leu, $Xaa_{69}$ is Pro, $Xaa_{70}$ is Leu, $Xaa_{71}$ is Val, $Xaa_{72}$ is Lys or Asn, $Xaa_{73}$ is Asn, $Xaa_{74}$ is Ser or Leu, $Xaa_{75}$ is Val or Arg or is absent, and $Xaa_{76}$ is Thr or Val or is absent [SEQ ID NO: 48].

In an aspect, the disclosure provides a polypeptide comprising the amino acid sequence Met $Xaa_2$ Ile $Xaa_4$ Val $Xaa_6$ Thr $Xaa_8$ $Xaa_9$ $Xaa_{10}$ $Xaa_{11}$ $Xaa_{12}$ Ile $Xaa_{14}$ Leu Glu Val Glu Pro Ser Asp Thr Ile Glu Asn Val Lys Ala Lys Ile Gln Asp Lys Glu Gly Ile Pro Pro Asp Gln Gln Arg Leu $Xaa_{44}$ Phe $Xaa_{46}$ $Xaa_{47}$ $Xaa_{48}$ $Xaa_{49}$ Leu Glu Asp Gly Arg Thr Leu Ser Asp Tyr Asn Ile $Xaa_{62}$ $Xaa_{63}$ $Xaa_{64}$ Ser $Xaa_{66}$ $Xaa_{67}$ $Xaa_{68}$ $Xaa_{69}$ $Xaa_{70}$ $Xaa_{71}$ $Xaa_{72}$ $Xaa_{73}$ $Xaa_{74}$ $Xaa_{75}$ $Xaa_{76}$, wherein the amino acid sequence comprises one or more modified amino acid residues selected from: $Xaa_2$ is Leu or Arg, $Xaa_4$ is Tyr or Ile, $Xaa_6$ is Thr, $Xaa_8$ is Phe or Asp, $Xaa_9$ is Ala or Met, $Xaa_{10}$ is Arg or Trp, $Xaa_{11}$ is Met, $Xaa_{12}$ is Pro or Arg, $Xaa_{14}$ is Ser, $Xaa_{44}$ is Ala or Tyr, $Xaa_{46}$ is Gly, $Xaa_{47}$ is Glu, Asp or Ala, $Xaa_{48}$ is Met or Ser, $Xaa_{49}$ is Arg, Asp or Ser, $Xaa_{62}$ is Lys or Leu, $Xaa_{63}$ is Asn, $Xaa_{64}$ is Asp, $Xaa_{66}$ is Ser or Lys, $Xaa_{67}$ is Leu or Lys, $Xaa_{68}$ is Phe, Asn, or Leu, $Xaa_{69}$ is Pro, $Xaa_{70}$ is Leu, $Xaa_{71}$ is Val, $Xaa_{72}$ is Lys or Asn, $Xaa_{73}$ is Asn, $Xaa_{74}$ is Ser or Leu, $Xaa_{75}$ is Val or Arg or is absent, and $Xaa_{76}$ is Thr or Val or is absent [SEQ ID NO: 48].

In an aspect, the polypeptide comprises an Ala at $Xaa_{44}$ or position 44 of SEQ ID NO: 1.

In an aspect, $Xaa_{75}$ or Gly75 of SEQ ID NO: 1 is absent in the polypeptide.

In an aspect, $Xaa_{76}$ or Gly76 of SEQ ID NO: 1 is absent in the polypeptide.

In an aspect, $Xaa_{75}$ and $Xaa_{76}$, or $Gly_{75}$ and $Gly_{76}$ of SEQ ID NO: 1 are absent in the polypeptide.

In an aspect, the polypeptide comprises a Leu at $Xaa_2$ or position 2 of SEQ ID NO:1.

In an aspect, the polypeptide comprises a Leu at $Xaa_{62}$ or position 62 of SEQ ID NO: 1 .

In an aspect, the polypeptide comprises an Asp at $Xaa_{64}$ or position 64 of SEQ ID NO: 1 .

In an aspect, the polypeptide comprises a Lys at $Xaa_{66}$ or position 66 of SEQ ID NO:1.

In an aspect, the polypeptide comprises a Pro at $Xaa_{69}$ or position 69 of SEQ ID NO: 1.

In an aspect, the polypeptide comprises a Leu at $Xaa_{70}$ or position 70 of SEQ ID NO:1.

In an aspect, the polypeptide comprises a Ser at $Xaa_{49}$ or position 49 of SEQ ID NO:1.

In an aspect, the polypeptide comprises a Leu at $Xaa_2$ and $Xaa_{62}$, or positions 2 and 62 of SEQ ID NO:1.

In an aspect, the polypeptide comprises a Leu at $Xaa_2$, $Xaa_{62}$ and $Xaa_{70}$, or positions 2, 62 and 70 of SEQ ID NO:1.

In an aspect, the polypeptide comprises a Leu at $Xaa_2$, $Xaa_{62}$ and/or $Xaa_{70}$, or positions 2, 62 and/or 70 of SEQ ID NO:1.

A polypeptide comprising amino acid replacements at positions corresponding to positions 2 and 66 in a disclosed polypeptide having the sequence of amino acids set forth in SEQ ID NO: 1, wherein the amino acid replacement at position 2 is Leu and at position 66 is Lys, and the polypeptide exhibits binding affinity to 53BP1 tandem Tudor domain and inhibition of 53BP1.

In an aspect, a disclosed polypeptide comprises a Leu at $Xaa_2$ and $Xaa_{62}$ or positions 2 and 62 of SEQ ID NO: 1, an Asp at $Xaa_{64}$ or position 64 of SEQ ID NO: 1, a Lys at $Xaa_{66}$ or position 66 of SEQ ID NO: 1 and a Pro at $Xaa_{69}$ or position 69 of SEQ ID NO: 1.

In an aspect, a disclosed polypeptide comprises a Leu at $Xaa_2$, $Xaa_{62}$ and/or $Xaa_{70}$ or positions 2, 62 and/or 70 of SEQ ID NO:1, an Asp at $Xaa_{64}$ or position 64 of SEQ ID NO:1, a Lys at $Xaa_{66}$ or position 66 of SEQ ID NO:1, and a Pro at $Xaa_{69}$ or position 69 of SEQ ID NO:1.

In an aspect, a disclosed polypeptide comprises a Leu at $Xaa_2$ or position 2 of SEQ ID NO:1, an Asp at $Xaa_{64}$ or position 64 of SEQ ID NO:1, a Lys at $Xaa_{66}$ or position 66 of SEQ ID NO:1, and a Pro at $Xaa_{69}$ or position 69 of SEQ ID NO:1.

In an aspect, a disclosed polypeptide comprises a Leu at $Xaa_2$, $Xaa_{62}$ and $Xaa_{70}$ or positions 2, 62 and 70 of SEQ ID NO:1, an Ala at $Xaa_{44}$ or position 44 of SEQ ID NO:1, an Asp at $Xaa_{64}$ or position 64 of SEQ ID NO:1, a Lys at $Xaa_{66}$ or position 66 of SEQ ID NO:1, and a Pro at $Xaa_{69}$ or position 69 of SEQ ID NO:1.

In an aspect, a disclosed polypeptide comprises a Leu at $Xaa_2$ and $Xaa_{62}$ or positions 2 and 62 of SEQ ID NO: 1, an Ile at $Xaa_{44}$ or position 44 of SEQ ID NO: 1, a Ser at $Xaa_{49}$ or position 49 of SEQ ID NO: 1, an Asp at $Xaa_{64}$ or position 64 of SEQ ID NO: 1, and a Lys at $Xaa_{66}$ or position 66 of SEQ ID NO: 1.

In an aspect, a disclosed polypeptide comprises a Leu at $Xaa_2$ and $Xaa_{62}$ or positions 2 and 62 of SEQ ID NO: 1, an Asp at $Xaa_{64}$ or position 64 of SEQ ID NO: 1, and a Lys at $Xaa_{66}$ or position 66 of SEQ ID NO: 1.

In an aspect, a disclosed polypeptide comprises a Leu at $Xaa_2$ and $Xaa_{62}$ or positions 2 and 62 of SEQ ID NO: 1, a Ser at $Xaa_{49}$ or position 49 of SEQ ID NO: 1, an Asp at $Xaa_{64}$ or position 64 of SEQ ID NO: 1 and a Lys at $Xaa_{66}$ or position 66 of SEQ ID NO: 1.

In an aspect, a disclosed polypeptide comprises a Leu at one or more of $Xaa_2$, $Xaa_{62}$ and $Xaa_{70}$ or positions 2, 62 and 70 of SEQ ID NO:1, an Ala at $Xaa_{44}$ or position 44 of SEQ ID NO:1, an Asp at $Xaa_{64}$ or position 64 of SEQ ID NO:1, a Lys at $Xaa_{66}$ or position 66 of SEQ ID NO:1, and a Pro at $Xaa_{69}$ or position 69 of SEQ ID NO:1.

In an aspect, a disclosed polypeptide comprises a Leu at $Xaa_2$, $Xaa_{62}$ and $Xaa_{70}$ or positions 2, 62 and 70 of SEQ ID NO:1, an Ala at $Xaa_{44}$ or position 44 of SEQ ID NO:1, an Asp at $Xaa_{64}$ or position 64 of SEQ ID NO:1, a Lys at $Xaa_{66}$ or position 66 of SEQ ID NO:1 and a Pro at $Xaa_{69}$ or position 69 of SEQ ID NO:1.

In an aspect, a disclosed polypeptide comprises a Leu at $Xaa_2$, $Xaa_{62}$ and $Xaa_{70}$ or positions 2, 62 and 70 of SEQ ID NO:1, an Ala at $Xaa_{44}$ or position 44 of SEQ ID NO:1, a Ser at $Xaa_{49}$ or position 49 of SEQ ID NO:1, an Asp at $Xaa_{64}$ or position 64 of SEQ ID NO:1, a Lys at $Xaa_{66}$ or position 66 of SEQ ID NO:1 and a Pro at $Xaa_{69}$ or position 69 of SEQ ID NO:1.

In an aspect, a disclosed polypeptide comprises a Thr at $Xaa_6$ or position 6 of SEQ ID NO:1.

In an aspect, a disclosed polypeptide comprises an Asp at $Xaa_8$, $Xaa_{47}$ and/or $Xaa_{49}$ or positions 8, 47 and/or 49 of SEQ ID NO:1.

In an aspect, a disclosed polypeptide comprises a Met at $Xaa_9$ and/or $Xaa_{11}$ or positions 9 and/or 11 of SEQ ID NO:1.

In an aspect, a disclosed polypeptide comprises a Ser at $Xaa_{14}$ and/or $Xaa_{66}$ or positions 14 and/or 66 of SEQ ID NO:1.

In an aspect, a disclosed polypeptide comprises a Gly at $Xaa_{46}$ or position 46 of SEQ ID NO:1.

In an aspect, a disclosed polypeptide comprises an Asn at $Xaa_{68}$ or position 68 of SEQ ID NO:1.

In an aspect, a disclosed polypeptide comprises a Lys at $Xaa_{72}$ or position 72 of SEQ ID NO:1.

In an aspect, a disclosed polypeptide comprises a Leu at $Xaa_2$ or position 2 of SEQ ID NO:1, a Thr at $Xaa_6$ or position 6 of SEQ ID NO: 1, an Asp at $Xaa_8$, $Xaa_{47}$, and/or $Xaa_{49}$ or positions 8, 47 and/or 49 of SEQ ID NO:1 , a Met at $Xaa_9$ and/or Xaa$_{11}$ or positions 9 and/or 11 of SEQ ID NO:1, a Ser at Xaa$_{14}$ and/or Xaa$_{66}$ or positions 14 and/or 66 of SEQ ID NO:1, a Gly at Xaa$_{46}$ or position 46 of SEQ ID NO:1, an Asn at Xaa$_{68}$ or position 68 of SEQ ID NO:1, and a Lys at Xaa$_{72}$ or position 72 of SEQ ID NO:1.

In an aspect, a disclosed polypeptide comprises a Tyr at Xaa$_4$ or positions 4 of SEQ ID NO:1.

In an aspect, a disclosed polypeptide comprises a Phe at Xaa$_8$ and/or Xaa$_{68}$ or positions 8 and/or 68 of SEQ ID NO: 1.

In an aspect, a disclosed polypeptide comprises an Ala at Xaa$_9$ or position 9 of SEQ ID NO:1.

In an aspect, a disclosed polypeptide comprises an Arg at Xaa$_{10}$ and/or Xaa$_{49}$ or positions 10 and/or 49 of SEQ ID NO:1.

In an aspect, a disclosed polypeptide comprises a Pro at Xaa$_{12}$ or position 12 of SEQ ID NO:1.

In an aspect, a disclosed polypeptide comprises a Glu at Xaa$_{47}$ or position 47 of SEQ ID NO:1.

In an aspect, a disclosed polypeptide comprises a Met at Xaa$_{48}$ or position 48 of SEQ ID NO: 1.

In an aspect, a disclosed polypeptide comprises a Lys at Xaa$_{62}$ and/or Xaa$_{72}$ or positions 62 and/or 72 of SEQ ID NO:1.

In an aspect, a disclosed polypeptide comprises an Asn at Xaa$_{63}$ and/or Xaa$_{73}$ or positions 63 and/or 73 of SEQ ID NO:1.

In an aspect, a disclosed polypeptide comprises a Ser at Xaa$_{74}$ or position 74 of SEQ ID NO:1.

In an aspect, a disclosed polypeptide comprises a Val at Xaa$_{75}$ or position 75 of SEQ ID NO:1.

In an aspect, a disclosed polypeptide comprises a Thr at Xaa$_{76}$ or position 76 of SEQ ID NO:1.

In an aspect, a disclosed polypeptide comprises a Tyr at Xaa$_4$ or position 4 of SEQ ID NO:1, a Phe at Xaa$_8$ and/or Xaa$_{68}$ or positions 8 and/or 68 of SEQ ID NO:1, an Ala at Xaa$_9$ or position 9 of SEQ ID NO:1, an Arg at Xaa$_{10}$ and/or Xaa$_{49}$ or positions 10 and/or 49 of SEQ ID NO:1, a Pro at Xaa$_{12}$ or position 12 of SEQ ID NO:1, a Glu at Xaa$_{47}$ or position 47 of SEQ ID NO:1, a Met at Xaa$_{48}$ or position 48 of SEQ ID NO:1, a Lys at Xaa$_{62}$ and/or Xaa$_{72}$ or positions 62 and/or 72 of SEQ ID NO:1, an Asn at Xaa$_{63}$ and/or Xaa$_{73}$ or positions 63 and/or 73 of SEQ ID NO:1, an Asp at Xaa$_{64}$ or position 64 of SEQ ID NO:1, a Ser at Xaa$_{74}$ or position 74 of SEQ ID NO:1, a Val at Xaa$_{75}$ or position 75 of SEQ ID NO:1, and a Thr at Xaa$_{76}$ or position 76 of SEQ ID NO:1.

In an aspect, a disclosed polypeptide comprises a Trp at Xaa$_{10}$ or position 10 of SEQ ID NO:1.

In an aspect, a disclosed polypeptide comprises an Asn at Xaa$_{68}$ and/or Xaa$_{72}$ or positions 68 and/or 72 of SEQ ID NO:1.

In an aspect, a disclosed polypeptide comprises an Arg at Xaa$_{12}$ or position 12 of SEQ ID NO:1.

In an aspect, a disclosed polypeptide comprises a Thr at Xaa$_6$ or position 6 of SEQ ID NO:1, an Asp at Xaa$_8$, Xaa$_{47}$ and/or Xaa$_{49}$ or positions 8, 47 and/or 49 of SEQ ID NO:1, a Met at Xaa$_9$ and/or Xaa$_{11}$ or positions 9 and/or 11 of SEQ ID NO:1, a Trp at Xaa$_{10}$ or position 10 of SEQ ID NO:1, an Arg at Xaa$_{12}$ or position 12 of SEQ ID NO:1, a Gly at Xaa$_{46}$ or position 46 of SEQ ID NO:1, a Ser at Xaa$_{14}$ and/or Xaa$_{66}$ or positions 14 and/or 66 of SEQ ID NO:1, and an Asn at Xaa$_{68}$ and/or Xaa$_{72}$ or positions 68 and/or 72 of SEQ ID NO:1.

In an aspect, a disclosed polypeptide comprises an Arg at Xaa$_2$, Xaa$_{10}$ and/or Xaa$_{75}$ or positions 2, 10 and/or 75 of SEQ ID NO:1.

In an aspect, a disclosed polypeptide comprises an Ile at Xaa$_4$ or position 4 of SEQ ID NO:1.

In an aspect, a disclosed polypeptide comprises a Tyr at Xaa$_{44}$ or position 44 of SEQ ID NO:1.

In an aspect, a disclosed polypeptide comprises an Ala at Xaa$_{47}$ or position 47 of SEQ ID NO:1.

In an aspect, a disclosed polypeptide comprises a Ser at Xaa$_{48}$ or position 48 of SEQ ID NO:1.

In an aspect, a disclosed polypeptide comprises a Leu at Xaa$_{68}$ and/or Xaa$_{74}$ or positions 68 and/or 74 of SEQ ID NO:1.

In an aspect, a disclosed comprises a Val at Xaa$_{71}$ and/or Xaa$_{76}$ or positions 71 and/or 76 of SEQ ID NO:1.

In an aspect, a disclosed polypeptide comprises an Arg at Xaa$_2$ and/or Xaa$_{75}$ or positions 2 and/or 75 of SEQ ID NO:1, an Ile at Xaa$_4$ or position 4 of SEQ ID NO:1, a Phe at Xaa$_8$ or position 8 of SEQ ID NO:1, a Met at Xaa$_9$ or position 9 of SEQ ID NO:1, a Pro at Xaa$_{12}$ or position 12 of SEQ ID NO:1, a Tyr at Xaa$_{44}$ or position 44 of SEQ ID NO:1, an Ala at Xaa$_{47}$ or position 47 of SEQ ID NO:1, a Ser at Xaa$_{48}$ or position 48 of SEQ ID NO:1, a Leu at Xaa$_{68}$ and/or Xaa$_{74}$ or positions 68 and/or 74 of SEQ ID NO:1, and a Val at Xaa$_{71}$ and/or Xaa$_{76}$ or positions 71 and/or 76 of SEQ ID NO:1.

In an aspect, a disclosed polypeptide comprises the amino acid sequence: Met Gln Ile Tyr Val Lys Thr Phe Ala Arg Lys Pro Ile Thr Leu Glu Val Glu Pro Ser Asp Thr Ile Glu Asn Val Lys Ala Lys Ile Gln Asp Lys Glu Gly Ile Pro Pro Asp Gln Gln Arg Leu Ile Phe Ala Glu Met Arg Leu Glu Asp Gly Arg Thr Leu Ser Asp Tyr Asn Ile Lys Asn Asp Ser Thr Leu Phe Leu Val Leu Lys Asn Ser Val Thr (FIG. 1C; A10; SEQ ID NO: 2), or solvate or salt thereof.

In an aspect, a disclosed polypeptide comprises the amino acid sequence: Met Leu Ile Phe Val Thr Thr Asp Met Gly Met Thr Ile Ser Leu Glu Val Glu Pro Ser Asp Thr Ile Glu Asn Val Lys Ala Lys Ile Gln Asp Lys Glu Gly Ile Pro Pro Asp Gln Gln Arg Leu Ile Phe Gly Asp Lys Asp Leu Glu Asp Gly Arg Thr Leu Ser Asp Tyr Asn Ile Gln Lys Glu Ser Ser Leu Asn Leu Val Leu Lys Leu Arg Gly Gly (FIG. 1C; A11; SEQ ID NO: 3), or solvate or salt thereof.

In an aspect, a disclosed polypeptide comprises the amino acid sequence: Met Gln Ile Phe Val Thr Thr Asp Met Trp Met Arg Ile Ser Leu Glu Val Glu Pro Ser Asp Thr Ile Glu Asn Val Lys Ala Lys Ile Gln Asp Lys Glu Gly Ile Pro Pro Asp Gln Gln Arg Leu Ile Phe Gly Asp Lys Asp Leu Glu Asp Gly Arg Thr Leu Ser Asp Tyr Asn Ile Gln Lys Glu Ser Ser Leu Asn Leu Val Leu Asn Leu Arg Gly Gly (FIG. 1C; C08; SEQ ID NO: 4), or solvate or salt thereof.

In an aspect, a disclosed polypeptide comprises the amino acid sequence: Met-Leu-Ile-Phe-Val-Lys-Thr-Leu-Thr-Gly-Lys-Thr-Ile-Thr-Leu-Glu-Val-Glu-Pro-Ser-Asp-Thr-Ile-Glu-Asn-Val-Lys-Ala-Lys-Ile-Gln-Asp-Lys-Glu-Gly-Ile-Pro-Pro-Asp-Gln-Gln-Arg-Leu-Ile-Phe-Ala-Gly-Lys-Ser-Leu-Glu-Asp-Gly-Arg-Thr-Leu-Ser-Asp-Tyr-Asn-Ile-Leu-Lys-Asp- Ser-Lys-Leu-His-Pro-Leu-Leu-Arg-Leu-Arg-Gly-Gly (FIG. 1C, G08; SEQ ID NO: 5), or solvate or salt thereof.

In an aspect, a disclosed polypeptide comprises the amino acid sequence: Met Arg Ile Ile Val Lys Thr Phe Met Arg Lys Pro Ile Thr Leu Glu Val Glu Pro Ser Asp Thr Ile Glu Asn Val Lys Ala Lys Ile Gln Asp Lys Glu Gly Ile Pro Pro Asp Gln Gln Arg Leu Tyr Phe Ala Ala Ser Gln Leu Glu Asp Gly Arg Thr Leu Ser Asp Tyr Asn Ile Gln Lys Glu Ser Thr Leu Leu Leu Val Val Arg Leu Leu Arg Val (FIG. 1C; H04; SEQ ID NO: 6), or solvate or salt thereof.

In an aspect, a disclosed polypeptide comprises the amino acid sequence: Met-Leu-Ile-Phe-Val-Lys-Thr-Leu-Thr-Gly- Lys-Thr-Ile-Thr-Leu-Glu-Val-Glu-Pro-Ser-Asp-Thr-Ile-Glu-Asn- Val-Lys-Ala-Lys-Ile-Gln-Asp-Lys-Glu-Gly-Ile-Pro-Pro- Asp-Gln-Gln-Arg-Leu-Ile-Phe-Ala-Gly-Lys-Ser-Leu-Glu-Asp-Gly-Arg-Thr-Leu-Ser-Asp-Tyr-Asn-Ile-Leu-Lys-Asp-Ser-Lys-Leu-His-Pro-Leu-Leu-Arg-Leu-Arg (SEQ ID NO: 7), or solvate or salt thereof.

In an aspect, a disclosed polypeptide comprises the amino acid sequence: Met-Leu-Ile-Phe-Val-Lys-Thr-Leu-Thr-Gly-Lys-Thr-Ile-Thr-Leu-Glu-Val-Glu-Pro-Ser-Asp-Thr-Ile-Glu-Asn-Val-Lys-Ala-Lys-Ile-Gln-Asp-Lys-Glu-Gly-Ile-Pro-Pro- Asp-Gln-Gln-Arg-Leu-Ala-Phe-Ala-Gly-Lys-Ser-Leu-Glu-Asp-Gly-Arg-Thr-Leu-Ser-Asp-Tyr-Asn-Ile-Leu-Lys-Asp-Ser-Lys-Leu-His-Pro-Leu-Leu-Arg-Leu-Arg-Gly-Gly (SEQ ID NO: 8), or solvate or salt thereof.

In an aspect, a disclosed polypeptide comprises the amino acid sequence: Met-Leu-Ile-Phe-Val-Lys-Thr-Leu-Thr-Gly-Lys-Thr-Ile-Thr-Leu-Glu-Val-Glu-Pro-Ser-Asp-Thr-Ile-Glu-Asn-Val-Lys-Ala-Lys-Ile-Gln-Asp-Lys-Glu-Gly-Ile-Pro-Pro- Asp-Gln-Gln-Arg-Leu-Ala-Phe-Ala-Gly-Lys-Ser-Leu-Glu-Asp-Gly-Arg-Thr-Leu-Ser-Asp-Tyr-Asn-Ile-Leu-Lys-Asp-Ser-Lys-Leu-His-Pro-Leu-Leu-Arg-Leu-Arg (SEQ ID NO: 9; also referred to herein as i53), or solvate or salt thereof.

In an aspect, a disclosed polypeptide comprises the amino acid sequence: Met-Leu-Ile-Phe-Val-Lys-Thr-Leu-Thr-Gly-Lys-Thr-Ile-Thr-Leu-Glu-Val-Glu-Pro-Ser-Asp-Thr-Ile-Glu-Asn-Val-Lys-Ala-Lys-Ile-Gln-Asp-Lys-Glu-Gly-Ile-Pro-Pro- Asp-Gln-Gln-Arg-Leu-Ile-Phe-Ala-Gly-Lys-Ser-Leu-Glu-Asp-Gly-Arg-Thr-Leu-Ser-Asp-Tyr-Asn-Ile-Leu-Lys-Asp-Ser-Lys-Leu-His-Leu-Val-Leu-Arg-Leu-Arg-Gly-Gly (SEQ ID NO: 10; also referred to herein as UbvGO8-DM), or solvate or salt thereof.

In an aspect, a disclosed polypeptide comprises the amino acid sequence: Met-Leu-Ile-Phe-Val-Lys-Thr-Leu-Thr-Gly-Lys-Thr-Ile-Thr-Leu-Glu-Val-Glu-Pro-Ser-Asp-Thr-Ile-Glu-Asn-Val-Lys-Ala-Lys-Ile-Gln-Asp-Lys-Glu-Gly-Ile-Pro-Pro- Asp-Gln-Gln-Arg-Leu-Ala-Phe-Ala-Gly-Lys-Ser-Leu-Glu-Asp-Gly-Arg-Thr-Leu-Ser-Asp-Tyr-Asn-Ile-Leu-Lys-Asp-Ser-Lys-Leu-His-Leu-Val-Leu-Arg-Leu-Arg (SEQ ID NO: 11; also referred to herein as i53-DM), or solvate or salt thereof.

The disclosure also provides fragments and fusion proteins of polypeptides disclosed herein with the proviso that they bind the 53BP1 tandem Tudor domain or inhibit 53BP1. The polypeptides may be coupled to (reporter) enzymes, toxins or other binding proteins.

In another aspect, the disclosure provides an isolated polynucleotide encoding any of the disclosed polypeptides, an expression vector comprising the polynucleotide, and a host cell comprising the polynucleotide. The disclosure also features a method of producing a polypeptide disclosed herein by culturing the host cell in a medium under conditions permitting expression of a polypeptide encoded by the polynucleotide, and purifying the polypeptide from the cultured cell or the medium of the cell.

In another aspect, an isolated cell and cell lines are provided comprising any of the polypeptides and/or polynucleotides described herein.

The present disclosure provides a method for making a polypeptide disclosed herein. The method includes, among others, steps of providing a polypeptide of SEQ ID NO: 1 and modifying SEQ ID NO: 1 as disclosed herein to obtain a modified polypeptide disclosed herein. In an aspect, a method is provided comprising the steps of providing a polypeptide of SEQ ID NO: 1 and modifying SEQ ID NO: 1 as disclosed herein to obtain a modified polypeptide that exhibits binding affinity or binds to 53BP1 tandem Tudor domain and inhibition of 53BP1. The present disclosure also provides a polypeptide made by the disclosed method.

Transgenic organisms are provided carrying one or more sequences encoding polypeptides disclosed herein and/or one or more exogenous sequences (e.g., sequences inserted into the genome via targeted integration).

A composition comprising a polypeptide and/or polynucleotide disclosed herein is provided. In an aspect, the disclosure provides a composition comprising a polypeptide as disclosed herein, or a salt or solvate thereof, in admixture with a carrier, excipient and/or diluent. The disclosure also provides a composition wherein the composition is a pharmaceutically acceptable composition, and the carrier is a pharmaceutically acceptable carrier. The disclosure also provides a pharmaceutically acceptable composition comprising an effective amount of a polypeptide and/or polynucleotide disclosed herein and a pharmaceutically acceptable carrier.

The polypeptides and polynucleotides disclosed herein may be used in a broad spectrum of applications. The polypeptides and polynucleotides disclosed herein may be used for the detection and quantitative determination as well as for the separation and isolation of 53BP1. The polypeptides and polynucleotides disclosed herein may be used in genomic engineering, epigenomic engineering, genome targeting, and genome editing. The polypeptides and polynucleotides disclosed herein may be used to modify repair pathways, activate or stimulate HR or homology-based genome editing, inhibit 53BP1 recruitment to DSB sites or damaged chromatin in a cell or modulate DNA end resection. In an aspect, the polypeptides and polynucleotides disclosed herein are used in combination with a gene editing system.

The disclosure also provides the use of the polypeptides and polynucleotides disclosed herein as medicaments, particularly for the treatment of an HR Disease as disclosed herein.

The disclosure further provides kits for performing methods disclosed herein.

The disclosure also contemplates the use of methods, compositions and kits disclosed herein in genome modification or genome engineering provided that said use is not a method for treatment of the human or animal body by surgery or therapy, and provided that said use is not a process for modifying the germ line genetic identity of human beings.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

FIG. 1. Identification of 53BP1-binding ubiquitin variants. FIG. 1A, Schematic representation of 53BP1, highlighting the focus-forming region (FFR), which is necessary and sufficient for the recruitment of 53BP1 to DSB sites. FIG. 1B, Phage enzyme-linked immunosorbent assays (ELISAs) for binding to the following immobilized proteins (color coded as indicated in the panel): USP5, USP7, SMURF1, HACE, HOIP, HOIL, 53BP1 (Tudor-UDR region), NBD, SMURF2, CDC4, OTUB1, FBW7, USP8, ITCH, USP21, USP14 and BSA. Bound phages were detected spectrophotometrically (optical density at 450 nm), and background binding to neutravidin was subtracted from the signal. The single elevated histogram bars for each of phages A10, A11, C08, C12, G08 and H04 correspond to 53BP1. FIG. 1C, Sequence alignments of the 53BP1-binding Ubvs.

FIG. 2. Structure of the UbvG08 bound to the 53BP1 Tudor domain.

FIG. 3. The i53 protein inhibits 53BP1.

FIG. 4. Activation of HR by i53.

FIG. 5 (Related to FIG. 2.) FIG. 5A, Structural overlay of the newly determined 53BP1 Tudor domain, the apo 53BP1 Tudor domain (PDB 1XNI) and 53BP1 Tudor domain bound to a H4K20me2 peptide ligand (PDB 2IG0). FIG. 5B, Structural overlay of UbvG08 and native ubiquitin. FIG. 5C, Structure-guided sequence alignment of UbvG08 (SEQ ID NO: 51) and native ubiquitin (SEQ ID NO: 1). Secondary structural elements of native ubiquitin and UbvG08 are highlighted above and below the sequence alignment, respectively. Residue differences between ubiquitin and UbvG08 are highlighted in orange. A register shift in strand β5 is responsible for an increase in the size of the preceding loop (boxed in black) in UbvG08. FIG. 5D, Structural overlay of UbvG08 and native ubiquitin highlighting the difference in position of Q62 in ubiquitin with that of L62 in UbvG08 that may contribute to the differential conformation of a tight loop preceding strand β5. FIG. 5E, Zoom-in of the loop preceding β5 and strand β5 in ubiquitin superimposed on UbvG08. UbvG08 residues D64 (corresponding to residue E64 in ubiquitin) and K66 (corresponding to residue T66 in ubiquitin) are drastically displaced by the register shift in strand β5.

or 1 μM SCR7 (+). The percentage of GFP-positive cells was determined 48 h post-transfection for each condition and was normalized to the DM condition (mean±s.d., N=4). FIG 5E, U2OS EJ2-GFP cells were transfected with the vectors expressing Flag-tagged i53, its DM mutant or an empty vector control (EV) along with an I-Scel expression vector. The percentage of GFP-positive cells was determined 48 h post-transfection for each condition and was normalized to the empty vector condition (mean±s.d., N=4).

FIG. 9 Expression of i53 suppresses PARP inhibitor sensitivity of BRCA1-deficience cells.

FIG. 10. Adeno-associated viral-mediated delivery of i53 stimulates homologous recombination.

FIG. 11. 53BP1 inhibition by i53 stimulates ssODN-mediated homologous recombination. FIG. 11A, Schematic of the BFP-to-GFP conversion assay. Cells carrying a stably integrated BFP transgene are transfected with Cas9 ribonucleoproteins (RNPs) programmed with a gRNA against the BFP coding sequence along with an ssODN that converts 3 nucleotides of BFP into those that produce a GFP protein upon successful HR-mediated repair. FIG. 11B-C, 293T cells that were first transduced with AAV-DJ1 vectors coding for i53-DM or i53 with the BFP transgene were nucleofected with Cas9 RNPs and optimal (b) and suboptimal (c) ssODN repair donors that convert BFP to GFP. 4 d after nucleofection, GFP fluorescence was monitored by flow cytometry. Shown are three independent experiments, the lines connect the DM and wild type i53 conditions done at the same time FIG. 11D-E, 293T (D) and K562 (E) cells previously transduced with AAV-DJ1 vectors coding for i53-DM or i53 were nucleofected with Cas9 RNPs programmed to cut at the CCR5 and CXCR4 loci. ssODN repair donors that introduce point mutations and new PciI restriction sites were also nucleofected with the RNP. 3 d post-nucleofection, genomic DNA was isolated and the presence of the PciI restriction fragment length polymorphism (RFLP) was determined by restriction digest on PCR-amplified genomic DNA. On the left panels are shown the results of independent experiments, and the lines connecting the DM and wild type i53 values correspond to conditions done at the same time. Relative editing efficiency are shown on the right panel as the mean +/- S.E.M (N=4).

DETAILED DESCRIPTION

Terminology

Figure 1D:
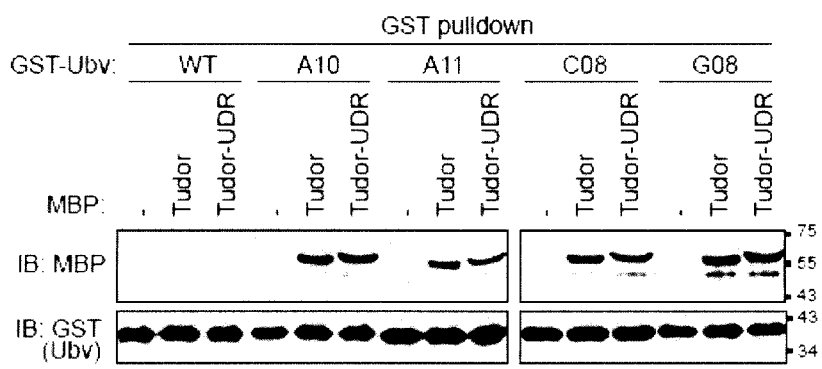
FIG. 1D, Pulldown assays of the indicated GST-Ubv fusion with either MBP alone (−) or MBP fused to the Tudor or Tudor-UDR fragments of 53BP1.

The preparation and use of the agents and compositions disclosed as well as the practice of the methods herein employed, unless otherwise indicated, utilize conventional techniques in molecular biology, biochemistry, chromatin structure and analysis, computational chemistry, cell culture, recombinant DNA and related fields as are within the skill of the art. The techniques are fully disclosed in the literature. [See, for example, Sambrook et al. Molecular Cloning: A Laboratory Manual, Second edition, Cold Spring Harbor Laboratory Press, 1989 and Third edition, 2001; Ausubel et al., Current Protocols in Molecular Biology, John Wiley & Sons, New York, 1987 and periodic updates; the series Methods in Enzymology, Academic Press, San Diego; Wolffe, Chromatin Structure and Function, Third edition, Academic Press, San Diego, 1998; Methods in Enzymology, Vol. 304, "Chromatin" (P. M. Wassarman and A. P. Wolffe, eds.), Academic Press, San Diego, 1999; and Methods in Molecular Biology, Vol. 119, "Chromatin Protocols" (P. B. Becker, ed.) Humana Press, Totowa, 1999].

Unless defined otherwise, all technical and scientific terms used herein have the same meaning as commonly understood by one of ordinary skill in the art to which this invention belongs. The following definitions supplement those in the art and are directed to the present application and are not to be imputed to any related or unrelated case. Although any methods and materials similar or equivalent to those disclosed herein can be used in the practice of the invention, particular materials and methods are disclosed herein.

As used herein and in the appended claims, the singular forms "a", "an", and "the" include plural reference unless the context clearly dictates otherwise. As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

"A ubiquitin-like folding motif" refers to a five-strand β-sheet (β1-5) buttressed against a single α-helix (α1) and a short $3_{10}$ helix characteristic of ubiquitin (Vijay-Kumar et al, 1987, Nature 370, 389-391; Buchberger et al., National Library of Medicine," J Mol Biol. 307(1): 17-24, 2001). In an aspect, the motif is modified by the shifting of four positions of the strand β5 resulting in an increase in the length of the loop preceding strand β5 by 4 residues and a shortening of the C-terminal tail of β5 by 4 residues (see for example, FIG. 5B and FIG. 5C).

An "amino acid" includes natural and synthetic amino acids, and both D and L amino acids, in particular standard amino acids, nonstandard amino acids and synthetic amino acids. A "standard amino acid" refers to any of the twenty L-amino acids commonly found in naturally occurring peptides. A "nonstandard amino acid" means any amino acid, other than the standard amino acids, prepared synthetically or derived from a natural source. A "synthetic amino acid" includes chemically modified amino acids, such as salts, amino acid derivatives (such as amides), and substitutions. The amino acids are represented herein by their full name, their three-letter code, as well as their one-letter code (see Stryer, L (1988), "Biochemistry", (3rd Ed.), W. H. Freeman and Co., New York, for amino acid structures and their abbreviations).

The terms "protein", "peptide" and "polypeptide" are used interchangeably, and refer to a compound comprised of amino acids covalently linked by peptide bonds. In particular aspects, the term refers to both short chains (generally referred to as peptides, oligopeptides and oligomers) and to longer chains (generally referred to as proteins). The terms include, for example, biologically active fragments, substantially homologous proteins, oligopeptides, homodimers, heterodimers, protein variants, modified proteins, derivatives, analogs, and fusion proteins, among others. The proteins include natural proteins, recombinant proteins, synthetic proteins, or a combination thereof.

The terms "polynucleotide", "nucleic acid" and "nucleic acid sequence" are used interchangeably and generally refer to a polymeric form of nucleotides of any length, either ribonucleotides or deoxyribonucleotides. The term includes double- and single-stranded DNA and RNA, mixtures of single-and-double stranded regions, modifications such as methylation or capping and unmodified forms of the polynucleotide. A polynucleotide may, but need not, include additional coding or non-coding sequences, or it may, but need not, be linked to other molecules and/or carrier or support materials. In some applications the term refers to antisense polynucleotides. The terms include many related sequences with the functions described herein. Polynucleotides include complementary nucleic acid sequences, and nucleic acids that are substantially identical to these sequences (e.g. at least about 45%, preferably 50%, 55%, 60%, 65%, 70%, 75%, 80%, 85%, 90%, 95%, 97%, 98%, or 99% sequence identity). Polynucleotides also include sequences that differ from a reference sequence due to degeneracy in the genetic code. Polynucleotides also include artificial or recombinant nucleic acids that hybridize to a polynucleotide under highly stringent conditions over substantially the entire length of the polynucleotide (other than a naturally occurring polynucleotide).

A "gene editing system" is a system for targeting and editing genomes. Examples of gene editing systems include without limitation, a TALEN (Transcription Activator-Like Effector Nucleases) system, a CRISPR (Clustered Regulatory Interspaced Short Palindromic Repeats) system and a Zinc-Finger Nucleases (ZFN) system. (See Nemudryi A.A. et al, Acta Naturae. 2014 Jul-Sep; 6(3): 19-40 for a review of TALEN and CRISPR systems; Gaj T. et al, Trends Biotechnol. 2013 Jul; 31(7): 397-405 for a review of TALEN, CRISPR and ZFN systems; US Published Patent Application No. 20110145940 describing a TALEN system; Bibikova M., et al, Genetics. 2002;161(3):1169-1175; Townsend J. A., et al, Nature 2009;459(7245):442-445; Zhang F., et al, Proc. Natl. Acad. Sci. USA. 2010;107(26): 12028-12033; Torikai H., et al; Blood. 2012;119(24):5697-5705; Provasi E., et al, J.. Nat. Med. 2012;18(5):807-8151, and Lombardo A., et al, Nat. Methods. 2011;8(10):861-869 describing ZFN systems). In some aspects, a combination of elements of different gene editing systems may be used. Elements of a gene editing system can be delivered to a target cell using methods known in the art. If the element is a polypeptide it can be delivered by suitable means such as electroporation, sonoporation, microinjection, liposomal delivery and nanomaterial-based delivery.

A "CRISPR system" includes a CRISPR/Cas system which comprises transcripts and other elements involved in the expression of, or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence, a guide sequence, or other sequences and transcripts from a CRISPR locus. One or more elements of a CRISPR system may be derived from a type I, type II, or type III CRISPR system. A CRISPR system also includes a CRISPR/Cpf1 system comprising Cpf1, an RNA-guided endonuclease.

In some aspects, the CRISPR system is a CRISPR/Cas system. In an embodiment, the CRISPR system is CRISPR/Cas9. In other aspects, the CRISPR system is a CRISPR/Cpf1 system.

A CRISPR system promotes the formation of a CRISPR complex (e.g., comprising a guide sequence hybridized to a target sequence and complexed with one or more Cas proteins) at the site of a target sequence. A "target sequence" refers to a sequence which is sufficiently complementary to a designed guide sequence that the target sequence hybridizes to the guide sequence promoting the formation of a CRISPR complex. A target sequence may comprise any polynucleotide, such as DNA or RNA polynucleotides, and it may be located in the nucleus, cytoplasm, an organelle, for example, mitochondria or chloroplast. In the context of an endogenous CRISPR system, formation of a CRISPR complex in an endogenous CRISPR system results in cleavage of one or both strands in or near (e.g. within 1, 2, 3, 4, 5, 6, 7, 8, 9, 10, 20, 50, or more base pairs from) the target sequence.

CRISPR systems are described in U.S. Pat. Nos. 8,697,359, 8,771,945, 8,795,965, 8,865,406, 8,871,445, 8,889,356, 8,889,418 and 8,895,308; US Patent Publications US 2014-0310830, US 2014-0287938, US 2014-0273234, US2014-0273232, US 2014-0273231, US 2014-0256046, US 2014-0248702), US 2014-0242700, US 2014-0242699, US 2014-0242664, US 2014-0234972, US 2014-0227787, US 2014-0189896, US 2014-0186958, US 2014-0186919, US 2014-0186843, US 2014-0179770 and US 2014-0179006, US 2014-0170753, US 20150232883 and US 20150291966; European Patent Applications EP 2771468 (EP13818570.7), EP 2764103 (EP13824232.6), and EP 2784162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418) and WO2014/093622 (PCT/US2013/074667). General information on CRISPR systems is also described in the following publications: Cong, L., et al., Science, February 15; 339(6121):819-23 (2013); Jiang W., et al., Nat Biotechnol March; 31(3):233-9 (2013); Wang H., et al, Cell May 9; 153(4):910-8 (2013); Konermann S, et al, Nature. 2013 Aug. 22; 500(7463):472-6. doi: 10.1038/Nature12466. Epub 2013 Aug. 23; Ran, F A., et al, Cell August 28. pii: S0092-8674(13)01015-5. (2013); Hsu, P., et al, Nat Biotechnol doi:10.1038/nbt.2647 (2013); Ran, F A., et al, Nature Protocols November; 8(11):2281-308. (2013); Shalem, O., et al., Science December 12. (2013). [Epub ahead of print]; Nishimasu, H., et al, Cell Feb. 27. (2014). 156(5):935-49;

Wu X., et al, Nat Biotechnol. (2014) Apr. 20. doi: 10.1038/nbt.2889; Platt et al., Cell 159(2): 440-455 (2014) DOI: 10.1016/j.cell.2014.09.014; Hsu et al. Cell 157, 1262-1278 (Jun. 5, 2014) (2014); Wang et al., Science. 2014 Jan. 3; 343(6166): 80-84. doi: 10.1126/science. 1246981; Doench et al., Nature Biotechnology published online 3 Sep. 2014; doi:10.1038/nbt.3026; Swiech et al, Nature Biotechnology; published online 19 Oct. 2014; doi:10.1038/nbt.3055), and Targeted Genome Editing Using Site-Specific Nucleases, ZFNs, TALENs, and the CRISPR/Cas9 system, Takashi Yamamoto (ed.). 2015, Springer, ISBN 978-4-431-55226-0 (hbk/ebk). and Zetche et al, Cell, Volume 163, Issue 3, Oct. 22, 2015, p. 759-771.

CRISPR systems also include the systems developed by Editas Medicine (Cambridge, Mass.), Caribou Biosciences (Berkeley, Calif.), CRISPR Therapeutics (Basel, Switzerland), and Intellia Therapeutics (Cambridge, Mass.).

"DNA end resection" generally refers to nucleolytic degradation of the 5'-terminated strand of a DNA double-stranded break leading to the formation of 3'-terminated single-stranded DNA. DNA end resection in eukaryotes comprises two phases: a slow initial phase (catalyzed by the Mre11-Rad50-Nbs1 (MRN) complex in mammals), and a second and faster phase catalyzed by the exonuclease Exo 1 or the helicase Bloom Syndrome Protein (BLM). DNA end resection is initiated by a cell cycle activation step comprising phosphorylation of the accessory protein CtIP. Pathways involved in DNA end resection may be activated by blocking BRCA1 recruitment to DNA double-strand breaks by inhibiting TP53BP1 (53BP1), or blocking recruitment of 53BP1 to DNA double-stranded break sites. In an aspect, DNA end resection may be activated by inhibiting 53BP1 expression or activity and expressing a mutated form of CtIP that mimics constitutive phosphorylation, for example CtIP-Thr879Glu.

"Homologous recombination" and "HR" refer to a type of genetic recombination in which DNA strands of similar or identical nucleotide sequences are exchanged. HR can be used by cells to repair DNA double-strand breaks (DSB) by the following general steps. HR is initiated when the DSB is resected by nucleases and helicases, generating 3' single-stranded DNA (ssDNA) overhangs onto which the RAD51 recombinase assembles as a nucleoprotein filament. This structure can invade homologous duplex DNA, which is used as a template for repair DNA synthesis. The resulting intermediates can be differentially metabolized to produce crossover or non-crossover products (San Filippo et al., Annu. Rev. Biochem. 2008. 77:229-57). Following a double-strand break, sections around the 5' ends of the break are resected by nucleases and helicases to generate 3' single-stranded DNA overhangs onto which RAD51 recombinase assembles as a nucleoprotein filament. This structure then invades homologous duplex DNA which is used as a template for DNA repair synthesis. The resulting intermediates can be metabolized to yield non-crossover products thereby restoring the damaged DNA molecule as it existed before the double-strand break. The terms also include recombination using single-stranded oligonucleotides (ssODNs), in particular recombination using single-stranded oligonucleotides (ssODNs) requiring resection and which may be activated by 53BP1 inhibitors.

"HR Disease" refers to any disorder, disease, condition, syndrome or combination of manifestations or symptoms recognized or diagnosed as a disorder which may be associated with or characterized by a HR defect. Exemplary diseases include, for example, cancer, cardiovascular diseases including heart failure, hypertension and atherosclerosis, respiratory diseases, renal diseases, gastrointestinal diseases including inflammatory bowel diseases such as Crohn's disease and ulcerative colitis, hepatic, gallbladder and bile duct diseases, including hepatitis and cirrhosis, hematologic diseases, metabolic diseases, endocrine and reproductive diseases, including diabetes, bone and bone mineral metabolism diseases, immune system diseases including autoimmune diseases such as rheumatoid arthritis, lupus erythematosus, and other autoimmune diseases, musculoskeletal and connective tissue diseases, including arthritis, achondroplasia, infectious diseases and neurological diseases such as Alzheimer's disease, Huntington's disease and Parkinson's disease.

Embodiments of the disclosure provide for treatment of various cancers including but not limited to carcinomas, melanomas, lymphomas, sarcomas, blastomas, leukemias, myelomas, osteosarcomas, neural tumors, and cancer of organs such as the breast, ovary, and prostate.

In embodiments, treatment of cancer with BRCA-1 defects, BRCA-2 defects, dual BRCA-1/BRCA-2 defects, and Fanconi anemia is provided. In some embodiments, the cancer is breast cancer, in particular invasive ductal carcinoma and invasive lobular carcinoma. In some embodiments, the cancer is ovarian cancer, in particular epithelial ovarian tumors, germ cell ovarian tumors, and sex cord stromal tumors.

Methods disclosed herein for activating homologous recombination may be used to genetically modify polynucleotides associated with a genetic disorder. In some embodiments, the genetic disorder is a monogenetic disorder. In some embodiments, the genetic disorder is a multigenetic disorder. In some embodiments, the genetic disorder is associated with one or more SNPs. In particular embodiments, the genomic modification corrects a point mutation.

Examples of genetic disorders and polynucleotide sequences associated with the genetic disorders may be found on the World Wide Web (see for example, the National Center for Biotechnology Information, National Library of Medicine (Bethesda, Mass.) or the McKusick-Nathans Institute of Genetic Medicine, Johns Hopkins University (Baltimore, Md.), listed in published patents and applications (see, for example, US Published Application No. 2015/0247150), and in publications (see for example, Turitz Cox D. B. et al, Nature Medicine 21, 121-131, 2015; and O'Connor T. P. and R. G. Crystal, Nature Reviews/Genetics Volume 7, April 2006, pages 261-276 including Supplementary Information, and publications cited therein.)

In an aspect, the genetic disorder is a genetic disorder of muscle. In an aspect, the genetic disorder is myotonic dystrophy type 1. In an aspect, the genetic disorder is myotonic dystrophy type 2. In an aspect, the genetic disorder is Duchenne muscular dystrophy (DMD). In an aspect, the genetic disorder is Becker muscular dystrophy.

In an aspect, the genetic disorder is a genetic disorder of the liver, for example, alpha-1 antitrypsin deficiency, Wilson Disease, hereditary hemochromatosis, Type I tyrosinemia, glycogen storage disease Type IV, argininosuccinate lyase deficiency, citrin deficiency, cholesterol ester storage disease and hereditary fructose intolerance.

In an aspect, the genetic disorder is alpha-1 antitrypsin deficiency which is an autosomal recessive (codominant) disease due to mutations in the SERPINA1 gene that encodes the serine protease inhibitor AAT.

In an aspect, the genetic disorder is Wilson disease which depends on mutations in the gene encoding the ATP7B Cu translocase, a protein mainly expressed by the hepatocyte that regulates the levels of copper in the liver.

In an aspect, the genetic disorder is a genetic disorder of the lungs.

In an aspect, the genetic disorder is cystic fibrosis, an autosomal recessive disease caused by mutations of the Cystic Fibrosis Transmembrane Regulator (CFTR) protein, a member of the ATP-binding cassette superfamily of transmembrane proteins.

In other aspects, the genetic disorder may be heamophilia, α1-antitrypsin deficiency, Canavan disease, Adenosine deaminase deficiency, X-linked severe combined immunodeficiency, familial amyloidotic polyneuropathy, thalassemia, Tay-Sachs disease, late infantile ceroid lipofuscinosis, mucopolysaccharidosis, Niemann-Pick disease, achondroplasia, Huntington disease, spino-cerebellar ataxia, Fredriech ataxia, Amyotrophic Lateral Sclerosis, monogenic hypercholesterolemia and other monogenic disorders.

In aspects, the genetic disorder is sickle cell anemia and a method disclosed herein comprises correcting the mutated HBB hemoglobin gene by gene conversion with its paralog HBD.

An "effective amount" refers to an amount of a compound or composition, as disclosed herein effective to achieve a particular biological result. Such results include, without limitation, the treatment of a disease or condition disclosed herein as determined by any means suitable in the art.

A "composition" refers to a mixture of at least one polypeptide and/or polynucleotide disclosed herein with other chemical components, such as carriers, stabilizers, diluents, dispersing agents, suspending agents, thickening agents, and/or excipients. A composition facilitates administration of the compound to a cell or organism. Multiple techniques of administering a compound exist in the art including, but not limited to, intravenous, oral, aerosol, parenteral, ophthalmic, pulmonary and topical administration. Guidance for preparing pharmaceutical compositions may be found, for example, in Remington: The Science and Practice of Pharmacy, (20th ed.) ed. A. R. Gennaro A. R., 2000, Lippencott Williams & Wilkins.

The term "salt" includes addition salts of free acids or free bases that are compounds useful within the invention. Suitable acid addition salts may be prepared from an inorganic acid or from an organic acid. Examples of inorganic acids include hydrochloric, hydrobromic, nitric, sulfuric and phosphoric acids. Examples of organic acids include aliphatic, cycloaliphatic, aromatic, araliphatic, heterocyclic, carboxylic and sulfonic classes such as formic, acetic, propionic, succinic, glycolic, gluconic, lactic, malic, tartaric, citric, ascorbic, gluouronic, maleic, fumaric, pyruvic, aspartic, glutamic, benzoic, tearic, alginic, salicylic, galactaric and galacturonic acid. Base addition salts include, for example, metallic salts including alkali metal, alkaline earth metal and transition metal salts such as, for example, lithium, calcium, magnesium, potassium, sodium and zinc salts. Salts may be prepared by conventional means from the corresponding free base compound by reacting, for example, the appropriate acid or base with the corresponding free base. Further examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

The term "solvate" includes complexes of the polypeptides or salts thereof disclosed herein with solvent molecules, e.g. organic solvent molecules and/or water.

The terms "subject", "individual" or "patient" refer, interchangeably, to a warm-blooded animal such as a mammal. In particular, the term refers to a human. A subject, individual or patient may be afflicted with or suspected of having or being pre-disposed to a disease as described herein. The term also includes animals bred for food, as pets, or for study including horses, cows, sheep, poultry, fish, pigs, cats, dogs, and zoo animals, goats, apes (e.g. gorilla or chimpanzee), and rodents such as rats and mice.

ASPECTS OF THE DISCLOSURE

Modified Polypeptides

Modifications of polypeptides as contemplated by the disclosure include substitutions of amino acids, insertions, deletions or chemical modifications. Techniques known per se for the modification of one or more amino acids are available to those skilled in the art (see for example, Ausubel et al., 1987, as well as Sambrook et al., 1989). In particular aspects, amino acid modifications can be selected by means of computational analysis based on the structural data for the complexes of the polypeptides and the 53BP1 tandem Tudor domain (residues 1784-1603) described herein [32]. Pro-SAII software ("Protein Structure Analysis"; Proceryon Biosciences, Salzburg) may also be used to determine protein stability for the polypeptides. In aspects, the modifications are substitutions of amino acids.

A modified polypeptide of the disclosure may be identified by its affinity to the 53BP1 Tudor domain (residues 1784-1603). Affinity for the 53BP1 Tudor domain may be determined by suitable assays known to those skilled in the art. Affinity may also be determined by assessing 53BP1 recruitment to DSB sites as described in the Examples herein. In an aspect, a polypeptide disclosed herein has a quantifiable binding affinity to the 53BP1 Tudor domain of 0.5 to $15 \times 10^{-9}$M, 0.5 to $25 \times 10^{-9}$M, 0.5 to $50 \times 10^{-9}$M, 0.5 to $100 \times 10^{-9}$M, 0.5 to $200 \times 10^{-9}$M, 1 to $200 \times 10^{-9}$M, 1 to $300 \times 10^{-9}$M, 1 to $400 \times 10^{-9}$M, 1 to $500 \times 10^{-9}$M, 100 to $300 \times 10^{-9}$M, 100 to $250 \times 10^{-9}$M, or 200 to $250 \times 10^{-9}$M.

A polypeptide disclosed herein may be prepared, and purified by means of genetic engineering methods or synthetic approaches known to those skilled in the art and described in the literature (e.g. Sambrook et al., 2001; Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). For example, targeted mutagenesis using PCR, chemical mutagenesis or bacterial mutator strains may be used to generate the modified polypeptides. In aspects, the polypeptides may be produced in a prokaryotic host or eukaryotic or cell-free systems. After insertion of a DNA sequence encoding the polypeptides into a suitable expression vector and transformation, transfection or infection of appropriate organisms the polypeptide is synthesized by the transcription/translation system. Alternatively, the gene expression can be achieved without utilizing a cell system. Another way of preparing a polypeptide disclosed herein is the synthesis in solution or on a solid support and subsequent isolation and purification. Genetic engineering and synthetic methods may also be combined in any way.

A polypeptide particularly described herein may be further modified by targeted and/or random modifications to enhance their affinity, specificity stability, solubility and production level in host cells. In an aspect, the polypeptides disclosed may have unmodified side-chains or carry at least one chemical modification at one or more side chains.

The disclosure also includes polypeptides comprising amino acid sequences and polynucleotides that are at least about 50%, 60%, 70% or 80% identical, more preferably at least about 90% identical and most preferably at least about 95% identical (e.g., 95%, 96%, 97%, 98%, 99%, 100%) to any of the referenced sequences herein (e.g., SEQ ID NO: 1) when the comparison is performed by a BLAST algorithm wherein the parameters of the algorithm are selected to give the largest match between the respective sequences over the entire length of the respective reference sequences. In an aspect, the disclosure comprises polypeptide amino acid sequences or nucleic acid sequences that are at least about 70% or 80% similar, more preferably at least about 90% similar and most preferably at least about 95% similar (e.g., 95%, 96%, 97%, 98%, 99%, 100%) to any of the referenced sequences when the comparison is performed with a BLAST algorithm wherein the parameters of the algorithm are selected to give the largest match between the respective sequences over the entire length of the respective reference sequences. BLAST algorithms often used for sequence analysis are well known in the art, including those described in Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; and Hancock, J. M. et al., (1994) Comput. Appl. Biosci. 10:67-70.

The disclosure also provides fragments and fusion proteins of polypeptides disclosed herein with the proviso that they bind the 53BP1 tandem Tudor domain.

A polypeptide fragment includes a portion of a polypeptide having a region that is substantially identical to a portion of a polypeptide disclosed herein and retains at least 60%, 70% or 80%, more preferably 90%, or 95%, or even 99% of at least one biological activity of the polypeptide, but does not include the entire amino acid or nucleic acid sequence of the polypeptide. For example, the fragment may have at least 1, at least 5, at least 10, 15, 20, 30, or 40 fewer amino acid residues or nucleic acid bases relative to the full-length modified polypeptides disclosed herein.

Additional amino acids or peptides or substitutions of individual amino acids or peptides may be introduced (in particular at the amino and/or carboxy termini) to obtain fusion proteins by chemical coupling with suitable reagents. Fusion polypeptides may also be prepared by genetic engineering by linking the gene of polypeptide disclosed herein to that of the fusion partner. Bivalent or bispecific polypeptides may be obtained by linking (for example, via an additionally introduced cysteine or positively or negatively charged amino acids at the carboxy terminal ends of the fusion partners) a polypeptide disclosed herein to a polypeptide of the same or a different specificity in a site-specific and covalent manner.

Polypeptides disclosed herein may be coupled to (reporter) enzymes, toxins or other binding proteins, for example, biotin, digoxigenin, GFP, Flag, and fluorescent and/or luminescent substances.

The present disclosure also provides an antibody or antisera specifically immunoreactive with a polypeptide disclosed herein.

In another aspect, a polynucleotide encoding any of the disclosed polypeptides is provided. In an embodiment, the polynucleotide is DNA. In another embodiment, the polynucleotide is RNA. In another embodiment, the polynucleotide is mRNA. Examples of polynucleotides of the present disclosure are the sequences in Table 3 (SEQ ID NO: 12 to 25, 49 and 50). In a particular embodiment, the polynucleotide comprises the nucleic acid sequence of SEQ ID NO: 24 or 25.

Also provided are vectors containing such polynucleotides, including prokaryotic vectors, viral vectors, or eukaryotic vectors, such as mammalian vectors. Exemplary viral vectors include adenovirus, adeno-associated-virus, retrovirus, herpes virus, lentivirus, poxvirus, and cytomegalovirus. Provided in the disclosure are cells containing these vectors, including eukaryotic cells, such as mammalian cells. In some aspects, the cells express a polypeptide disclosed herein. Thus, also provided herein are polypeptides that are produced by these cells. As will be appreciated by those skilled in the art, nucleic acid sequences encoding polypeptides disclosed herein might be altered (e.g., without changing the amino acid sequence of the polypeptide) for enhancing delivery or production of the polypeptide in certain expression systems or cells (e.g., intron elimination and/or codon optimization for a given expression system). Codon optimization tools, algorithms and services are known in the art, including without limitation, services from GeneArt (Life Technologies), DNA2.0 (Menlo Park Calif.) and/or proprietary methods.

In an embodiment, an isolated cell or cell lines are provided comprising any of the polypeptides and/or polynucleotides disclosed herein. Cells or cell lines may comprise one or more transcribed and/or translated exogenous sequences that have been stably or transiently introduced into the cells. Examples of cells include bacterial cells such as *E. coli* cells, insect cells, yeast cells, or mammalian cells.

The present disclosure also features a method of producing a polypeptide disclosed herein by culturing the cells in a medium under conditions permitting expression of a polypeptide encoded by the polynucleotide, and purifying the polypeptide from the cultured cell or the medium of the cell.

In aspects of the disclosure, transgenic organisms are provided carrying one or more sequences encoding polypeptides as disclosed herein and/or one or more exogenous sequences (e.g., sequences inserted into the genome via targeted integration). For example, transgenic organisms are contemplated comprising polynucleotides as disclosed herein under the control of an inducible promoter. Transgenic organisms as disclosed herein may be plants (e.g. crop plants or tobacco strains) or animals (e.g. mice, rats, rabbits, fish, etc.). Exogenous sequences may comprise, for example, one or more genes or cDNA molecules, or any type of coding or noncoding sequence, as well as one or more control elements (e.g., promoters). An exogenous sequence may produce one or more RNA molecules (e.g., small hairpin RNAs (shRNAs), inhibitory RNAs (RNAis), microRNAs (miRNAs), etc.).

Methods

The polypeptides and/or polynucleotide of the present disclosure may be used in a broad spectrum of applications. The polypeptides and/or polynucleotide may be used for the detection and quantitative determination as well as for the separation and isolation of 53BP1. The present disclosure also provides the use of polypeptides and/or polynucleotides disclosed herein for use as medicaments, particularly for the treatment of an HR Disease as described herein.

The polypeptides and polynucleotides disclosed herein may be used in genomic engineering, epigenomic engineering, genome targeting, and genome editing. The polypeptides and polynucleotides disclosed herein may be used to modify repair pathways, activate or stimulate HR or homology-based genome editing, inhibit 53BP1 recruitment to DSB sites or damaged chromatin in a cell or modulate DNA end resection. In an aspect, the polypeptides and polynucleotides disclosed herein are used in combination with a gene editing system. In embodiments, the polypeptide and/or polynucleotide is administered in combination with one or more elements or components of a CRISPR system. In embodiments, the polypeptide and/or polynucleotide is administered before, simultaneously or after one or more elements or components of a CRISPR system. In embodiments, the polypeptide and/or polynucleotide is administered before, simultaneously or after one or more elements or components of a CRISPR/Cas system. In embodiments, the polypeptide and/or polynucleotide is administered before, simultaneously or after one or more elements or components of a CRISPR/Cpf1 system.

In an aspect, a method of manipulating a DSB repair pathway in a cell during a genome engineering reaction is provided comprising administering to the cell a polypeptide and/or polynucleotide disclosed herein.

In an aspect, a method of stimulating homology-directed repair of DSBs in a cell is provided comprising administering to the cell a polypeptide and/or polynucleotide disclosed herein.

In an aspect, a method of suppressing 53BP1 recruitment to DSB sites in a cell is provided comprising administering to the cell a polypeptide and/or polynucleotide disclosed herein. The suppression of 53BP1 recruitment to DSB sites by the polypeptide may be monitored by methods known in the art such as ionizing radiation focus formation.

In an aspect, a method of inhibiting 53BP1 recruitment to damaged chromatin in a cell is provided comprising administering to the cell a polypeptide and/or polynucleotide disclosed herein.

In an aspect, a method of inhibiting 53BP1 function in a cell is provided comprising administering to the cell a polypeptide and/or polynucleotide disclosed herein.

In an aspect, a method of increasing HR in a cell is provided comprising administering to the cell a polypeptide and/or polynucleotide disclosed herein.

In an aspect, a method of inducing DNA end resection in a cell is provided comprising administering to the cell a polypeptide and/or polynucleotide disclosed herein.

In an aspect, a method of inducing BRCA1 recruitment to DSB sites in a cell is provided comprising administering to the cell a polypeptide and/or polynucleotide disclosed herein.

In an aspect, a method of inhibiting 53BP1 function to DSB sites in a cell thereby increasing HR is provided comprising administering to the cell a polypeptide and/or polynucleotide disclosed herein.

In an aspect, a method of inducing gene conversion in a cell is provided comprising administering to the cell a polypeptide and/or polynucleotide disclosed herein.

The present disclosure provides a method for activating homologous recombination in a cell comprising administering to the cell a polypeptide and/or polynucleotide disclosed herein, optionally in combination with one or more of the following: (a) promoting or stimulating the assembly or occurrence of BRCA1-PALB2 or BRCA1-PALB2-BRCA2 complexes in the cell; (b) inhibiting KEAP1 or CRL3-KEAP1; (b) blocking the degradation of USP11 or promoting or stimulating USP11 activity; (c) administering USP11 or an agonist thereof; and/or (d) inhibiting CRL-KEAP1 and blocking the degradation of USP11.

In an embodiment, a polypeptide and/or polynucleotide disclosed herein is administered in combination with USP11 or an agonist of USP11. In an embodiment, a polypeptide and/or polynucleotide disclosed herein is administered in combination with an inhibitor of CRL3-KEAP1. In an embodiment, a polypeptide and/or polynucleotide disclosed herein is administered in combination with an inhibitor of KEAP1. Examples of inhibitors of KEAP1 include the monobody that is a potent competitive inhibitor of the KEAP1-NRF2 interaction disclosed in Guntas, G. et al, Protein Eng Des Sel. 2015, Oct 20. pii: gzv055, and the KEAP1 inhibitors described in Canning P. et al, Acta Pharm Sin B., 2015 (4):285-99 and Wells, G., Biochem Soc Trans. 2015,43(4): 674-9.

In an aspect, a method of increasing the efficiency of gene targeting in a cell stimulated by a CRISPR system is provided comprising administering to the cell a polypeptide and/or polynucleotide disclosed herein.

In an aspect, a method of increasing gene targeting in a cell is provided comprising administering to the cell a polypeptide and/or polynucleotide disclosed herein in combination with an inhibitor of DNA-PK.

In an aspect, a method of modulating DNA end resection in a cell is provided comprising administering to the cell a polypeptide and/or polynucleotide disclosed herein in combination with an inhibitor of DNA-PK.

In an aspect, the DNA-PK inhibitor is NU7441 [8-dibenzothiophen-4-yl-2-morpholin-4-yl-chromen-4-one, also known as KU-57788; Leahy J J, et al. Bioorg Med Chem Lett, 2004, 14(24), 6083-608]; KU-0060648 (Munck J M, et al. Mol Cancer Ther, 2012, 11(8), 1789-1798); NU7026 (Willmore E, et al. Blood, 2004, 103(12), 4659-466); or PIK-75 (WO/2003/072557, Sep. 4, 2003).

In aspects, methods of the disclosure are used to treat a cell in G1 phase of the cell cycle (G1) or G0 phase of the cell cycle.

In aspects, a method of stimulating HR in a non-dividing cell is provided comprising administering to the cell a polypeptide and/or polynucleotide disclosed herein.

In other aspects, methods of the present disclosure are administered to, or used to treat, a cell comprising engineered DSBs for genome modification or gene editing purposes.

The present disclosure also contemplates the use of methods, compositions and kits disclosed herein in genome modification, provided that said use is not a method for treatment of the human or animal body by surgery or therapy, and provided that said use is not a process for modifying the germ line genetic identity of human beings. Genome modification may comprise modifying a target polynucleotide sequence in a cell, modifying expression of a polynucleotide sequence in a cell, generating a model cell comprising a mutated disease gene, or knocking out a gene. A use of the present disclosure may further comprise repairing or editing a cleaved target polynucleotide by inserting an exogenous template polynucleotide, wherein the repair or editing results in a mutation comprising an insertion, deletion, or substitution of one or more nucleotides of the target polynucleotide.

Also contemplated herein is the use of methods, compositions and kits disclosed herein in genome engineering, provided that said use is not a method for treatment of the human or animal body by surgery or therapy, and provided that said use is not a process for modifying the germ line genetic identity of human beings. Genome engineering may comprise modifying a target polynucleotide sequence in a cell, modifying expression of a polynucleotide sequence in a cell, generating a model cell comprising a mutated disease gene, or knocking out a gene. A use of the disclosure may further comprise repairing or editing a cleaved target polynucleotide by inserting an exogenous template polynucleotide, wherein said repair results in a mutation comprising an insertion, deletion, or substitution of one or more nucleotides of said target polynucleotide.

A method of homology directed repair in a cell of engineered DSBs for genome modification purposes is provided comprising administering to the cell a polypeptide and/or polynucleotide disclosed herein.

The disclosure relates to the use of a polypeptide and/or polynucleotide disclosed herein in homology directed repair of engineered DSBs for genome modification purposes.

The disclosure relates to the use of a polypeptide and/or polynucleotide disclosed herein in homology-directed repair with single-stranded oligonucleotides (ssODNs).

The disclosure also relates to the use of a polypeptide and/or polynucleotide disclosed herein for stimulating homology-directed repair with single-stranded oligonucleotides (ssODNs).

In an aspect, a method disclosed herein for activating or stimulating HR in a cell further comprises a gene editing system. In an aspect the gene editing system comprises contacting the cell with a nuclease. Examples of nucleases include without limitation, zinc finger nucleases (ZFNs), engineered meganucleases, transcription activator like effector nucleases (TALENs), mega or homing endonucleases, clustered regularly interspaced short palindromic repeats (CRISPR)-associated (Cas) nucleases, Cpf1 nucleases, Ttago nucleases, and fusions between nucleases, such as mega-TALs and compact TALENs. In an aspect, the gene editing steps comprise the CRISPR/Cas9 system. In an aspect, the gene editing steps comprise the CRISPR/Cpf-system.

A method of stimulating homology-based genome editing in a cell is provided comprising administering to the cell a polypeptide disclosed herein.

In aspects, a gene editing system may correct a genomic modification. A genetic modification may comprise at least one mutation in a polynucleotide sequence having a locus associated with a genetic disorder, in particular a HR disease. In an aspect, the genomic modification is selected from the group consisting of insertions, deletions and combinations thereof. In some embodiments, the genetic disorder is a monogenetic disorder. In some embodiments, the disorder is a multigenetic disorder. In some embodiments, the disorder is associated with one or more SNPs. In particular embodiments, the genomic modification corrects a point mutation.

In an aspect of a method of the disclosure to correct a genomic modification, the gene editing system comprises contacting the cell with a clustered regularly interspaced short palindromic repeats (CRISPR)-associated (Cas) protein and from one to two ribonucleic acids, wherein the ribonucleic acids direct Cas protein to, and hybridize to, a selected motif of a target polynucleotide sequence associated with a genetic disorder, wherein the target polynucleotide sequence is cleaved.

A method for altering a genetic disorder associated with a target polynucleotide sequence in a cell is provided comprising: (1) contacting the cell with a system which activates homologous recombination in the cell wherein the system comprises a polypeptide and/or polynucleotide disclosed herein and optionally BRCA1-PALB2 or BRCA1-PALB2-BRCA2 or agents that maintain the BRCA1-PALB2 or BRCA1-PALB2-BRCA2 interactions throughout the cell cycle; and (2) contacting the target polynucleotide sequence with a clustered regularly interspaced short palindromic repeats-associated (Cas) protein and from one to two ribonucleic acids, wherein the ribonucleic acids direct Cas protein to and hybridize to a selected motif of the target polynucleotide sequence, wherein the target polynucleotide sequence is cleaved. The method may reduce expression of the target polynucleotide sequence, knock out the target polynucleotide sequence, or correct the target polynucleotide sequence from an undesired sequence to a desired sequence. In an aspect of the method, the cell is in G1 phase of the cell cycle (G1) or G0 phase of the cell cycle. In an aspect of the method, the Cas protein is replaced with a Cpf1 protein.

A method for treating or preventing a genetic disorder in a subject is contemplated, the method comprising altering a target polynucleotide sequence associated with the genetic disorder in a cell by contacting the cell with a system which activates homologous recombination in the cell wherein the system comprises a polypeptide and/or polynucleotide disclosed herein and optionally BRCA1-PALB2 or BRCA1-PALB2-BRCA2 or agents that maintain the BRCA1-PALB2 or BRCA1-PALB2-BRCA2 interactions throughout the cell cycle; and contacting the target polynucleotide sequence with a CRISPR system so that the target polynucleotide sequence is cleaved, thereby treating or preventing the genetic disorder. In an aspect, a method for treating or preventing a genetic disorder in a subject is provided, the method comprising altering a target polynucleotide sequence associated with the genetic disorder in a cell by contacting the cell with a system which activates homologous recombination in the cell wherein the system comprises a polypeptide and/or polynucleotide disclosed herein and optionally BRCA1-PALB2 or BRCA1-PALB2-BRCA2 or agents that maintain the BRCA1-PALB2 or BRCA1-PALB2-BRCA2 interactions throughout the cell cycle; and contacting the target polynucleotide sequence with a clustered regularly interspaced short palindromic repeats-associated (Cas) protein and from one to two ribonucleic acids, wherein the ribonucleic acids direct Cas protein to and hybridize to a selected motif of the target polynucleotide sequence, wherein the target polynucleotide sequence is cleaved, thereby treating or preventing the genetic disorder. The method may comprise introducing the cell into the subject, thereby treating or preventing the genetic disorder associated with the target polynucleotide sequence. The method may comprise repairing the cleaved target polynucleotide sequence by inserting an exogenous template polynucleotide, wherein said repair results in a mutation comprising an insertion, deletion, or substitution of one or more nucleotides of said target polynucleotide sequence. In an aspect of the method, the cell is in G1 phase of the cell cycle (G1) or G0 phase of the cell cycle.

In an aspect, the target polynucleotide sequence is associated with a genetic disorder of the lung. In an embodiment the target polynucleotide sequence is associated with cystic fibrosis, in particular the polynucleotide sequence is the cystic fibrosis transmembrane conductor receptor (CFTR) locus. Mutations in the CFTR (e.g., deletion of phenylalanine at position 508 in exon 11) cause cystic fibrosis.

In an aspect, the target polynucleotide sequence is associated with a genetic disorder of muscle. In an aspect, the target polynucleotide sequence is associated with muscular dystrophies. In an aspect, the target polynucleotide sequence is associated with Duchenne muscular dystrophy (DMD) (mutations in the dystrophin gene). In an aspect, the target polynucleotide sequence is associated with Becker muscular dystrophy (mutations in the dystrophin gene). In an aspect the target polynucleotide is associated with myotonic dystrophy type 1 (mutations in the DMPK gene) or myotonic dystrophy type 2 (mutations in the CNBP gene).

In an aspect, the target polynucleotide sequence is associated with sickle cell anemia (mutated HBB hemoglobin).

In aspects, the targeted polynucleotide sequence is associated with a genetic disorder of the liver. In an aspect, the target polynucleotide sequence is associated with alpha-1 antitrypsin deficiency (mutations in the SERPINA1 gene). In an aspect, the targeted polynucleotide sequence is associated with Wilson disease (mutations in the gene encoding the ATP7B Cu translocase).

In an aspect, the methods of the disclosure further comprise providing a functional protein with enhanced characteristics as compared to its naturally occurring counterpart, in particular a functional protein lacking or deficient in a subject, for example for treating genetic disorders. In embodiments, the methods comprise integrating a sequence encoding a functional protein in a cell in a subject in need thereof by sequential administration of a gene editing system and one or more transgene(s) encoding a non-naturally occurring protein with enhanced properties as compared to its naturally occurring counterpart. In other embodiments, the methods comprise administering to the subject a genetically modified cell expressing a functional version of one or more proteins aberrantly expressed in a subject. Thus, an isolated cell may be introduced into the subject (ex vivo cell therapy) or a cell may be modified when it is part of the subject (in vivo). In certain embodiments, transgene(s) are delivered using a viral vector, a non-viral vector and/or combinations thereof.

Components of the methods of the disclosure may be delivered by delivery systems known in the art, including without limitation viral based systems or non-viral based systems. (See for example, Sambrook et al, supra; Findeis, Mark A., editor, Nonviral vectors for gene therapy: methods and protocols (Totowa, N.J.: Humana Press, c2001); Rolland, Alain and Sullivan, Sean M., editors, Pharmaceutical gene delivery systems (New York : Marcel Decker, c2003); Rolland, Alain, editor, Advanced gene delivery: from concepts to pharmaceutical products (Amsterdam: Harwood Academic, c1999); K. Kataoka, Taira, K., Niidome, T. editors, Non-viral gene therapy: gene design and delivery (Tokyo; New York: Springer, c2005); and S. Lasic, Danilo D., Liposomes in gene delivery (Boca Raton, Fla.: CRC Press, 1997).)

Conventional viral based systems may comprise, for example, retroviral, lentivirus, adenoviral, adeno-associated, SV40, polyoma, papilloma, picornavirus, pox, helper-dependent adenoviral, and herpes simplex virus vectors for gene transfer. In an aspect the viral based system, is an adenoviral vector or adeno-associated viral vector. Suitable plasmid expression vectors can also be used. Examples of plasmid expression vectors include, without limitation, commercially available expression vectors from Novagen (e.g., pET vectors, Rosetta™ (D3), Origami™ (DE3)), New England Labs, Inc (e..g., pMAL™ vectors), Invitrogen Inc. (e.g., pAd/CMV/VS-DEST™, pAd-DEST™ vector, pLenti4/V5-DEST™) and Clontech (e.g., pAdeno X™ and pAd5F35).

Examples, of non-viral based systems include lipofection, nucleofection, electroporation, microinjection, sonoporation, biolistics, virosomes, liposomes, immunoliposomes, polycation or lipid: nucleic acid conjugates, naked DNA, mRNA, nanomaterial-based delivery, artificial virons and agent-enhanced uptake of DNA.

In an aspect, the component is a polypeptide disclosed herein and it is delivered into a cell by electroporation, sonoporation, microinjection, liposomal delivery or nanomaterial-based delivery.

In an aspect, the component is a polynucleotide disclosed herein and it is delivered into a cell using a vector such as an adenovirus vector, retrovirus vector, adeno-associated virus vector, lentiviral vector, herpes virus vector, SV 40 vector, polyoma virus vector, papilloma virus vector, picornavirus vector, pox virus vector, or a helper-dependent adenovirus vector.

In an aspect, one or more vector is provided comprising activators of DNA end-resection and activators of homologous recombination discussed herein. In an aspect, one or more vector (e.g. viral vector) is provided comprising a polynucleotide encoding a polypeptide disclosed herein and optionally one or more of the following elements or components: 1) another activator of DNA end-resection, for example, an inhibitor of RIF expression or activity and/or a CtIP compound that mimics constitutive phosphorylation; 2) other factors that activate homologous recombination, for example, factors that maintain BRCA 1-PALB2 or BRCA 1-PALB2-BRCA2 interactions during the cell cycle; and, optionally, 3) one or more elements or components of a gene editing system, in particular components of a CRISPR system.

Examples of other activators of DNA end-resection include, without limitation, the coding sequence of CtIP-Thr847Glu, a shRNA against the TP53BP1 mRNA, and a shRNA against KEAP1. The shRNA against TP53BP1 may be substituted with a shRNA against RIF1 or agents that block 53BP1 recruitment to DSB sites including a dominant-negative 53BP1 protein. The shRNA against KEAP1 may be substituted with a coding sequence of a PALB2 mutant that contains mutations of its Lys20, Lys25 and Lys30 residues or that contains a mutation that disrupts its interaction with KEAP1 (see Orthwein, A. et al. *Nature* 528, 422-426 (2015)).

Examples of factors that maintain BRCA1-PALB2 or BRCA1-PALB2-BRCA2 interactions during the cell cycle include without limitation, inhibitors of KEAP1, inhibitors of DCAF10, RNA interference agents that maintain USP11 expression in G0 and G1 cells or a mutated form of PALB2 that is insensitive to ubiquitylation by KEAP1-CUL3-RBX1 which may involves the mutation of one or more of the Lys20, Lys25 or Lys30 residues. An example of a KEAP1 inhibitor is the monobody that is a potent competitive inhibitor of the KEAP1-NRF2 interaction disclosed in Guntas, G. et al, (Protein Eng Des Sel. 2015, Oct 20. pii: gzv05). KEAP1 inhibitors are also described, for example in Canning P. et al, Acta Pharm Sin B., 2015 (4):285-99 and Wells, G., Biochem Soc Trans. 2015,43(4): 674-9.

Kits

The disclosure further provides a kit for performing an assay or method disclosed herein. In an aspect, a kit is provided comprising one or more of components of a method of the invention for activating homologous recombination and optionally components of a gene editing system. The kit may also include or be used in combination with components of a CRISPR system. The kit may also include or be used in combination with components of a TALEN system.

In an embodiment, the kit comprises a polypeptide or polynucleotide disclosed herein and components of a gene editing system. In an embodiment the gene editing system is CRISPR. In an embodiment the gene editing system is a TALEN system.

In some embodiments, a kit comprises a polypeptide disclosed herein and instructions for using the kit. In some embodiments, a kit comprises a vector comprising a polynucleotide disclosed herein and instructions for using the kit. In an aspect, the kit comprises a vector comprising activators of DNA end resection and activators of homologous recombination discussed herein.

In an aspect, the kit comprises a vector (e.g. viral vector) comprising a polynucleotide encoding a polypeptide disclosed herein, and optionally one or more of the following components: 1) another activator of DNA end resection, for example, an inhibitor of RIF expression or activity and/or a CtIP compound that mimics constitutive phosphorylation; 2) other factors that activate homologous recombination, for example, factors that maintain BRCA1-PALB2 interactions during the cell cycle; and, optionally, 3) components of a gene editing system, in particular components of a CRISPR system. In an aspect, a kit is provided comprising a vector disclosed herein and one or more of the following components: 1) an inhibitor of RIF expression or activity or a CtIP compound or analog that mimics constitutive phosphorylation (e.g., CtIP-Thr847Glu or a shRNA against RIF1); 2) factors that maintain BRCA1-PALB2 interactions during the cell cycle; and, 3) components of a gene editing system.

Examples of activators of DNA end-resection include without limitation, the coding sequence of CtIP-Thr847Glu, a shRNA against the TP53BP1 mRNA, and a shRNA against KEAP1. The shRNA against TP53BP1 may be substituted with a shRNA against RIF1 or agents that block 53BP1 recruitment to DSB sites including a dominant-negative 53BP1 protein. The shRNA against KEAP1 may be substituted with a the coding sequence of a PALB2 mutant that contains mutations of its Lys20, Lys25 and Lys30 residues or that contains a mutation that disrupts its interaction with KEAP1 (see Orthwein, A. et al. *Nature* 528, 422-426 (2015)).

Examples of factors that maintain BRCA1-PALB2 interactions during the cell cycle include without limitation, inhibitors of KEAP1, inhibitors of DCAF10, for example, RNA interference agents that maintain USP11 expression in G0 and G1 cells or a mutated form of PALB2 that is insensitive to ubiquitylation by KEAP1-CUL3-RBX1 which involves the mutation of one or more of the Lys20, Lys25 or Lys30 residues. An example of a KEAP1 inhibitor is the monobody that is a potent competitive inhibitor of the KEAP1-NRF2 interaction disclosed in Guntas, G. et al, (Protein Eng Des Sel. 2015, Oct 20. pii: gzv05). KEAP1 inhibitors are also described, for example in Canning P. et al, Acta Pharm Sin B., 2015 (4):285-99 and Wells, G., Biochem Soc Trans. 2015,43(4): 674-9.

In an embodiment, a kit comprises one or more vectors comprising a polynucleotide disclosed herein (in particular SEQ ID NO: 24 or 25), a KEAP1 inhibitor or DCAF10 inhibitor, and an analog of CtIP that mimics constitutive phosphorylation. In an embodiment, a kit of the invention comprises one or more vectors comprising sequences encoding a KEAP1 inhibitor, a polynucleotide disclosed herein (in particular SEQ ID NO: 24 or 25) and CtIP-Thr879Glu. In a particular embodiment, a kit comprises one or more vectors comprising sequences encoding a KEAP1 inhibitor, a polynucleotide disclosed herein (in particular SEQ ID NO: 24 or 25), and CtIP-Thr879Glu. In embodiments, the kits further comprise components of a gene editing system.

The following non-limiting examples are illustrative of the present invention:

EXAMPLE 1

The study described in this Example identified a genetically encoded inhibitor of 53BP1 (TP53BP1), a regulator of DSB repair pathway choice [5].

The following materials and methods were used in the study described in this Example.

Cell Culture and Treatments

U-2-OS (U2OS) and 293T cells were obtained from ATCC. 293T and HEK293 Flp-In/T-REx cells (Invitrogen) were propagated in DMEM medium supplemented with 10% fetal bovine serum (FBS, Gibco) and 2 mM L-alanyl-L-glutamine, and were maintained in a 37° C. and 5% $CO_2$ atmosphere. U2OS cells were grown in McCoy's medium supplemented with 10% FBS. U2OS DR-GFP and EJ2-GFP cells were a gift of Jeremy Stark. 53BP1Δ U2OS and U2OS cell lines stably expressing CtIP-T847E were previously described [4].

RPE1 hTERT cells were obtained from ATTC and maintained in DMEM +10% FCS. A Flag-Cas9-2A-Blast expression cassette was integrated as described before [29]. Upon single clone selection, cells were maintained in the presence of 2 μg/mL blasticidin. The TP53 gene was knocked-out using transient transfection of the LentiGuide plasmid with Lipofectamine. 24 h post-transfection, cells were selected for 24 h with 15 μg/mL puromycin, followed by a 5-day recovery and 48 h selection with 10 μM of the MDM2 inhibitor Nutlin-3 (Cayman Chemical) after which single clones were isolated and verified for loss of p53 protein. Furthermore, CRISPR-generated indel mutations in the TP53 gene were verified by PCR amplification of the region surrounding the single-guide RNA (sgRNA) target sequence, cloning of products into the pCR2.1 TOPO vector (TOPO TA Cloning kit, Thermo Fisher Scientific) and Sanger sequencing of individual bacterial clones (forward PCR-primer: GCATTGAAGTCTCATGGAAGC (SEQ ID NO: 26), reverse PCR-primer: TCACTGCCATGGAGGAGC (SEQ ID NO: 27). 53BP1 and/or BRCA1 gene knockouts were generated by electroporation of the respective LentiGuide vectors (Lonza Amaxa II Nucleofector, program T-023, 5 μg plasmid per 700,000 cells). 24 h post transfection, cells were selected for 24 hr with 15 μg/mL puromycin, followed by single clone isolation. The double 53BP1/BRCA1Δ cell line was created by deleting BRCA1 from the 53BP1 single knock-out cell line. Gene mutations were further confirmed by PCR amplification and sequencing as described above for TP53 (53BP1 forward PCR-primer: CCAGCACCAACAAGAGC (SEQ ID NO: 28), 53BP1 reverse PCR-primer: GGATGCCTGGTACTGTTTGG (SEQ ID NO: 29), BRCA1 forward PCR-primer: TCTCAAAGTATTTCATTTTCTTGGTGCC (SEQ ID NO: 30), BRCA1 reverse PCR-primer: TGAGCAAGGATCATAAAATGTTGG (SEQ ID NO: 31)). Retrovirus of GFP (IRES-GFP), i53-IRES-GFP and DM-IRES-GFP was generated in 293T cells by transient transfection of the pMX-IRES-GFP vector together with the packaging vectors VSVG and Gag-Pol using LT1 transfection reagent (Minis). Supernatants containing retrovirus were collected and filtered through 0.45 μm filters. RPE1 cells were transduced in two hits (24 h apart) to an MOI of approximately 0.8 in the presence of 8 μg/mL polybrene and sorted for GFP 72 h after the second hit. All cells were >97% positive for GFP throughout the experiments, as based on FACS analysis. All cell lines tested negative for mycoplasma contamination and the identity of cell lines confirmed by STR analysis.

Plasmids

The phagemid (DDp2235) from the UbvG08 phage was obtained from the ubiquitin variant library previously described [7]; see below for details. The UbvG08 open reading frame (ORF) lacking the C-terminal di-Gly residues was cloned into a pDONR vector using a product from PCR amplification of the phagemid template and Gateway recombination, yielding plasmid DDp2251 (UbvG08 ΔGG). The pETM-30-2-GST-UbvG08 (DDp2186) and pETM30-2-GST-ubiquitin (DDp2192) were cloned following PCR amplification from the UbvG08ΔGG or UbΔGG ORFs, respectively. The constructs encoding His6-GST-TEV and MBP fusions of 53BP1 Tudor-UDR (residues 1484-1631) and Tudor (residues 1484-1603) domains were described previously [13]. The I44A mutation was introduced into DDp2186, which was then used as a template for amplification of the modified Ubv by PCR. The PCR product was cloned into the BamHI and NotI sites of a pcDNA3-Flag plasmid to yield pcDNA3-Flag-i53 (DDp2534). The BamHI-NotI fragment of DDp2534 was subsequently cloned into a pcDNA5-Flag-FRT/TO Flag vector to yield plasmid DDp2535. All other plasmids were generated by site-directed mutagenesis carried out by Quikchange (Agilent). The lentiviral vector coding for a siRNA-resistant Flag-tagged CtIP T847E construct was previously described [4]. The plasmids used for the LMNA assay were from G. Dellaire [21].

Single-guide RNAs targeting TP53 (CAGAATG-CAAGAAGCCCAGA (SEQ ID NO: 32)), BRCA1 (AAGGGTAGCTGTTAGAAGGC (SEQ ID NO: 33)) and 53BP1 (TCCAATCCTGAACAAACAGC (SEQ ID NO: 34)) were cloned into lentiGuide-Puro (Addgene: #52963) as previously described [30]. The i53 and deficient mutant (DM) lentiviral expression vectors were prepared by PCR amplification that also introduced sequences coding for an N-terminal HA-tag and flanking PacI and NotI restriction sites. The PCR products were cloned in the PacI and NotI sites of pMX-IRES-GFP (A. Nussenzweig, National Institutes of Health). The Lenti-Cas9-2A-Blast construct was from J. Moffat (University of Toronto). All constructs were sequence-verified.

Selection of and Purification of the 53BP1-Binding Ubiquitin Variants

The phage-displayed Ubv library used in this study was re-amplified from Library 2 as previously described [7]. Protein immobilization and subsequent phage selections were performed according to established protocols [31]. Briefly, purified 53BP1 protein fragments were coated on 96-well MaxiSorp plates (Thermo Scientific 12565135) by adding 100 µL of 1 µM proteins and incubating overnight at 4° C. Afterwards, five rounds of selection using the phage-displayed Ubv library were performed against immobilized proteins. A total of 96 phage clones obtained from the fourth and the fifth round of binding selections (48 from each round) were subjected to clonal ELISA to identify individual phages with improved binding properties towards 53BP1. The resulting Ubv sequences were derived through phagemid DNA sequencing [31]. For phage ELISA, proteins in study (53BP1 and/or control proteins) were immobilized on 384-well MaxiSorp plates (Thermo Scientific 12665347) by adding 30 µL of 1 µM proteins for overnight incubation at 4° C. before adding amplified phages (1:3 dilution in PBS+1%BSA+0.05% Tween) and incubated overnight. Binding of phage was detected using anti-M13-HRP antibody (GE Healthcare 27942101).

Pulldowns

MBP and GST pulldowns were done essentially as previously described [13] with the modifications described below. The following buffer was used for the binding reactions: 50 mM Tris-Cl pH 7.5, 50 mM NaCl, 0.01% NP40 and 1% BSA. 10 µg and 2.5 µg of the MBP- and GST-fusion proteins were also used as baits, respectively. For peptide competition pulldowns 2.5 µg MBP-53BP1-Tudor was coupled to amylose resin (New England Biolabs) and 0.75 µg GST-UbvG08 was added simultaneously to a biotin-labeled peptide derived from histone H4K20me2 (Biotin-Mini-PEG-YGKGGAKRHRKme2VLRD; BioBasic Canada Inc.) for 2 h at 4° C. Peptide pulldowns were washed in binding buffer, eluted with SDS-PAGE sample buffer, and analyzed by immunoblotting. For all pulldowns, 1-2% of the total amount of the input proteins was separated by SDS-PAGE and probed for immunoblotting.

Protein Expression, Crystallization and Structure Determination

The 53BP1 Tudor domain (residues 1784-1603) and UbvG08 were individually expressed and purified from bacteria as GST-tagged fusion proteins. In brief, GST-tagged fusion proteins were purified from bacterial lysates on to glutathione-Sepharose (GE Healthcare), washed, and then eluted by TEV protease digestion to GST moieties, followed by purification by size exclusion chromatography (SEC). The 53BP1 Tudor-UbvG08 complex was formed by mixing purified proteins at equimolar concentration, incubating overnight at 4° C., and purifying the complex by SEC in 10 mM Tris-Cl pH 7.5, 150 mM NaCl and 1 mM DTT column buffer. Crystals of the complex were grown at 20° C. using the hanging drop vapor diffusion method by mixing equal volumes (1 µL) of complex at 28.5 mg/ml with crystallization buffer consisting of 0.1 M MES pH 6.0, 0.2 M trimethylamine N-oxide and 25% (w/v) PEG MME 2000. Crystals were cryo-protected by a quick soak in crystallization buffer supplemented with 20% glycerol, prior to flash freezing. A single crystal dataset was collected at −180° C. on a home-source consisting of a Rigaku MicroMax-007 HF rotating anode generator, coupled to a R-axis 4++ detector (Rigaku) and VariMax multilayer optics. Data processing was performed using the XDS software suite. The structure of a single 53BP1 Tudor-UbvG08 complex in the asymmetric unit was solved by molecular replacement using the apo Tudor domain (PDB 2IG0) and ubiquitin (PDB 3NHE chain B) as search models in Phaser (Phenix suite). Structure refinement was performed using Refine (Phenix suite). See Table 1 for data collection and refinement statistics.

Immunoprecipitation 293T cells were transfected with 10 µg of pcDNA3-Flag-i53-derived plasmids using polyethylenimine (PEI). 48 h post-transfection, cells were lysed in 1 mL high salt lysis buffer (50 mM Tris-HCl pH 7.6, 300 mM NaCl, 1 mM EDTA, 1% (v/v) Triton X-100, and 1× protease inhibitors (Complete, EDTA-free, Roche)) and cell lysates were clarified by centrifugation at 4° C. 100 µL was removed as the input sample. The remaining lysate was incubated with ~15 µL anti-Flag (M2) affinity gel (Sigma) for 2 h at 4° C. The immunoprecipitates were then washed twice with high salt lysis buffer, once with 50 mM Tris-HCl pH 8.0, 0.1 mM EDTA and eluted in 25 µL 2× Laemmli sample buffer for analysis by immunoblotting.

Antibodies

The following antibodies were employed: rabbit anti-53BP1 (A300-273A, Bethyl), mouse anti-γ-H2AX (clone JBW301, Millipore), mouse anti-53BP1 (#612523, BD Biosciences), rabbit anti-GST (sc-459, Santa Cruz), a mouse anti-HA (F-7, sc-7392, SantaCruz or clone 12CA5, from M.

Tyers, University of Montreal), mouse anti-MBP (E8032S, NEB), mouse anti-Flag (clone M2, Sigma), rabbit anti-Flag (#2368, Cell Signaling), mouse anti-tubulin (clone DM1A, Calbiochem), mouse anti-p53 (sc-126, Santa Cruz), rabbit anti-ubiquitin (Z0458, DAKO), rabbit anti-BRCA1 (#07-434, Millipore or home-made antibody [6]). Goat anti-GFP (from L. Pelletier, Lunenfeld-Tanenbaum Research Institute), HRP-conjugated AffiniPure goat anti-rabbit IgG (Jackson ImmunoResearch), HRP-linked sheep anti-mouse IgG (NA931, GE Healthcare). Alexa Fluor 488 goat anti-mouse and anti-rabbit IgG, Alexa Fluor 555 goat anti-mouse and anti-rabbit (MolecularProbes).

RNA Interference

All siRNAs employed in this study were single duplex siRNAs purchased from ThermoFisher. RNA interference (RNAi) transfections were performed using Lipofectamine RNAiMax (Invitrogen) in a forward transfection mode. The individual siRNA duplexes used were BRCA1 (D-003461-05), CtIP/RBBP8 (M-001376-00), 53BP1/T53BP1 (D-003549-01), KEAP1 (D-12453-02) or 53BP1/T53BP1 (D-003548-01), non-targeting control siRNA (D-001210-02). Except when stated otherwise, siRNAs were transfected 48 h before cell processing.

Inhibitors and Fine Chemicals

The following drugs and chemicals were used: DNA-PKcs inhibitor (NU7441; Genetex) at 10 μM, lovastatin (S2061; Selleck Chemicals) at 40 μM, doxycycline (#8634-1; Clontech), SCR7 (M60082-2; Xcessbio) at 1 μM. Olaparib was purchased from Selleck Chemicals.

Immunofluorescence Microscopy

Cells were grown on glass coverslips, fixed with 2% (w/v) paraformaldehyde in PBS for 20 min at room temperature, permeabilized with 0.3% (v/v) Triton X-100 for 20 min at room temperature and blocked with 5% BSA in PBS for 30 min at room temperature. Cells were then incubated with the primary antibody diluted in PBS-BSA for 2 h at room temperature. Cells were next washed with PBS and then incubated with secondary antibodies diluted in PBS-BSA supplemented with 0.8 μg ml$^{-1}$ of DAPI (Sigma) to stain DNA for 1 h at room temperature. The coverslips were mounted onto glass slides with Prolong Gold mounting agent (Invitrogen). Confocal images were taken using a Zeiss LSM780 laser-scanning microscope.

Reporter-Based DNA Repair Assays

The direct repeat (DR)-GFP assay to measure the frequency of HR and the strand annealing EJ2-GFP assay to measure the frequency of MMEJ were performed as previously described [24]. Briefly, U2OS DR-GFP or U2OS EJ2-GFP cells were transfected with 10 nM siRNA (Dharmacon) using Lipofectamine RNAiMAX (Invitrogen). 24 h later, the cells were transfected with the pCBASceI plasmid (Addgene #26477) and plasmids, using Lipofectamine 2000 (Invitrogen). 48 h post-plasmid transfection, the cells were trypsinized and the percentage of GFP-expressing cells was analyzed using the BD FACSCalibur flow cytometer.

The Lamin A (LMNA) assay to measure the frequency of introduction of the coding sequence for mClover at the 5' end of LMNA using the CRISPR/Cas9 was performed as previously described4. Parental or 53BP1Δ U2OS cell lines were transfected with the indicated plasmids using Lipofectamine RNAiMAX (Invitrogen). 24 h later, the cells were electroporated with 2.5 μg of sgRNA plasmids and 2.5 μg of donor template using a Nucleofector (Lonza; protocol X-001). Parental or 53BP1Δ U2OS cells stably expressing CtIP-T847E mutant were transfected with an siRNA against KEAP1 and the indicated plasmids and processed as previously described [4].

Mass Spectrometry

Following immunoprecipitation of Flag-tagged i53 and i-53-DM from HEK293 Flp-In/T-REx cells, peptides were identified using LC-MS/MS. Proteins were digested in solution with trypsin (Sigma, T7575-1KT) and dried to completeness. For LC-MS/MS analysis, peptides were reconstituted in 5% formic acid and loaded onto a 12-15 cm fused silica column with pulled tip packed in-house with 3.5 μm Zorbax C18 (Agilent Technologies, Calif., USA).

i53 and i53-DM precipitates were analyzed using an LTQ (Thermo Scientific) coupled to an Agilent 1100 Series HPLC (Agilent Technologies). Peptides were eluted from the column using a 90 min period cycle with a linear gradient from 0% to 40% ACN in 0.1% formic acid. Tandem MS spectra were acquired in a data-dependent mode for the top 5 (LTQ) most abundant ions using collision-induced dissociation. Acquired spectra were searched against the human Refseq_V53 database using Mascot (Matrix Science).

Isothermal Titration Calorimetry

Isothermal titration calorimetry was performed using a VP-ITC calorimeter (MicroCal). Untagged 53BP1 Tudor and UbvG08 (or UbvG08-DM mutant) were dialyzed into PBS and degassed. 100 μM UbvG08 in the syringe was titrated into 10 μM 53BP1 Tudor protein in the sample cell using 30 consecutive 10 μl injections at 25° C. Resultant binding isotherms were processed with Origin 5.0 software (Microcal). Curve fits were carried out using the one-set-of-sites model.

Olaparib Sensitivity Assays

Cells were seeded at a density of 20,000 cells/well in 6-well plates in the presence of olaparib at day 0. At day 4, the medium was refreshed with fresh inhibitor. At day 6, cells were collected by trypsinization and viable cell count was determined by Trypan blue exclusion using an automated cell counter (Vi-CELL, Beckman Coulter).

The results of the study are discussed below.

Figure 1F:
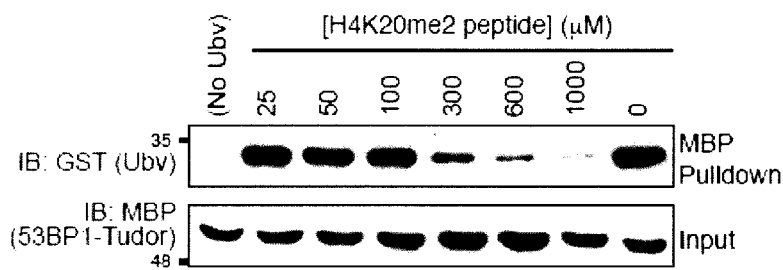
FIG. 1F, Competition assay in which the GST-UbvG08 was prebound to the MBP-Tudor fusion of 53BP1. Increasing amounts of a synthetic peptide derived from the region of H4K20me2 were added. After extensive washing, bound proteins were analyzed by immunoblotting against GST and MBP.
Figure 1E:
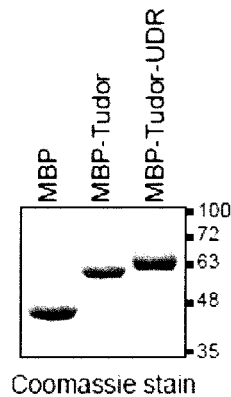
FIG. 1E, the various MBP proteins used in the pulldown assays were separated by SDS-PAGE and stained with Coomassie brilliant blue.

To identify inhibitors of 53BP1, advantage was taken of a soft-randomized library of ubiquitin variants (Ubvs) [7] that was initially developed to identify inhibitors of ubiquitin-binding proteins such as deubiquitylases. Since 53BP1 recognizes histone H2A ubiquitylated on Lys15 (H2AK15ub) in order to accumulate at DSB sites [13], it was reasoned that it might be possible to identify Ubvs targeting the 53BP1 ubiquitylation-dependent recruitment (UDR) motif, the domain involved in ubiquitylated histone recognition [13]. After 5 rounds of selection against a GST-53BP1 fragment containing the tandem Tudor domain and UDR (residues 1484-1631; FIG. 1A), 10 unique phages were selected for re-testing in ELISA assays for binding to the Tudor-UDR region of 53BP1 and 14 other proteins, most of them known ubiquitin-binding proteins (FIG. 1B). This process identified 5 distinct Ubvs that bound selectively to 53BP1 (A10, A11, C08, G08 and H04; FIG. 1BC). GST fusion proteins of 4 of these 5 Ubvs were then generated and tested in GST pulldown assays against MBP fused to either the Tudor domain (residues 1484-1603) or the Tudor-UDR fragment of 53BP1. In addition to binding the UDR-containing proteins, each Ubv bound to the MBP fusions containing only the 53BP1 Tudor domain (FIG. 1D, FIG. 1E). Since the UDR is apparently not required for binding to the Ubv, all further experiments were carried out with proteins containing solely the Tudor domain. Clone G08 was selected for further analysis because the phage expressing it displayed strongest binding by ELISA (FIG. 1B) and it contained 7 mutations, the lowest number of amino acid substitutions among the selected Ubvs (FIG. 1C).

Figure 1G:
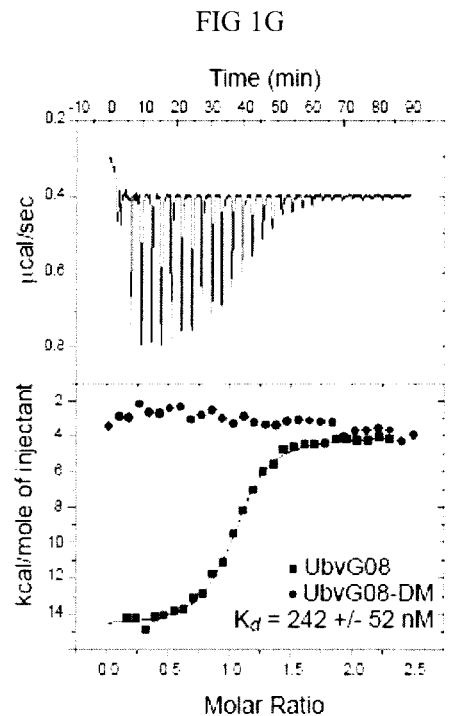
FIG. 1G, Isothermal titration calorimetry profiles obtained by titration of UbvG08 (squares) or UbvG08-DM (circles) titrated into a solution of the 53BP1 Tudor protein. Curves were fitted with a one-set-of-sites model. The dissociation constant ($K_d$) for the UbvG08-53BP1 interaction is indicated.

Since the 53BP1 Tudor domain binds to dimethylated histone H4 Lys20 (H4K20me2) [14], it was tested whether UbvG08- and H4K20me2-binding functions were mutually exclusive. H4K20me2 peptides competed UbvG08 for 53BP1 binding with a half-maximal competing concentration that lay in the range of 100 μM-300 μM (FIG. 1F). Since the dissociation constant ($K_d$) of the H4K20me2 peptide-53BP1 Tudor interaction is 20 μM [14], the results of the H4K20me2 peptide competition implied that 53BP1 bound to UbvG08 with much higher affinity than methyl-lysine peptides. Indeed, it was determined that the $K_d$ of UbvG08 binding to the 53BP1 Tudor domain, as assessed by isothermal titration calorimetry (ITC), was estimated to be at 242+/−52 nM (N=3) i.e. two orders of magnitude tighter than the 53BP1-H4K20me2 interaction (FIG. 1G). A version of UbvG08 that reverted the L69P and V70L mutations to wild type, L69 and V70 (mutant DM or UbvG08DM; see below for the rationale behind these mutations) did not display any detectable binding by ITC (FIG. 1G).

To gain insight into the mechanism by which UbvG08 binds to 53BP1, the complex formed by UbvG08 with the 53BP1 Tudor domain was crystallized and the structure was solved (see Methods for protein expression, crystallization and structure determination details). Within the solved complex, the Tudor domain of 53BP1 adopted a canonical mixed αβ fold identical to that reported in its apo state (1XNI; secondary structure RMSD of 1.0 Å) and in complex with a H4K20me2 derived peptide (2IG0; secondary structure RMSD of 1.1 Å) (FIG. 5A). UbvG08 displayed the expected ubiquitin-like fold consisting of a five-strand β-sheet (β1-5) buttressed against a single α-helix (α1) and a short $3_{10}$ helix. However, it harbored one notable difference from the canonical Ub structure: the register of strand β5 was shifted 4 positions from its expected position, resulting in an increase in the length of the loop preceding strand β5 by 4 residues and a shortening of the C-terminal tail of β5 by 4 residues (FIG. 5B, FIG. 5C).

Figure 2A:
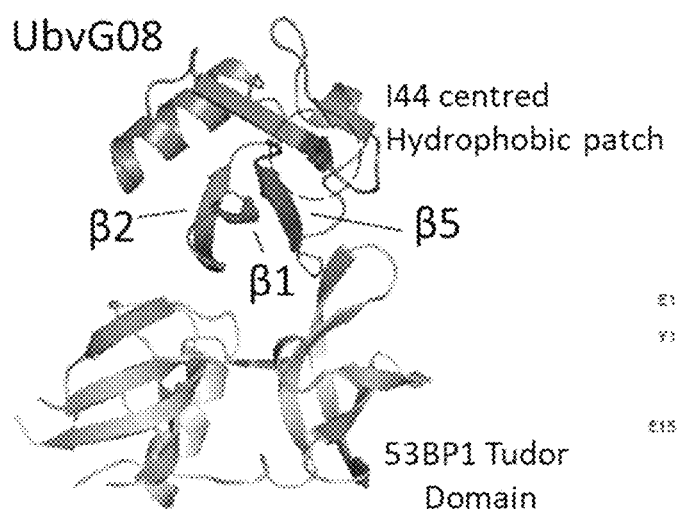
FIG. 2A, Ribbons representation of the UbvG08 (shown in green)—53BP1 Tudor domain (shown in gold) complex. The hydrophobic patch centered on I44 of the UbvG08 structure is highlighted in red.
Figure 2B:
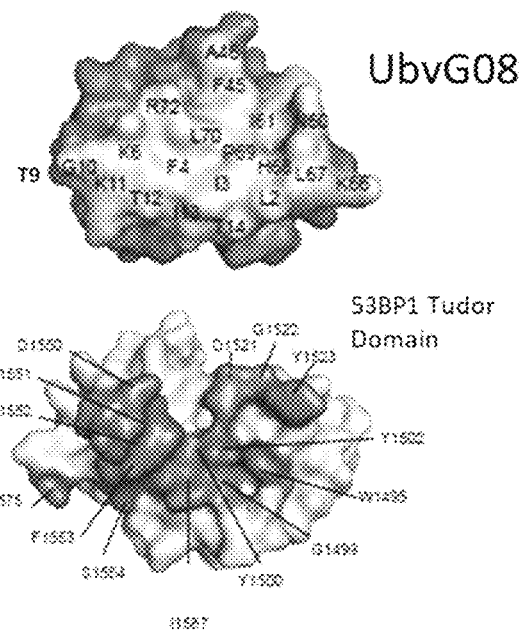
FIG. 2B, Reciprocal interaction surfaces on UbvG08 (top) and 53BP1 Tudor domain (bottom). Contact residues are highlighted on their respective surfaces.
Figure 2C:
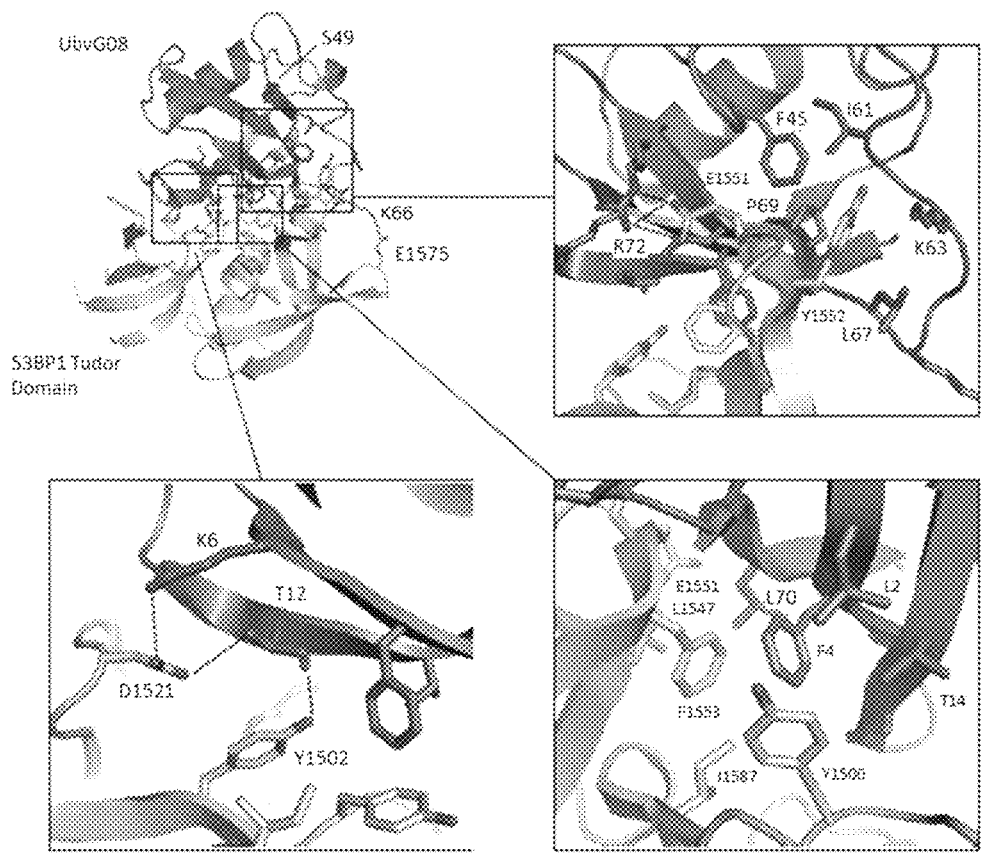
FIG. 2C, Zoom-in of the UbvG08-53BP1 Tudor domain contact region. Hydrogen and salt interactions are denoted by black dotted lines.

Complex formation was achieved by association of the β-sheet surface of UbvG08 centred on β1, β2 and β5, with the ligand-binding surface of the 53BP1 Tudor domain (FIG. 2A). This surface on the Ubv is adjacent to but distinct from the I44-centred hydrophobic patch that mediates the majority of ubiquitin-protein interactions [15]. The contact surfaces were extensive (buried surface area (BSA) =755.4 Å$^2$), and comprised of a mixture of hydrophobic and hydrophilic residues (FIG. 2B). Notable interactions include: 1) a hydrophobic cluster involving Tudor domain residues Y1500, F1553 and I1587 and UbvG08 residues L2, F4 and L70; 2) a network of salt and hydrogen-bonding interactions linking Tudor domain residues Y1502 and D1521 and UbvG08 residues T12 and K6; 3) a salt bridge between the Tudor domain residue E1551 and UbvG08 residue R72; 4) another salt bridge between the Tudor domain residue E1575 and UbvG08 residue K66; and 5) a hydrophobic interaction between Tudor domain residue Y1552 that packs against UbvG08 residues F45, P69 and L67 (FIG. 2C).

The basis for high-affinity binding between UbvG08 and the Tudor domain of 53BP1 appears multi-fold. Whereas the sequence of UbvG08 differs from wild type ubiquitin by 7 residues, only 4 substitutions are well positioned on the contact surface to allow direct interaction of their side chains with 53BP1. Specifically, L70 (Val in Ub) forms favourable hydrophobic contacts with 53BP1 F1553 and L1547; L2 (Gln in Ub) forms favourable hydrophobic contacts with 53BP1 Y1500; and P69 (Leu in Ub) forms favourable hydrophobic contact with 53BP1 Y1552 (FIG. 2C). Additionally, K66 (Thr in Ub) is well positioned to form a weak salt interaction with 53BP1 E1575 (FIG. 2C).

Other substitutions in UbvG08 may contribute to enhanced binding indirectly by stabilizing a shift in the register of strand β5. The L62 mutation (Gln in Ub) appears most important, as it resides at the initiating position of the normally tight loop preceding β5 in Ub (FIG. 5D). The L62 substitution causes a reorientation of the side chain from a solvent exposed orientation (in Ub) to a buried position (in UbvG08) in the hydrophobic core, which would be disruptive to tight turn-formation. Additionally, the substituted side chains of D64 (Glu in Ub) and K66 (Thr in Ub) occupy new positions in the enlarged solvent exposed loop preceding β5, whereas in the absence of a register shift, they would occupy positions in strand β3 directly facing the Tudor domain where they might otherwise contribute suboptimal interactions with 53BP1 (FIG. 5E). The register difference in strand β5 adds another additional layer of complexity due to the non-substituted R72 side-chain now displaced by 17 Å from its expected position in Ub, allowing it to form a near ideal salt interaction with E1551 in the Tudor domain (FIG. 2C). Based on its position that is remote from both the contact surface with 53BP1 and the strand β3 of the UbvG08, it appears that S49 (Gln in Ub) does not contribute materially to the binding affinity for 53BP1 (FIG. 2C).

Figure 2D:
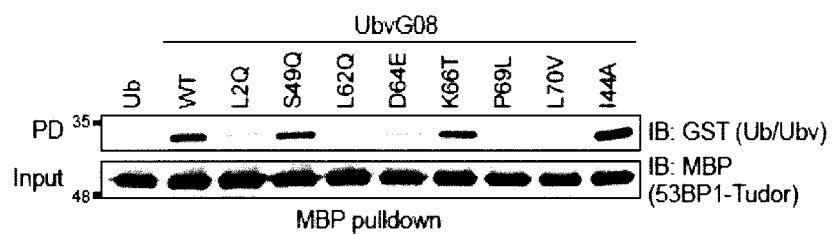
FIG. 2D, MBP pulldown assay of GST fused to ubiquitin (Ub) or to the indicated UbvG08 proteins, with the MBP-53BP1-Tudor protein.
Figure 2E:
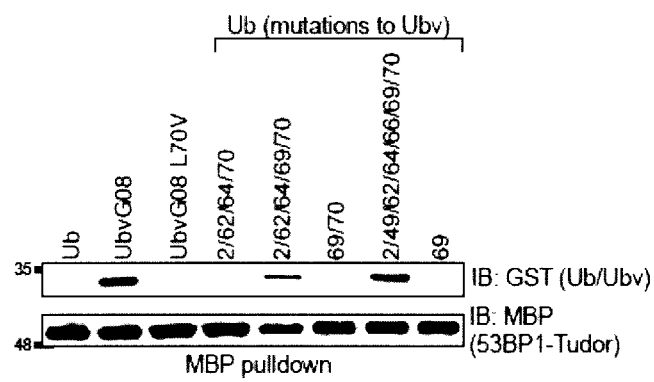
FIG. 2E, MBP-pulldown assay of GST fused to UbvG08, its L70V mutant or the indicated Ub proteins, with the MBP-53BP1-Tudor protein.
Figure 2F:
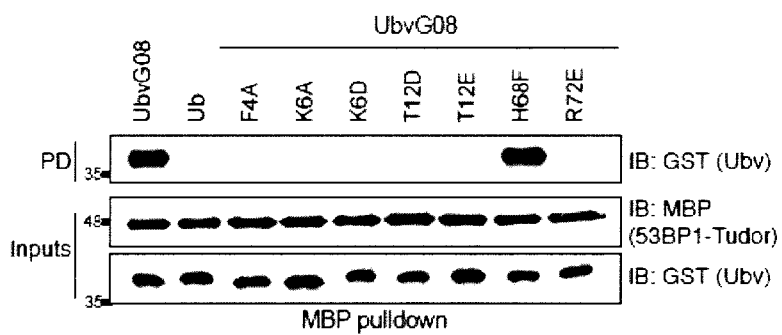
FIG. 2F, MBP-pulldown assay of GST fused to ubiquitin (Ub) or to the indicated UbvG08 proteins, with the MBP-53BP1-Tudor protein. PD, pulldown. IB, immunoblot.
Figure 6A:
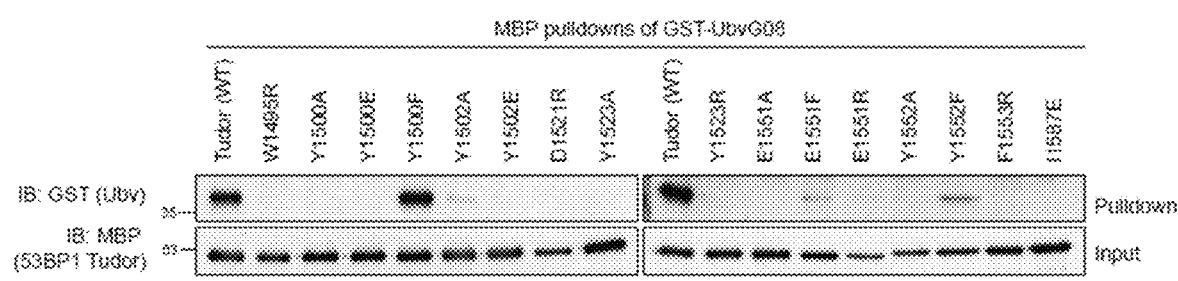
FIG. 6 (Related to FIG. 2.) FIG. 6A, MBP pulldown assay where the indicated MBP-53BP1 Tudor proteins were incubated with GST-UbvG08.
FIG. 6B, Peptide pulldown assays where the immobilized biotin-H4K20me2 peptide was used to retrieve MBP-53BP1 Tudor or the proteins as indicated. IB, immunoblot.
Figure 6B:
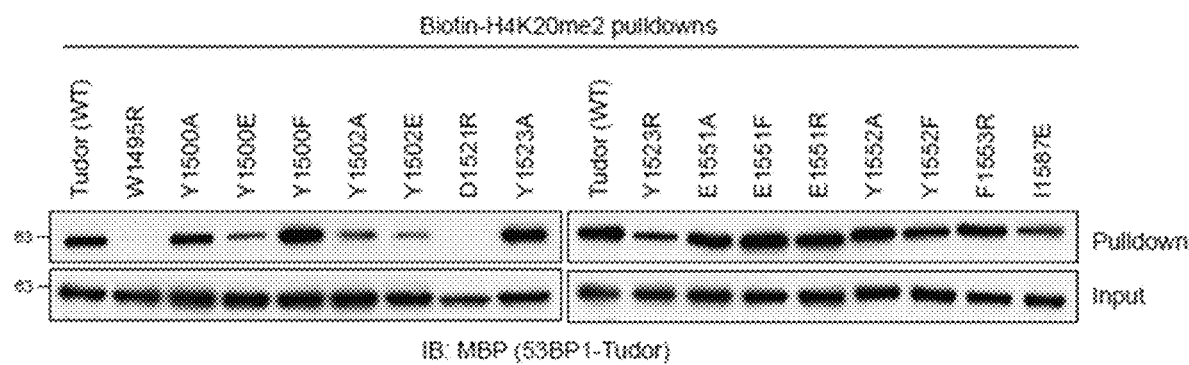

To validate the functional significance of features observed in the crystal complex, the respective binding surfaces were interrogated with site-directed mutagenesis. The impact of individually reverting each of the 7 substitutions in UbvG08 to their Ub counterparts was assessed. The L2Q, L62Q, D64E, P69L and L70V reversions all reduced UbvG08 binding to 53BP1 in pulldown assays, with the P69L and L70V mutations having the strongest effect (FIG. 2D). Indeed, simultaneous reversions of P69 and L70 to their Ub counterparts (Ubv08-DM) completely abolished UbvG08 binding to the 53BP1 Tudor domain, as measured by ITC (FIG. 1G). In a converse set of experiments, the simultaneous mutation of the equivalent residues in Ub into their UbvG08 counterparts was found to be sufficient to convert Ub into a robust 53BP1-binding protein, as measured in pulldown assays (FIG. 2E). The importance of the non-substituted (i.e. same as Ub) residues in UbvG08 (FIG. 2F) as well as the residues on the 53BP1 Tudor domain predicted by the model were also assessed to be engaged in key interactions (FIG. 6A, FIG. 6B). These analyses strongly validated the structural model of the UbvG08-53BP1 interaction.

Whether intracellular expression of UbvG08 could inhibit 53BP1 in cells was tested. Flag-tagged versions of UbvG08 and the DM mutant were prepared. The C-terminal di-glycine motif was removed to preclude its incorporation in the active ubiquitin pool and a I44A mutation was also incorporated, which disables the majority of ubiquitin-dependent interactions [15] but does not impact the interaction of UbvG08 with 53BP1 (FIG. 2D). This version of Ubv-G08 is referred to hereafter as inhibitor of 53BP1 or i53 (SEQ ID NO: 9).

Figure 3A:
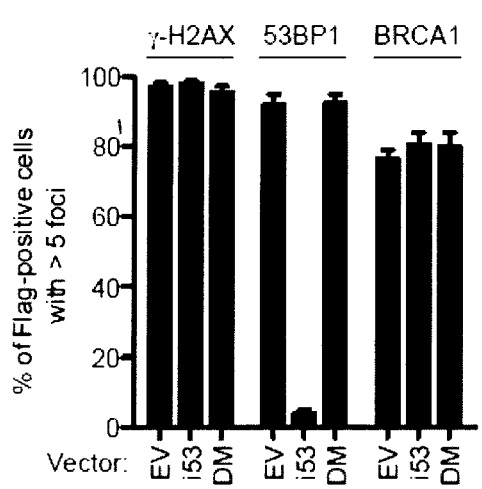
FIG. 3A-B, U2OS cells were transfected with vectors expressing i53, its 53BP1-binding deficient mutant (DM) or an empty vector (EV) control. Cells were then X-irradiated with a 10 Gy dose and processed for immunofluorescence with the indicated antibodies 1 h post-irradiation (IR). DAPI staining (not shown) was used to delineate the outline (dashed lines) of the cell nuclei. The region in the magnified inset is indicated with a square. Quantitation of the experiment is shown in panel (a) and data is indicated as the mean±s.e.m (N=3), whereas in (b) representative micrographs are shown. Arrowheads indicate Flag-positive cells. Additional micrographs are shown in FIG. 7A.
Figure 3B:
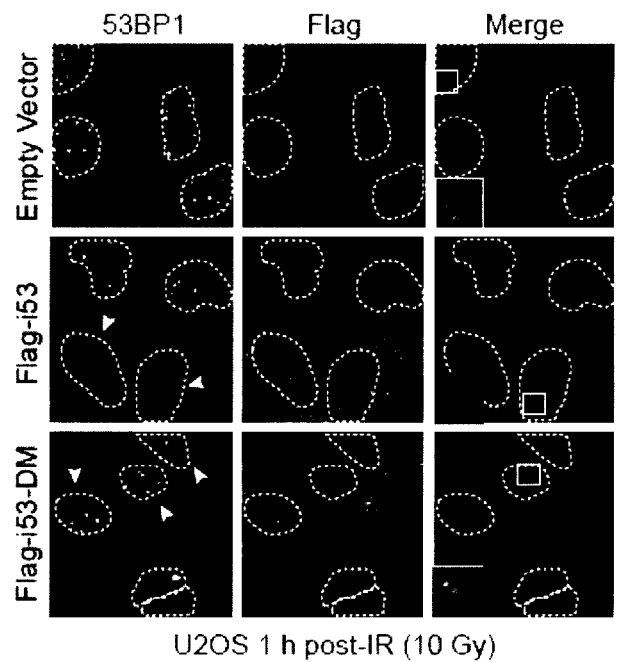
Figure 3C:
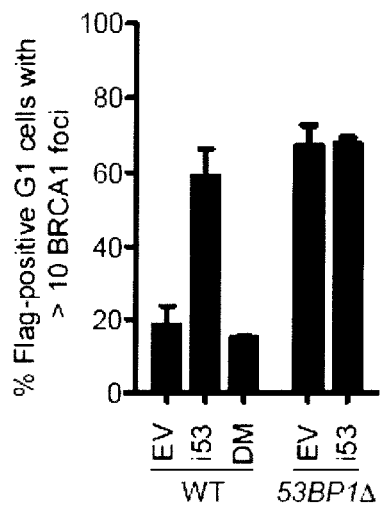
FIG. 3C, Parental or 53BP1ΔU2OS cells transfected with vectors expressing i53, the DM mutant or an empty vector (EV) control were irradiated (10 Gy) 1 h before being processed for immunofluorescence. Cell cycle stage was assessed by Cyclin A staining. The data is presented as the mean±s.e.m.; N=3. Micrographs are shown in FIG. 7B.
Figure 3D:
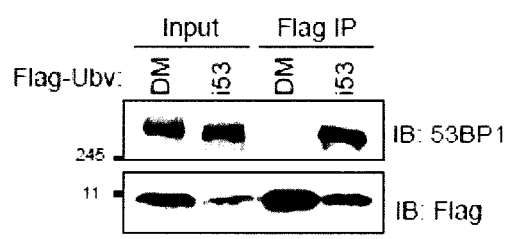
FIG. 3D, Immunoprecipitation (IP) of Flag-tagged proteins from extracts prepared from 293T cells transfected with vectors expressing Flag-i53 or the i53-DM mutant. Proteins were separated by SDS-PAGE and immunoblotted (IB) for Flag and 53BP1.
Figure 7A:
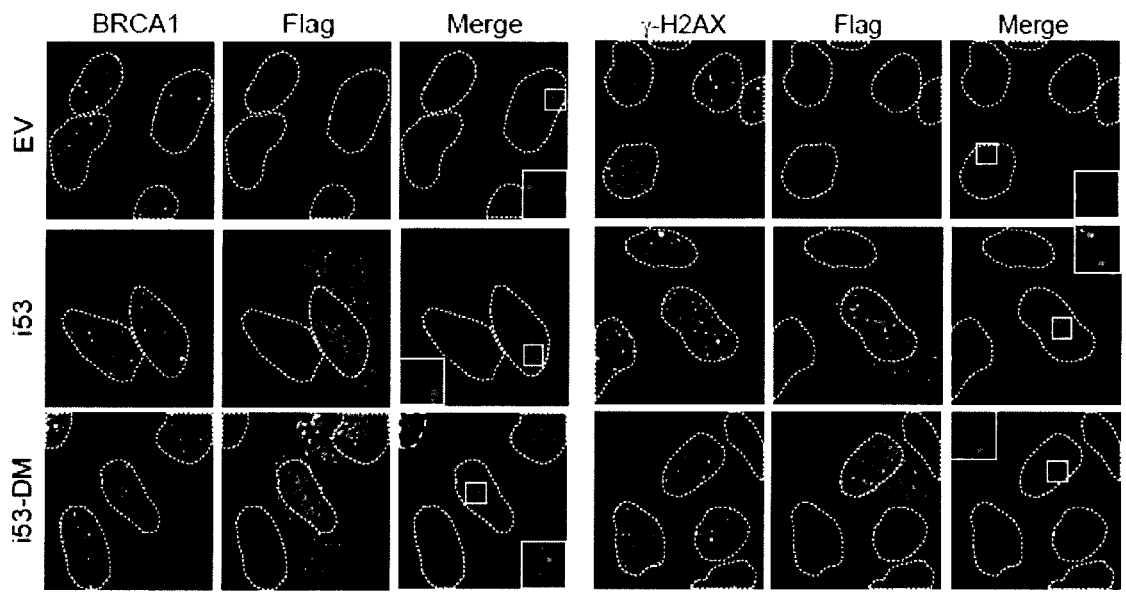
FIG. 7 (Related to FIG. 3.) FIG. 7A, Representative micrographs of the experiment shown in FIG. 3A-B.
FIG. 7B, Representative micrographs of the experiment shown in FIG. 3C.
Figure 7B:
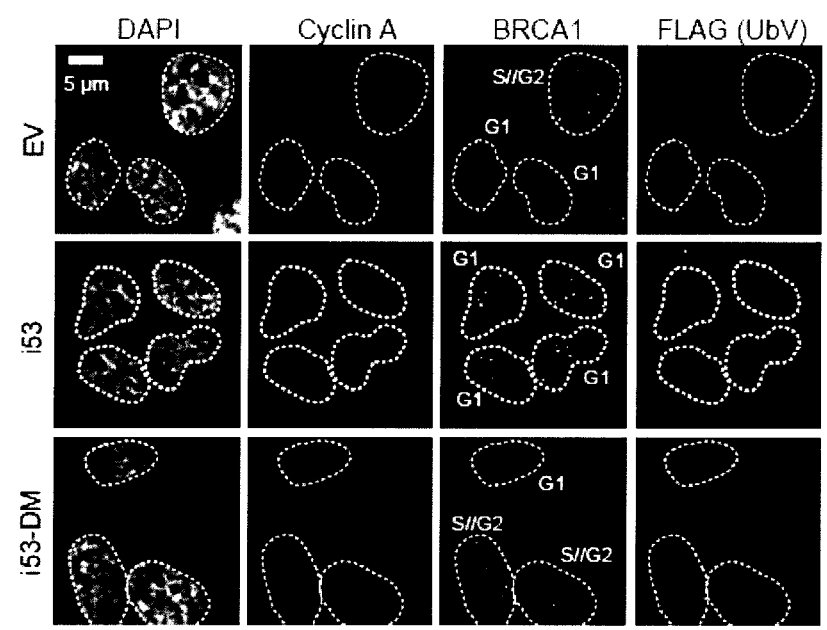

When U-2-OS (U2OS) cells transfected with vectors expressing i53 or its DM mutant (i53-DM; see UbvG08 DM mutant above) were irradiated with a 10 Gy dose of X-rays, it was observed that i53 but not the 53BP1-binding defective DM mutant (i53-DM) strongly suppressed 53BP1 recruitment to DSB sites, as monitored by ionizing radiation focus formation (FIG. 3A,B). The inhibition of focus formation was specific to 53BP1, as i53 did not impact γ-H2AX and BRCA1 focus formation (FIG. 3A and FIG. 7A). Transfection of i53 also induced BRCA1 accumulation at DSB sites in G1 cells [6] to a similar extent as that caused by loss of 53BP1 [4,6], providing a first clue that i53 not only inhibits 53BP1 recruitment to damaged chromatin but also that it can act as an inhibitor of 53BP1 function (FIG. 3C and FIG. 7B). i53, but not its DM mutant efficiently retrieved 53BP1 in co-immunoprecipitation experiments (FIG. 3D) suggesting that the inhibition of 53BP1 recruitment to DSB sites occurs through binding to 53BP1 and occlusion of the Tudor domain ligand binding site.

Figure 4A:
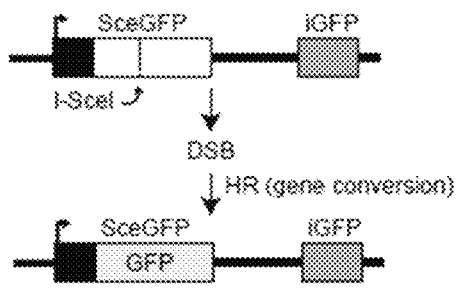
FIG. 4A, Schematic of the DR-GFP assay.
Figure 4B:
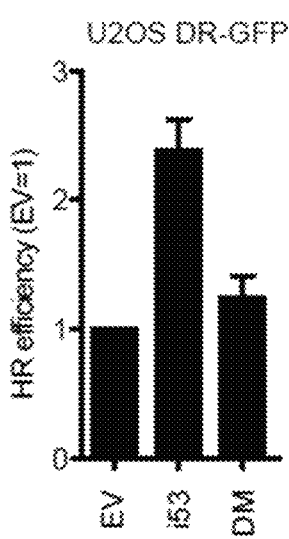
FIG. 4B. U2OS DR-GFP cells were transfected with the vectors expressing i53, the DM mutant or an empty vector control (EV) along with an I-SceI expression vector. The percentage of GFP-positive cells was determined 48 h post-transfection for each condition and was normalized to the empty vector condition (mean±s.d., N=4).
Figure 4C:
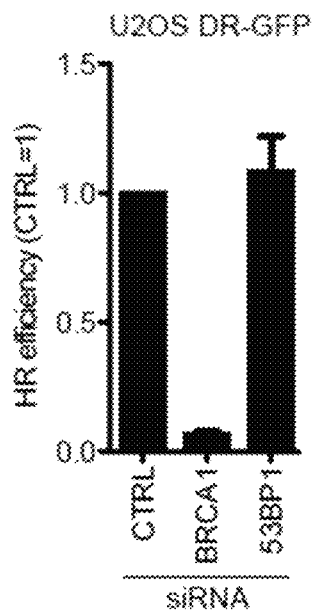
FIG. 4C, U2OS DR-GFP were first transfected with siRNAs targeting the 53BP1 or BRCA1 mRNAs along with a non-targeting siRNA (CTRL). 24 h post-transfection, cells were transfected with the I-SceI expression vector and the percentage of GFP-positive cells was determined 48 h post-siRNA transfection for each condition. The values were normalized to the empty vector condition and presented as the mean±s.e.m; N=4.
Figure 8A:
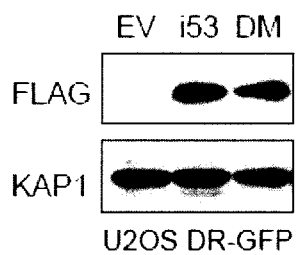
FIG. 8 (Related to FIG. 3.) FIG. 8A, Immunoblots of whole cell lysates prepared from U2OS DR-GFP cells transfected with vectors expressing Flag-tagged i53, its DM mutant or an empty vector along with an I-SceI expression vector and probed with the indicated antibodies. This blot relates to the experiment shown in FIG. 4B.
FIG. 8B, U2OS DR-GFP cells were transfected with the vectors expressing Flag-tagged i53 or the DM mutant along with an I-SceI expression vector. Cells were treated either with DMSO (−)
FIG. 8C, Control immunoblot of the experiment shown in (b).
FIG. 8D, Immunoblots of whole cell lysates prepared from U2OS DR-GFP cells transfected with the indicated siRNAs along with an I-SceI expression vector and probed with the indicated antibodies. This blot relates to the experiment shown in FIG. 4C.
FIG. 8F, Control immunoblot for the experiment shown in (E).
Figure 8B:
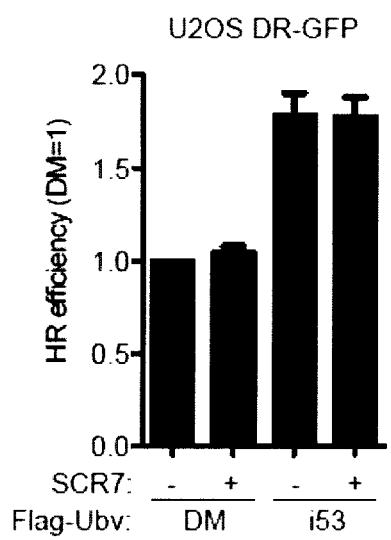
Figure 8C:
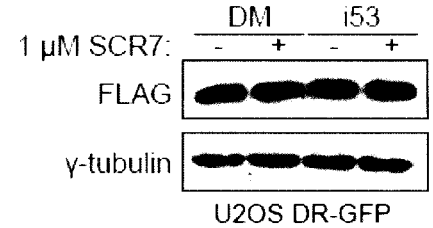
Figure 8D:
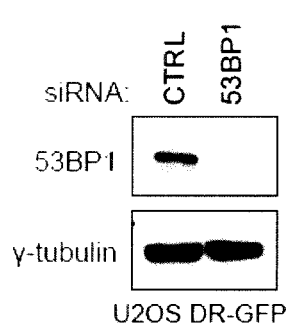
Figure 8D:
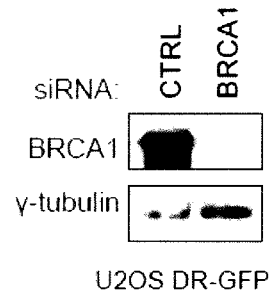

Loss of 53BP1 results in increased HR levels [16] making inhibitors of 53BP1 potential tools to manipulate DSB repair pathways during genome engineering reactions. The depletion of 53BP1 by siRNA, while near complete as determined by immunoblotting (FIG. 8D), is often insufficient to induce HR in the well-characterized direct-repeat (DR)-GFP assay17 (FIG. 4C). Whether i53 impacted gene conversion frequency was assessed using the well-characterized direct-repeat (DR)-GFP assay [17] (FIG. 4A). It was observed that i53 led to a 2.4-fold (+/−0.25) increase in gene conversion efficiency when compared to the empty vector control, whereas the i53-DM mutant had virtually no impact on gene conversion (1.25-fold+/−0.17; FIG. 4B and FIG. 8A). As a point of comparison, i53 was compared to SCR7, the reported inhibitor of the NHEJ factor DNA ligase IV [18], which has been shown in some systems to increase homology-dependent repair [19, 20]. Also tested was its related pyrazine analog, which has been proposed to be the active SCR7 analog (world wide web at tocris.com/dispprod.php?ItemId=432017#.VvUhqt-rSRs). i53 was a more potent inducer of gene conversion, compared to SCR7 and to SCR7 pyrazine, which had minimal impact in this assay (FIG. 8C). 53BP1 inhibition through i53 expression also stimulated gene conversion more than 53BP1 depletion by siRNA (FIG. 4B,C and FIG. 8D). From these assays, it was concluded that i53 stimulates gene conversion through the inhibition of 53BP1.

Figure 4D:
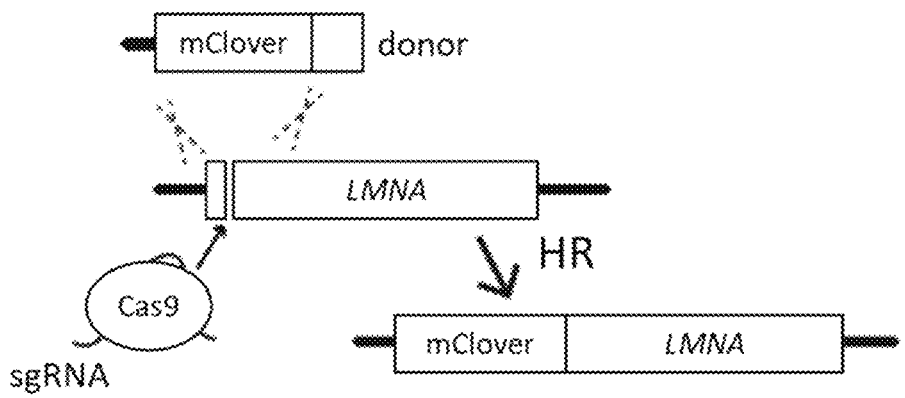
FIG. 4D, Schematic of the gene targeting assay.
Figure 4E:
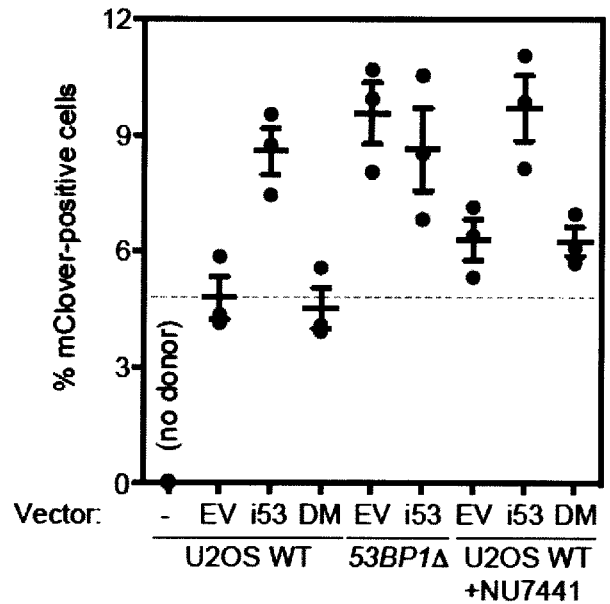
FIG. 4E, Gene targeting efficiency at the LMNA locus in parental or 53BP1Δ U2OS cells following transfection with vectors expressing Flag-tagged i53 or its DM mutant or an empty vector control (EV). The DNA-PK inhibitor NU7441 was also added where indicated. 24 h post-transfection, cells were analysed for mClover fluorescence. Individual experiments are presented with the error bar representing the s.d., (N=3).

As an orthogonal approach, it was also tested whether i53 expression increased the efficiency of gene targeting stimulated by CRISPR/Cas9. Advantage was taken of a recently described gene-targeting assay that involves the introduction of the coding sequence for a bright GFP variant, mClover, at the 5' end of the gene coding for Lamin A (LMNA) [4, 21] (FIG. 4D). Gene targeting at the LMNA locus is not responsive to SCR7 treatment [21], suggesting that end-joining may not provide a strong a barrier to HR at this locus. Indeed, inhibition of DNA-PK, a core NHEJ factor, with NU7441 only resulted in a modest increase in gene targeting in this assay (FIG. 4E). However, it was observed that i53, but not the DM mutant, increased gene-targeting nearly two-fold (from 4.79% +/−0.5% for the empty vector control to 8.58% +/−0.6% for the i53 condition). The gene-targeting efficiency in i53-expressing cells approached that of 53BP1-null cells (53BP1Δ) [4], suggesting that the inhibition of 53BP1 was near complete. Introduction of i53 in 53BP1Δ cells did not result in a further increase in gene targeting demonstrating that the effect of i53 on HR is via inhibition of 53BP1. Finally, it was found that combining DNA-PK inhibition and i53 led to an additive increase in gene targeting, consistent with 53BP1 modulating HR primarily through the regulation of DNA end resection rather than the efficiency of NHEJ.

Although UbvG08, the parent molecule of i53, shows a high degree of selectivity towards 53BP1 in ELISA assays (FIG. 1B), it was sought to determine the repertoire of cellular proteins bound by i53. 293T Flp-In/T-Rex cell lines were generated that expressed Flag-tagged i53 or i53-DM under the control of a tetracycline-inducible promoter as previously described [22]. Nine IP-MS experiments were analyzed (3 biological replicate IPs each for control i53- and i53-DM expressing cell lines). The interacting proteins were identified by MASCOT to identify high-confidence interactors for i53. The only protein found to interact with i53 in two or more experiments was 53BP1 (Table 2). It was concluded that i53 is a highly selective binder of 53BP1 in cells.

Figure 8E:
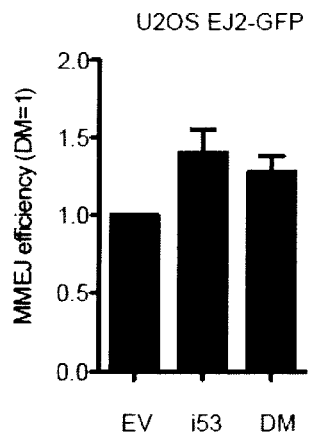
Figure 8F:
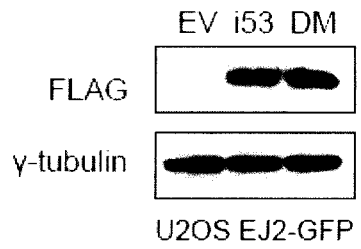

DNA end resection inhibits NHEJ but can activate alternative end-joining pathways in addition to activating HR [23]. Resection can reveal regions of microhomology that may be rejoined in a process termed microhomology-mediated end joining (MMEJ). MMEJ is a mutagenic process because it invariably leads to microdeletions or nucleotide insertions. To assess whether 53BP1 inhibition by i53 increases MMEJ, the EJ2-GFP reporter assay [24, 25] was employed. i53 expression increased MMEJ (1.4+/−0.15 fold over the empty vector; FIG. 8E,F) but since the expression of the DM mutant also increased MMEJ to a similar extent (1.3+/−0.1 fold), it is unlikely that the modest increase in MMEJ observed following i53 expression is due to 53BP1 inhibition.

Figure 4F:
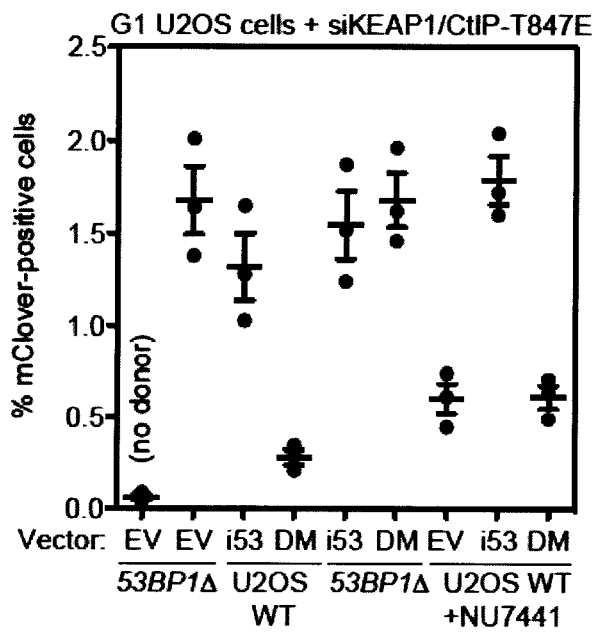
FIG. 4F, Gene targeting at the LMNA locus in G 1-arrested parental (WT) or 53BP1Δ U2OS cells transfected with vectors expressing Flag-tagged i53 or its DM mutant or an empty vector control (EV). The DNA-PK inhibitor NU7441 was also added in the indicated conditions. 24 h post-transfection, cells were analysed for mClover fluorescence. Individual experiments are present with the error bar representing the s.d., (N=3).

Finally, the use of precise genome editing by HR is currently hampered by the fact that cells in the G1 or G0 phase of the cell cycle are refractory to recombination. The mechanism by which HR is inhibited in G1 cells was recently elucidated and it was determined that reactivation of HR in G1 is possible through three distinct steps [4]: the inactivation of 53BP1, the restoration of the interaction between the HR factors BRCA1 and PALB2 (e.g. via depletion of KEAP1) and the activation of long-range resection through the expression of a phosphomimetic mutant of CtIP, CtIP-T847E [4]. It was therefore assessed whether i53 could substitute for the genetic inactivation of 53BP1 to activate HR in G1. Remarkably expression of i53 is nearly as efficient as the 53BP1 knockout in promoting Cas9-stiumulated gene targeting at the LMNA locus (FIG. 4F), suggesting that i53 could be included in a strategy to stimulate HR in non-dividing cells.

In summary, this study developed a genetically encoded inhibitor of 53BP1 that robustly stimulates homology-directed repair of DSBs. In addition to gene targeting applications, i53 could be useful in additional gene editing reactions where the engagement of the HR pathway is desired. Examples of such applications include interparalog gene conversion, of which a specific case includes correction of the mutated HBB hemoglobin gene by gene conversion with its paralog HBD in the treatment of sickle cell anemia. Other applications could include gene drives [26] (i.e., stimulated interhomolog recombination). The 53BP1 Tudor domain is nearly perfectly conserved across a wide range of vertebrate species, for example, mammalian research models, such as mice, and agriculturally important animals such as pigs and cows. Thus, it is expected that i53 will stimulate HR in those species as well.

Figure 9A:
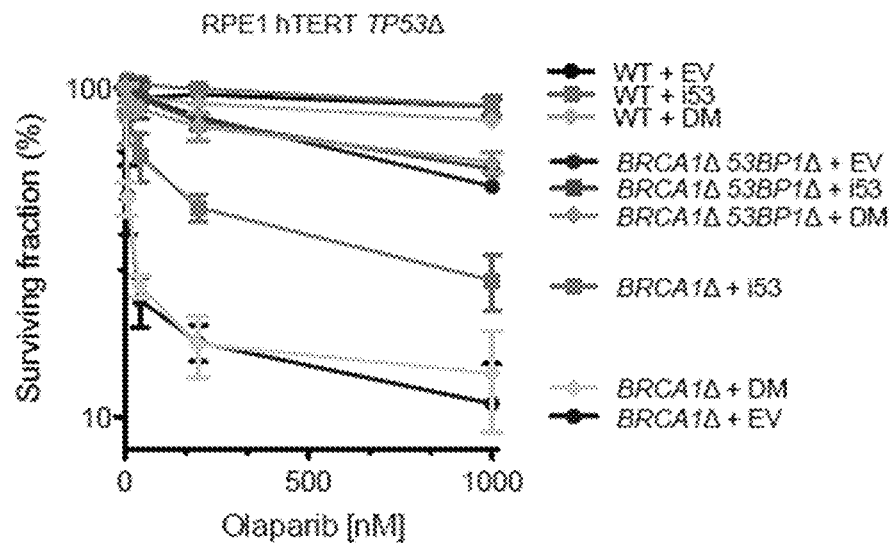
FIG. 9A, An isogenic set of cell lines derived from RPE 1-hTERT cells deleted for the gene coding for p53 (TP53Δ) containing either no further mutations (WT) or null mutations in BRCA1 (BRCA1Δ) or 53BP1 (53BP1Δ) alone or in combination, as indicated. These cell lines were transduced either with an empty virus (EV) or with lentiviruses that express HA-tagged i53 or its DM mutant. The virus also expressed GFP from an IRES. After sorting for GFP cells the viability of cells following olaparib treatment for 4 d was monitored by trypan blue exclusion. Data is presented as the mean +/- s.d. (N=3).
Figure 9B:
FIG. 9B, Whole-cell extracts from the isogenic sets of RPE1-hTERT TP53Δ cells were separated by SDS page and probed by immunoblotting with the indicated antibodies.
Figure 9C:
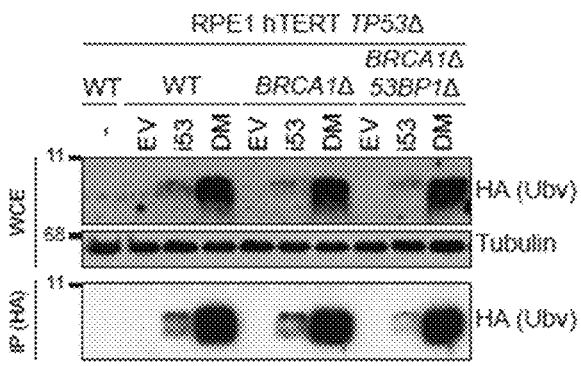
FIG. 9C, Expression of the HA-tagged Ubvs in the indicated RPE1-hTERT TP53Δ cell lines was determined by anti-HA immunoprecipitation (IP) followed by immunoblotting.

The versatility of the ubiquitin scaffold onto which i53 is built, along with the determination of the molecular basis of the i53-53BP1 interaction should enable improvement of 53BP1 inhibition either through protein engineering or through affinity maturation of the UbvG08 via additional rounds of mutagenesis and phage display selections. Although an increase in the affinity of i53 may not be necessary for certain applications, low expression levels of i53 were insufficient to completely inhibit 53BP1. Indeed, lentiviral delivery of i53 only partially alleviated the poly (ADP-ribose) polymerase (PARP) inhibitor sensitivity in BRCA1-deficient RPE1-hTERT cells compared to a genetic deletion of 53BP1 (FIG. 9A,B). Finally, DNA ligase IV inhibition by SCR7 [18] was recently reported to stimulate homology-based genome editing [19, 20]. However, under the conditions of this study, i53 was found to be a more robust activator of HR than SCR7 or the DNA-PK inhibitor NU7441. There might be safety concerns in the clinical use of DNA ligase IV inhibitors, as DNA ligase IV deficiency is associated with stem cell depletion and genome instability, especially in the hematopoietic stem cell compartment [27, 28]. 53BP1 inhibition could be a propitious alternative for boosting HR rates.

EXAMPLE 2

Adeno-Associated Viral-Mediated Delivery of i53 as an Effective Means to Deliver i53 in Human Cells.

Figure 10A:
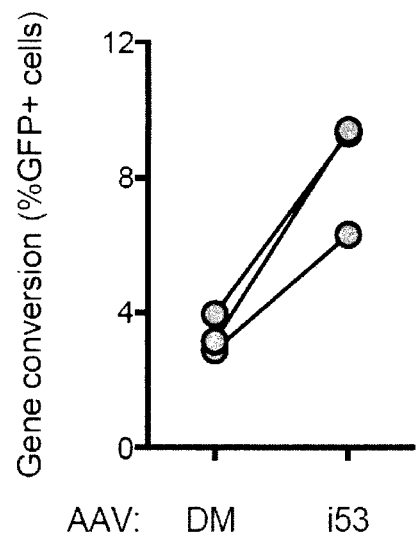
FIG. 10A, U2OS DR-GFP cells were first infected with an AAV-DJ1 virus coding either for Flag-i53-DM (DM) or Flag-i53. Infected cells were then transfected with an I-SceI expression vector and the percentage of GFP-positive cells, reflecting successful gene conversion, was determined by flow cytometry. Shown are three independent experiments, the lines connecting the DM and wild type i53 conditions done at the same time.
Figure 10B:
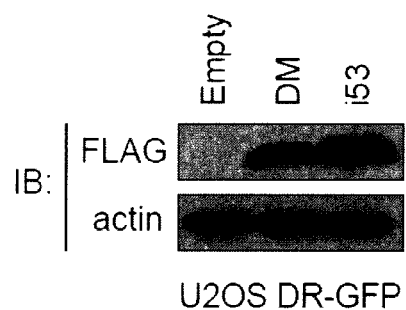
FIG. 10B, immunoblotting of Flag-tagged i53 expression in U2OS DR-GFP cells following AAV-mediated delivery. Actin immunoblotting is used as loading control.

Adeno-associated viruses (AAV) are widely used in gene therapy and are intensely investigated for use in therapeutic gene editing. AAV-mediated delivery of i53 was tested and found to stimulate homologous recombination using a DR-GFP gene conversion assay (FIG. 10).

EXAMPLE 3 i53 Stimulates Homology-Directed Repair with Single-Stranded Oligonucleotides (ssODNs).

Figure 11D:
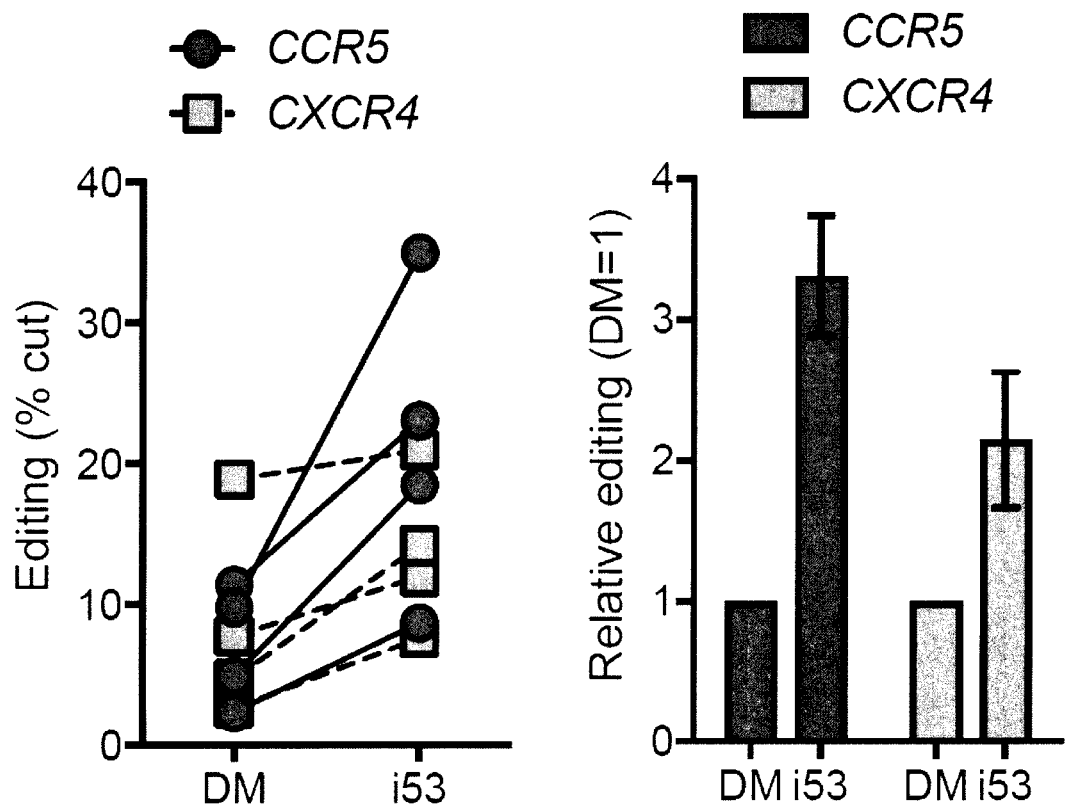
Figure 11E:
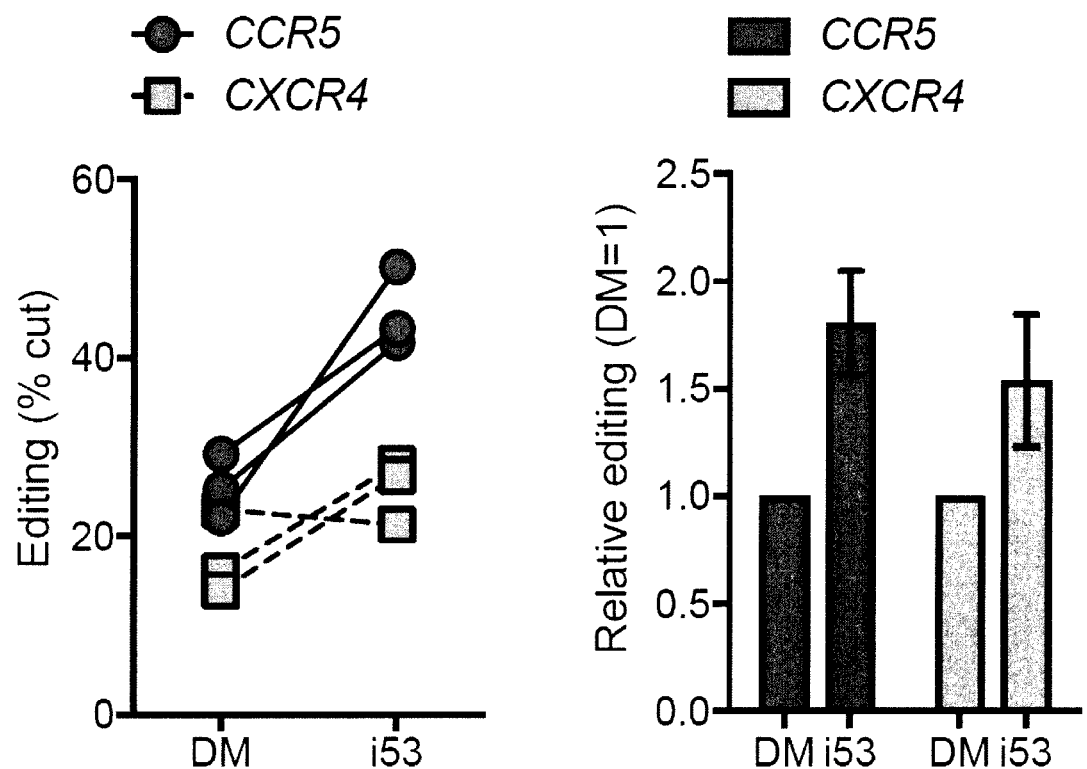

53BP1 inhibition, through i53 expression, stimulates HR reactions with long dsDNA donors (i.e. gene conversion and gene targeting) (see Example 1). These types of HR reactions rely on DNA end resection and the RAD51 recombinase. Shorter single-stranded oligonucleotides (ssODNs) are also used for precise genome engineering. A study was performed to test whether i53 could also stimulate HR by ssODNs. An assay developed by Corn et al (Corn, J E et al, Nat Biotechnol. 2016 Mar;34(3):339-44. doi: 10.1038/nbt.3481. Epub 2016 Jan. 20.) where a BFP reporter gene is converted to GFP using an ssODN template (FIG. 11A), was used in the study. Using this assay, modest but highly reproducible stimulation of HDR by ssODNs with i53 (1.3-1.4-fold; FIG. 11B) was observed. This initial observation prompted an assessment of whether i53 stimulates HR with ssODNs at two endogenous loci in 293T and K562 cells. The assay consists of the introduction of a new restriction site in the genome, either at the CCR5 or CXCR4 loci, as in Corn et al, supra. As shown in FIG. 11C-D, i53 stimulates HR by ssODN in the range of 1.5- to 3-fold over the 53BP1 binding-deficient i53-DM mutant. Therefore, it was concluded that i53 stimulates HR with ssODN donors.

The following materials and methods were used in the studies described in Examples 2 and 3.

Preparation of RNPs

Purified SpCas9 was diluted to 3.2 µg/µl in Cas9 buffer (20 mM HEPES (pH 7.5), 150 mM KCl, 1 mM MgCl$_2$, 10% glycerol and 1 mM TCEP), and sgRNAs were diluted to 0.8 µg/µl in Cas9 buffer. 5 µl of diluted SpCas9 was slowly mixed into 5 µl of diluted sgRNA, then incubated for 10-20 minutes at room temperature.

ssODN-Based BFP-to-GFP HR Assay

The BFP-to-GFP assay was performed essentially as described Richardson CD et al, Nat Biotechnol. 2016 34(3): 339-44, Epub 2016 Jan. 20.PMID: 26789497). Briefly, HEK293T cells were transduced at a low MOI (<0.3) with a lentivirus expressing BFP under the control of an EF1α promoter (Addgene #71825) and sorted by flow cytometry to produce a pure population of BFP-expressing cells. $2 \times 10^5$ cells were resuspended in 20 µl SF buffer (Lonza) and nucleofected with 10 µl sgBFP RNP and 100 pmol of ssODN donor, using program DS-150 on a Nucleofector 96-well Shuttle system (Lonza). After 4 days, BFP and GFP fluorescence were measured by flow cytometry on a BD Fortessa, and analyzed with FlowJo v10 software.

ssODN-Based RFLP HDR Assay

The CCR5 and CXCR4 RFLP assays were performed essentially as described (Richardson CD et al, 2016, supra). Briefly, $2 \times 10^5$ K562 or HEK293T cells were resuspended in 20 µl SF buffer (Lonza) and nucleofected along with 10 µl sgCCR5 or sgCXCR4 RNPs and 100 pmol of ssODN donor, using program FF-120 or DS-150, respectively, on a Nucleofector 96-well Shuttle system (Lonza). Three days later, genomic DNA was purified from the cells using a Qiagen DNeasy kit (Qiagen). The CCR5 and CXCR4 loci were amplified by PCR from 400 ng of genomic DNA using Pfx Platinum Polymerase (Invitrogen) and the following PCR conditions: 95° C. for 5 min, 40 cycles of 95° C. for 30 s, 55° C. for 1 min, 68° C. for 4 min, and a final extension of 10 min. 200 ng of purified PCR product was digested overnight with PciI (New England Biolabs), then resolved on a 2% agarose gel and analyzed with ImageQuant software.

AAV-UbV Plasmid Construction

The region comprising Flag-UbV was PCR-amplified from pcDNA3-Flag-i53 (Addgene #74939) and pcDNA3-Flag-DM (Addgene #74940), with the addition of 5' ClaI and 3' HindIII sites. The GFP insert was removed from pAAV-GFP (Cell Biolabs, Inc.) using ClaI and HindIII-HF (New England Biolabs), and replaced with the ClaI- and HindIII-flanked Flag-UbV PCR products to produce pAAV-i53 and pAAV-DM. Plasmids were verified by diagnostic digest and sequencing.

Adeno-Associated Virus Production

AAV-293 cells (Agilent) were transfected with pAAV expression, pDJ and pHelper constructs (Cell Biolabs, Inc., USA) in equal amounts using PEI to produce AAV-DJ expression viruses. 48-72 h later, the viral supernatant was used to transduce target cells for 24 h, and assays were initiated a further 24 h later.

Cas9 RNP Reagents

| Target gene | Guide sequence | Targeting Donor | Non-targeting donor |
|---|---|---|---|
| BFP | ATGGCG TGCAGT GCTTCA GC (SEQ ID NO: 35) | GCCACCTACGGCAA GCTGACCCTGAAGT TCATCTGCACCACC GGCAAGCTGCCCGT GCCCTGGCCCACCC TCGTGACCACCCTG ACGTACGGCGTGCA GTGCTTCAGCCGCT ACCCCGACCACATG A (SEQ ID NO: 36) | AGTGGCCAGAGTCCAGC TTGGGCCCACGCAGGGG CCTGGCCAGCAGCAAGC AGCACTCTGCCCTCGTGG GTTTGTGGTTGCCCACAC ATGTCATTGGAGGTGAC ATCGATGTCCTCCCCATT GGCCT (SEQ ID NO: 37) |

-continued

| Target gene | Guide sequence | Targeting Donor | Non-targeting donor |
|---|---|---|---|
| CCR5 | TGACAT CAATTA TTATAC AT (SEQ ID NO: 38) | ACAAAACCAAAGAT GAACACCAGTGAGT AGAGCGGAGGCAG GAGGCGGGCTGCGA TTTGCTTCACATTGA TTTTTTGGCAGGGCT CACATGTATAATAA TTGATGTCATAGAT TGGACTTGACACTT GATAATCCATCTTG TTCCACCCTGTGCAT AAATAAAAAGTGAT CTTTTATAAAGT (SEQ ID NO: 39) | ATGGATTGGTCATCCTGG TCATGGGTTACCAGAAG AAACTGAGAAGCATGAC GGACAAGTACAGGCTGC ACCTGTCAGTGGCCGAC ATGTTCTTTGTCATCACG CTTCCCTTCTGGGCAGTT GATGCCGTGGCAAACTG GTACTTTGGGAACTTCCT ATGCAAGGCAGTCCATG TCATCTAC (SEQ ID NO: 40) |
| CXCR4 | GAAGCG TGATGA CAAAGA GG (SEQ ID NO: 41) | ATGGATTGGTCATC CTGGTCATGGGTTA CCAGAAGAAACTGA GAAGCATGACGGAC AAGTACAGGCTGCA CCTGTCAGTGGCCG ACATGTTCTTTGTCA TCACGCTTCCCTTCT GGGCAGTTGATGCC GTGGCAAACTGGTA CTTTGGGAACTTCCT ATGCAAGGCAGTCC ATGTCATCTAC (SEQ ID NO: 42) | ACAAAACCAAAGATGAA CACCAGTGAGTAGAGCG GAGGCAGGAGGCGGGCT GCGATTTGCTTCACATTG ATTTTTTGGCAGGGCTCA CATGTATAATAATTGATG TCATAGATTGGACTTGAC ACTTGATAATCCATCTTG TTCCACCCTGTGCATAAA TAAAAAGTGATCTTTTAT AAAGT (SEQ ID NO: 43) |

RFLP/TIDE Primers

| Target | Forward primer | Reverse primer |
|---|---|---|
| CCR5 | CTCCATGGTGCTATAGAG CA (SEQ ID NO: 44) | GCCCTGTCAAGAGTTGACAC (SEQ ID NO: 45) |
| CXCR4 | AGAGGAGTTAGCCAAGA TGTGACTTTGAAACC (SEQ ID NO: 46) | GGACAGGATGACAATACCAGGC AGGATAAGCC (SEQ ID NO: 47) |

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. The citation of any reference herein is not an admission that such reference is available as prior art to the instant invention.

FULL CITATIONS FOR PUBLICATIONS

1. Doudna, J. A. & Charpentier, E. Genome editing. The new frontier of genome engineering with CRISPR-Cas9. *Science* 346, 1258096 (2014).
2. Cox, D. B., Platt, R. J. & Zhang, F. Therapeutic genome editing: prospects and challenges. *Nat Med* 21, 121-131 (2015).
3. Chandrasegaran, S. & Carroll, D. Origins of Programmable Nucleases for Genome Engineering. *J Mol Biol* (2015).
4. Orthwein, A. et al. A mechanism for the suppression of homologous recombination in G1 cells. *Nature* 528, 422-426 (2015).
5. Panier, S. & Boulton, S. J. Double-strand break repair: 53BP1 comes into focus. *Nat Rev Mol Cell Biol* 15, 7-18 (2014).
6. Escribano-Diaz, C. et al. A Cell Cycle-Dependent Regulatory Circuit Composed of 53BP1-RIF1 and BRCA1-CtIP Controls DNA Repair Pathway Choice. *Molecular cell* 49, 872-883 (2013).
7. Ernst, A. et al. A strategy for modulation of enzymes in the ubiquitin system. *Science* 339, 590-595 (2013).
8. Lieber, M. R. The mechanism of double-strand DNA break repair by the nonhomologous DNA end joining pathway. *Annu Rev Biochem* 79, 181-211 (2010).
9. Symington, L. S. & Gautier, J. Double-strand break end resection and repair pathway choice. *Annual review of genetics* 45, 247-271 (2011).
10. Jackson, S. P. & Durocher, D. Regulation of DNA damage responses by ubiquitin and SUMO. *Molecular cell* 49, 795-807 (2013).
11. Chapman, J. R., Taylor, M. R. & Boulton, S. J. Playing the end game: DNA double-strand break repair pathway choice. *Molecular cell* 47, 497-510 (2012).
12. Feng, L., Fong, K. W., Wang, J., Wang, W. & Chen, J. RIF1 counteracts BRCA1-mediated end resection during DNA repair. *The Journal of biological chemistry* 288, 11135-11143 (2013).
13. Fradet-Turcotte, A. et al. 53BP1 is a reader of the DNA-damage-induced H2A Lys 15 ubiquitin mark. *Nature* 499, 50-54 (2013).
14. Botuyan, M. V. et al. Structural basis for the methylation state-specific recognition of histone H4-K20 by 53BP1 and Crb2 in DNA repair. *Cell* 127, 1361-1373 (2006).

15. Dikic, I., Wakatsuki, S. & Walters, K. J. Ubiquitin-binding domains—from structures to functions. *Nature reviews. Molecular cell biology* 10, 659-671 (2009).

16. Xie, A. et al. Distinct roles of chromatin-associated proteins MDC1 and 53BP1 in mammalian double-strand break repair. *Mol Cell* 28, 1045-1057 (2007).

17. Moynahan, M. E., Chiu, J. W., Koller, B. H. & Jasin, M. Brca1 controls homology-directed DNA repair. *Mol Cell* 4, 511-518 (1999).

18. Srivastava, M. et al. An inhibitor of nonhomologous end-joining abrogates double-strand break repair and impedes cancer progression. *Cell* 151, 1474-1487 (2012).

19. Chu, V. T. et al. Increasing the efficiency of homology-directed repair for CRISPR-Cas9-induced precise gene editing in mammalian cells. *Nat Biotechnol* 33, 543-548 (2015).

20. Maruyama, T. et al. Increasing the efficiency of precise genome editing with CRISPR-Cas9 by inhibition of nonhomologous end joining. *Nat Biotechnol* 33, 538-542 (2015).

21. Pinder, J., Salsman, J. & Dellaire, G. Nuclear domain 'knock-in' screen for the evaluation and identification of small molecule enhancers of CRISPR-based genome editing. *Nucleic Acids Res* (2015).

22. O'Donnell, L. et al. The MMS22L-TONSL complex mediates recovery from replication stress and homologous recombination. *Molecular cell* 40, 619-631 (2010).

23. Sfeir, A. & Symington, L. S. Microhomology-Mediated End Joining: A Back-up Survival Mechanism or Dedicated Pathway? *Trends Biochem Sci* 40, 701-714 (2015).

24. Gunn, A. & Stark, J. M. I-SceI-Based Assays to Examine Distinct Repair Outcomes of Mammalian Chromosomal Double Strand Breaks. *Methods Mol Biol* 920, 379-391 (2012).

25. Bennardo, N., Cheng, A., Huang, N. & Stark, J. M. Alternative-NHEJ is a mechanistically distinct pathway of mammalian chromosome break repair. *PLoS genetics* 4, e1000110 (2008).

26. Burt, A. Site-specific selfish genes as tools for the control and genetic engineering of natural populations. *Proceedings. Biological sciences/The Royal Society* 270, 921-928 (2003).

27. Nijnik, A. et al. DNA repair is limiting for haematopoietic stem cells during ageing. *Nature* 447, 686-690 (2007).

28. Chistiakov, D. A., Voronova, N. V. & Chistiakov, A. P. Ligase IV syndrome. *European journal of medical genetics* 52, 373-378 (2009).

29. Hart, T. et al. High-Resolution CRISPR Screens Reveal Fitness Genes and Genotype-Specific Cancer Liabilities. *Cell* 163, 1515-1526 (2015).

30. Sanjana, N. E., Shalem, O. & Zhang, F. Improved vectors and genome-wide libraries for CRISPR screening. *Nat Methods* 11, 783-784 (2014).

31. Tonikian, R., Zhang, Y., Boone, C. & Sidhu, S. S. Identifying specificity profiles for peptide recognition modules from phage-displayed peptide libraries. *Nat Protoc* 2, 1368-1386 (2007).

32. Gaëlle Charier et al, The Tudor Tandem of 53BP1: A New Structural Motif Involved in DNA and RG-Rich Peptide Binding, Structure, 12(9), 1551-1747, 2004

TABLE 1

Data collection and refinement statistics (molecular replacement)

| | 53BP1 Tudor Domain - Ubv08 |
|---|---|
| Data collection | |
| Space group | $P2_12_12_1$ |
| Cell dimensions | |
| a, b, c (Å) | 39.5, 47.8, 94.2 |
| α, β, γ (°) | 90.0, 90.0, 90.0 |
| Resolution (Å) | 50.0-2.50 (2.65-2.50)* |
| $R_{merge}$ | 0.071 (0.40) |
| I/σI | 11.5 (1.75) |
| CC (½) | 99.6 (78.2) |
| Completeness (%) | 87.6 (49.1) |
| Redundancy | 1.74 (1.16) |
| Refinement | |
| Resolution (Å) | 24.6-2.50 |
| No. reflections | 6047 |
| $R_{work}/R_{free}$ | 23.2/27.8 |
| No. atoms | |
| Protein | 1523 |
| Water | 1 |
| Average B-factor | 44.44 |
| R.m.s. deviations | |
| Bond lengths (Å) | 0.002 |
| Bond angles (°) | 0.597 |
| Ramachandran Plot | |
| Outliers | 0.00 |
| Allowed | 2.20 |
| Favored | 97.8 |

Structure was determined from a single crystal
*Values in parentheses are for highest-resolution shell.

$R_{sym} = \Sigma_h \Sigma_i |I_{h,i} - I_h|/\Sigma_h \Sigma_i I_{h,i}$, where $I_h$ is the mean intensity of the i observations of symmetry related reflections of h. $R = \Sigma |F_{obs} - F_{calc}|/\Sigma F_{obs}$, where $F_{obs} = F_P$ and $F_{calc}$ is the calculated protein structure factor from the atomic model.

TABLE 2

The i53 protein binds selectively to 53BP1. Protein identified in Flag immunoprecipitates (IPs) from extracts derived from 293T Flp-In/T-Rex cells expressing Flag-i53 and Flag-i53-DM. Three additional IPs from extracts from a line expressing only Flag were performed. The list of identified proteins was filtered first by removing protein with <2 unique peptides and those in an annotated "frequent flier" set. The Ub-matching peptides of RPS27 were also identified but since the bait was homologous to Ub, RPS27 was removed from the list. All proteins identified in the IPs were then removed from the Flag-only cell line. TP53BP1 is 53BP1.

| | | | Bait: Flag-i53 | | Bait: Flag-i53-DM |
|---|---|---|---|---|---|
| Gene ID | Gene Name | Protein ID | Total peptides | | |
| 7158 | TP53BP1 | 213972634 | 66 | 38 | 21 |
| 1072 | CFL1 | 5031635 | 6 | | |
| 2935 | GSPT1 | 194018520 | 3 | | |
| 830 | CAPZA2 | 5453599 | | 7 | |
| 6152 | RPL24 | 4506619 | | 5 | 5 |
| 8339 | HIST1H2BG | 4504257 | | 4 | |
| 4673 | NAP1L1 | 4758756 | | 4 | |
| 5245 | PHB | 4505773 | | 2 | |
| 6229 | RPS24 | 4506703 | | | 4 |
| 11078 | TRIOBP | 88501738 | | | 3 |
| 10765 | KDM5B | 57242796 | | | 3 |
| 84364 | ARFGAP2 | 31543983 | | | 3 |
| 51060 | TXNDC12 | 7705696 | | | 2 |
| 26292 | MYCBP | 57242777 | | 7 | 5 |
| 6139 | RPL17 | 313569778 | | 5 | |
| 6134 | RPL10 | 223890243 | | | 11 |
| 2332 | FMR1 | 297374791 | | | 6 |
| 6132 | RPL8 | 4506663 | | | 5 |
| 54832 | VPS13C | 66348091 | | | 5 |

TABLE 2-continued

The i53 protein binds selectively to 53BP1. Protein identified in Flag immunoprecipitates (IPs) from extracts derived from 293T Flp-In/T-Rex cells expressing Flag-i53 and Flag-i53-DM. Three additional IPs from extracts from a line expressing only Flag were performed. The list of identified proteins was filtered first by removing protein with <2 unique peptides and those in an annotated "frequent flier" set. The Ub-matching peptides of RPS27 were also identified but since the bait was homologous to Ub, RPS27 was removed from the list. All proteins identified in the IPs were then removed from the Flag-only cell line. TP53BP1 is 53BP1.

| Gene ID | Gene Name | Protein ID | Bait: Flag-i53 | Bait: Flag-i53-DM |
|---|---|---|---|---|
| | | | Total peptides | |
| 80217 | WDR96 | 94681049 | 4 | |
| 3853 | KRT6A | 5031839 | 3 | |
| 494115 | RBMXL1 | 21361809 | 3 | |
| 6159 | RPL29 | 4506629 | 3 | |
| 8349 | HIST2H2BE | 4504277 | 3 | |
| 54970 | TTC12 | 90669931 | 3 | |
| 6235 | RPS29 | 4506717 | 3 | |
| 65123 | INTS3 | 39995084 | 3 | |
| 23269 | MGA | 256017159 | 2 | |
| 79785 | RERGL | 13376046 | 2 | |
| 83871 | RAB34 | 222144313 | 2 | |
| 9940 | DLEC1 | 90669194 | 2 | |

TABLE 3

| SEQ ID NO | Nucleic Acid Sequences |
|---|---|
| 12 | Ubiquitin (wild type) DNA sequence<br>ATGCAGATTTTCGTGAAAACCCTTACGGGGAAGACCATCACC<br>CTCGAGGTTGAACCCTCGGATACGATAGAAAATGTAAAGGC<br>CAAGATCCAGGATAAGGAAGGAATTCCTCCTGATCAGCAGA<br>GACTGATCTTTGCTGGCAAGCAGCTGGAAGATGGACGTACTT<br>TGTCTGACTACAATATTCAAAAGGAGTCTACTCTTCATCTTG<br>TGTTGAGACTTCGTGGTGGT |
| 13 | Ubiquitin (wild type) RNA sequence<br>AUGCAGAUUUUCGUGAAAACCCUUACGGGGAAGACCAUCA<br>CCCUCGAGGUUGAACCCUCGGAUACGAUAGAAAAUGUAAA<br>GGCCAAGAUCCAGGAUAAGGAAGGAAUUCCUCCUGAUCAG<br>CAGAGACUGAUCUUUGCUGGCAAGCAGCUGGAAGAUGGAC<br>GUACUUUGUCUGACUACAAUAUUCAAAAGGAGUCUACUCU<br>UCAUCUUGUGUUGAGACUUCGUGGUGGU |
| 14 | UbvA10 DNA sequence<br>ATGCAGATTTACGTGAAGACCTTTGCCCGGAAGCCCATCACC<br>CTCGAGGTTGAACCCTCGGATACGATAGAAAATGTAAAGGC<br>CAAGATCCAGGATAAGGAAGGAATTCCTCCTGATCAGCAGC<br>GACTGATCTTTGCTGAAATGCGGCTGGAAGATGGACGTACTT<br>TGTCTGACTACAATATTAAAAACGACTCTACTCTTTTTCTTGT<br>GTTGAAAAATAGTGTTACT |
| 15 | UbvA10 RNA sequence<br>AUGCAGAUUUACGUGAAGACCUUUGCCCGGAAGCCCAUCA<br>CCCUCGAGGUUGAACCCUCGGAUACGAUAGAAAAUGUAAA<br>GGCCAAGAUCCAGGAUAAGGAAGGAAUUCCUCCUGAUCAG<br>CAGCGACUGAUCUUUGCUGAAAUGCGGCUGGAAGAUGGAC<br>GUACUUUGUCUGACUACAAUAUUAAAAACGACUCUACUCU<br>UUUUCUUGUGUUGAAAAAUAGUGUUACU |
| 16 | UbvA11 DNA sequence<br>ATGCTGATTTTCGTGACCACCGATATGGGGATGACAATCTCA<br>CTCGAGGTTGAACCCTCGGATACGATAGAAAATGTAAAGGC<br>CAAGATCCAGGATAAGGAAGGAATTCCTCCTGATCAGCAGA<br>GACTGATCTTTGGTGACAAGGATCTGGAAGATGGACGTACTT<br>TGTCTGACTACAATATTCAAAAGGAGTCTAGCCTTAATCTTG<br>TGCTGAACTTCGTGGTGGT |
| 17 | UbvA11 RNA sequence<br>AUGCUGAUUUUCGUGACCACCGAUAUGGGGAUGACAAUCU<br>CACUCGAGGUUGAACCCUCGGAUACGAUAGAAAAUGUAAA<br>GGCCAAGAUCCAGGAUAAGGAAGGAAUUCCUCCUGAUCAG<br>CAGAGACUGAUCUUUGGUGACAAGGAUCUGGAAGAUGGAC<br>GUACUUUGUCUGACUACAAUAUUCAAAAGGAGUCUAGCCU<br>UAAUCUUGUGCUGAACUUCGUGGUGGU |
| 18 | UbvC08 DNA sequence<br>ATGCAGATTTTCGTGACCACCGATATGTGGATGAGAATCTCA<br>CTCGAGGTTGAACCCTCGGATACGATAGAAAATGTAAAGGC<br>CAAGATCCAGGATAAGGAAGGAATTCCTCCTGATCAGCAGA<br>GACTGATCTTTGGTGACAAGGATCTGGAAGATGGACGTACTT<br>TGTCTGACTACAATATTCAAAAGGAGTCTAGCCTTAATCTTG<br>TGCTGAACCTTCGTGGTGGT |
| 19 | UbvC08 RNA sequence<br>AUGCAGAUUUUCGUGACCACCGAUAUGUGGAUGAGAAUCU<br>CACUCGAGGUUGAACCCUCGGAUACGAUAGAAAAUGUAAA<br>GGCCAAGAUCCAGGAUAAGGAAGGAAUUCCUCCUGAUCAG<br>CAGAGACUGAUCUUUGGUGACAAGGAUCUGGAAGAUGGAC<br>GUACUUUGUCUGACUACAAUAUUCAAAAGGAGUCUAGCCU<br>UAAUCUUGUGCUGAACCUUCGUGGUGGU |
| 20 | UbvG08 DNA sequence<br>ATGTTGATTTTCGTGAAACCCTTACCGGGAAACCATCACC<br>CTCGAGGTTGAACCCTCGGATACGATAGAAAATGTAAAGGC<br>CAAGATCCAGGATAAGGAAGGAATTCCTCCTGATCAGCAGA<br>GACTGATCTTTGCTGGCAAATCGCTGGAAGATGGACGTACTT<br>TGTCTGACTACAATATTCTAAAGGACTCTAAACTTCATCCTC<br>TGTTGAGACTTCGTGGTGGT |
| 21 | UbvG08 RNA sequence<br>AUGUUGAUUUUCGUGAAACCCUUACCGGGAAACCAUCA<br>CCCUCGAGGUUGAACCCUCGGAUACGAUAGAAAAUGUAAA<br>GGCCAAGAUCCAGGAUAAGGAAGGAAUUCCUCCUGAUCAG<br>CAGAGACUGAUCUUUGCUGGCAAAUCGCUGGAAGAUGGAC<br>GUACUUUGUCUGACUACAAUAUUCUAAAGGACUCUAAACU<br>UCAUCCUCUGUUGAGACUUCGUGGUGGU |
| 22 | UbvH04 DNA sequence<br>ATGCGAATTATCGTGAAAACCTTTATGCGGAAGCCGATCACG<br>CTCGAGGTTGAACCCTCGGATACGATAGAAAATGTAAAGGC<br>CAAGATCCAGGATAAGGAAGGAATTCCTCCTGATCAGCAGA<br>GACTGTATTTTGCGCCAGTCAGCTGGAAGATGGACGTACTT<br>TGTCTGACTACAATATTCAAAAGGAGTCTACTCTTCTTCTTGT<br>GGTAAGGCTGCTCCGCGTT |
| 23 | UbvH04 RNA sequence<br>AUGCGAAUUAUCGUGAAAACCUUUAUGCGGAAGCCGAUCA<br>CGCUCGAGGUUGAACCCUCGGAUACGAUAGAAAAUGUAAA<br>GGCCAAGAUCCAGGAUAAGGAAGGAAUUCCUCCUGAUCAG<br>CAGAGACUGUAUUUUGCGCCAGUCAGCUGGAAGAUGGAC<br>GUACUUUGUCUGACUACAAUAUUCAAAAGGAGUCUACUCU<br>UCUUCUUGUGGUAAGGCUGCUCCGCGUU |
| 24 | i53 DNA sequence<br>ATGTTGATTTTCGTGAAAACCCTTACCGGGAAAACCATCACC<br>CTCGAGGTTGAACCCTCGGATACGATAGAAAATGTAAAGGC<br>CAAGATCCAGGATAAGGAAGGAATTCCTCCTGATCAGCAGA<br>GACTGGCCTTTGCTGGCAAATCGCTGGAAGATGGACGTACTT<br>TGTCTGACTACAATATTCTAAAGGACTCTAAACTTCATCCTC<br>TGTTGAGACTTCGT |
| 25 | i53 RNA sequence<br>AUGUUGAUUUUCGUGAAAACCCUUACCGGGAAAACCAUCA<br>CCCUCGAGGUUGAACCCUCGGAUACGAUAGAAAAUGUAAA<br>GGCCAAGAUCCAGGAUAAGGAAGGAAUUCCUCCUGAUCAG<br>CAGAGACUGGCCUUUGCUGGCAAAUCGCUGGAAGAUGGAC<br>GUACUUUGUCUGACUACAAUAUUCUAAAGGACUCUAAACU<br>UCAUCCUCUGUUGAGACUUCGU |
| 49 | UbvG08-DM RNA:<br>AUGUUGAUUUUCGUGAAAACCCUUACCGGGAAAACCAUCA<br>CCCUCGAGGUUGAACCCUCGGAUACGAUAGAAAAUGUAAA<br>GGCCAAGAUCCAGGAUAAGGAAGGAAUUCCUCCUGAUCAG<br>CAGAGACUGAUCUUUGCUGGCAAAUCGCUGGAAGAUGGAC<br>GUACUUUGUCUGACUACAAUAUUCUAAAGGACUCUAAACU<br>UCAUCUAGUGUUGAGACUUCGUGGUGGU |

TABLE 3-continued

| SEQ ID NO | Nucleic Acid Sequences |
|---|---|
| 50 | i53-DM RNA<br>AUGUUGAUUUUCGUGAAAACCCUUACCGGGAAAACCAUCA<br>CCCUCGAGGUUGAACCCUCGGAUACGAUAGAAAAUGUAAA<br>GGCCAAGAUCCAGGAUAAGGAAGGAAUUCCUCCUGAUCAG |
| | CAGAGACUGGCCUUUGCUGGCAAAUCGCUGGAAGAUGGAC<br>GUACUUUGUCUGACUACAAUAUUCUAAAGGACUCUAAACU<br>UCAUCUAGUGUUGAGACUUCGU |

---

What is claimed is:

1. A polypeptide comprising the amino acid sequence of SEQ ID NO: 1 having the following modifications:
   (a) a Leu at positions 2 and 62 of SEQ ID NO: 1, an Asp at position 64 of SEQ ID NO: 1, a Lys at position 66 of SEQ ID NO: 1, and a Pro at position 69 of SEQ ID NO: 1;
   (b) a Leu at positions 2, 62 and/or 70 of SEQ ID NO: 1, an Asp at position 64 of SEQ ID NO: 1, a Lys at position 66 of SEQ ID NO: 1, and a Pro at position 69 of SEQ ID NO: 1;
   (c) a Leu at position 2 of SEQ ID NO: 1, an Asp at position 64 of SEQ ID NO: 1, a Lys at position 66 of SEQ ID NO: 1, and a Pro at position 69 of SEQ ID NO: 1;
   (d) a Leu at positions 2, 62 and 70 of SEQ ID NO: 1, an Ala at position 44 of SEQ ID NO: 1, an Asp at position 64 of SEQ ID NO: 1, a Lys at position 66 of SEQ ID NO: 1, and a Pro at position 69 of SEQ ID NO: 1;
   (e) a Leu at positions 2 and 62 of SEQ ID NO: 1, an Asp at position 64 of SEQ ID NO: 1, and a Lys at position 66 of SEQ ID NO: 1;
   (f) a Leu at positions 2 and 62 of SEQ ID NO:1, a Ser at position 49 of SEQ ID NO: 1, an Asp at position 64 of SEQ ID NO: 1, and a Lys at position 66 of SEQ ID NO: 1;
   (g) a Leu at one or more of positions 2, 62 and 70 of SEQ ID NO: 1, an Ala at position 44 of SEQ ID NO: 1, an Asp at position 64 of SEQ ID NO: 1, a Lys at position 66 of SEQ ID NO: 1, and a Pro at position 69 of SEQ ID NO: 1;
   (h) a Leu at positions 2, 62 and 70 of SEQ ID NO: 1, an Ala at position 44 of SEQ ID NO: 1, an Asp at position 64 of SEQ ID NO: 1, a Lys at position 66 of SEQ ID NO: 1, and a Pro at position 69 of SEQ ID NO: 1;
   (i) a Leu at positions 2, 62 and 70 of SEQ ID NO: 1, an Ala at position 44 of SEQ ID NO: 1, a Ser at position 49 of SEQ ID NO: 1, an Asp at position 64 of SEQ ID NO: 1, a Lys at position 66 of SEQ ID NO: 1, and a Pro at position 69 of SEQ ID NO: 1;
   (j) a Leu at position 2 of SEQ ID NO: 1, a Thr at position 6 of SEQ ID NO: 1, an Asp at positions 8, 47 and/or 49 of SEQ ID NO: 1, a Met at positions 9 and/or 11 of SEQ ID NO: 1, a Ser at positions 14 and/or 66 of SEQ ID NO: 1, a Gly at position 46 of SEQ ID NO: 1, an Asn at position 68 of SEQ ID NO: 1, and a Lys at position 72 of SEQ ID NO: 1;
   (k) a Tyr at position 4 of SEQ ID NO: 1, a Phe at positions 8 and/or 68 of SEQ ID NO: 1, an Ala at position 9 of SEQ ID NO: 1, an Arg at positions 10 and/or 49 of SEQ ID NO: 1, a Pro at position 12 of SEQ ID NO:1, a Glu at position 47 of SEQ ID NO: 1, a Met at position 48 of SEQ ID NO: 1, a Lys at positions 62 and/or 72 of SEQ ID NO: 1, an Asn at positions 63 and/or 73 of SEQ ID NO: 1, an Asp at position 64 of SEQ ID NO: 1, a Ser at position 74 of SEQ ID NO: 1, a Val at position 75 of SEQ ID NO: 1, and a Thr at position 76 of SEQ ID NO: 1;
   (l) a Thr at position 6 of SEQ ID NO: 1, an Asp at positions 8, 47 and/or 49 of SEQ ID NO: 1, a Met at positions 9 and/or 11 of SEQ ID NO: 1, a Trp at position 10 of SEQ ID NO: 1, an Arg at position 12 of SEQ ID NO: 1, a Gly at position 46 of SEQ ID NO: 1, a Ser at positions 14 and/or 66 of SEQ ID NO: 1, an Asn at positions 68 and/or 72 of SEQ ID NO: 1;
   (m) an Arg at positions 2 and/or 75 of SEQ ID NO: 1, an Ile at position 4 of SEQ ID NO: 1, a Phe at position 8 of SEQ ID NO: 1, a Met at position 9 of SEQ ID NO: 1, a Pro at position 12 of SEQ ID NO: 1, a Tyr at position 44 of SEQ ID NO: 1, a Ala at position 47 of SEQ ID NO: 1, a Ser at position 48 of SEQ ID NO: 1, a Leu at positions 68 and/or 74 of SEQ ID NO: 1, and a Val at positions 71 and/or 76; or
   (n) the modifications as set forth in any one of (a)-(j), (l), or (m), and further comprising the following modification: Gly76 is absent or Gly75 and Gly76 are absent.

2. A polynucleotide encoding the polypeptide of claim 1.

3. A cell or cell line comprising the polypeptide of claim 1.

4. A composition comprising the polypeptide of claim 1 in admixture with a carrier, excipient or diluent.

5. A composition comprising the polypeptide of claim 1 and one or more of the following: 1) an inhibitor of RIF expression or activity or a CtIP compound that mimics constitutive phosphorylation; 2) one or more factors that maintain BRCA1-PALB2 interactions during the cell cycle; and, 3) one or more components of a gene editing system.

6. The composition of claim 5, wherein the inhibitor of RIF expression or activity is an inhibitor of RIF1 expression or activity.

7. The composition of claim 5, wherein the gene editing system is a CRISPR system.

8. A kit comprising the polypeptide of claim 1.

9. A method of suppressing 53BP1 recruitment to DNA double-strand break sites in a cell comprising administering to the cell the polypeptide of claim 1.

10. A method of increasing homologous recombination in a cell comprising administering to the cell the polypeptide of claim 1.

11. A method of editing a gene in a cell using a CRISPR system comprising administering to the cell the polypeptide of claim 1.

12. A method of increasing gene targeting in a cell comprising administering to the cell the polypeptide of claim 1 in combination with an inhibitor of DNA-PK.

13. A polypeptide comprising the amino acid sequence of SEQ ID NO: 2, 3, 4, 5, 6, 7, 8, 9, 10 or 11.

14. A composition comprising the polypeptide of claim 13 in admixture with a carrier, excipient or diluent.

15. A composition comprising the polypeptide of claim 13 and one or more of the following: 1) an inhibitor of RIF expression or activity or a CtIP compound that mimics constitutive phosphorylation; 2) one or more factors that maintain BRCA1-PALB2 interactions during the cell cycle; and, 3) one or more components of a gene editing system.

16. A kit comprising the polypeptide of claim 13.

17. The polypeptide of claim 13 comprising the amino acid sequence of SEQ ID NO: 9.

18. A method of increasing homologous recombination in a cell comprising administering to the cell the polypeptide of claim 13.

19. A method of editing a gene in a cell using a CRISPR system comprising administering to the cell the polypeptide of claim 13.

20. A method of increasing gene targeting in a cell comprising administering to the cell the polypeptide of claim 13 in combination with an inhibitor of DNA-PK.

21. A polynucleotide comprising the nucleic acid sequence of SEQ ID NO: 14, 15, 16, 17, 18, 19, 20, 21, 22, 23, 24, 25, 49 or 50.

22. A vector comprising the polynucleotide of claim 21.

23. A kit comprising the vector of claim 22 and one or more of the following components: 1) an inhibitor of RIF expression or activity or a CtIP compound that mimics constitutive phosphorylation; 2) one or more factors that maintain BRCA1-PALB2 interactions during the cell cycle; and, 3) one or more components of a gene editing system.

24. A kit of claim 23 wherein the gene editing system is a CRISPR system.

* * * * *

SEQUENCE LISTING

<160> NUMBER OF SEQ ID NOS: 51

<210> SEQ ID NO 1
<211> LENGTH: 76
<212> TYPE: PRT
<213> ORGANISM: Homo sapiens

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 2
<211> LENGTH: 76
<212> TYPE: PRT
<213> ORGANISM: Artificial Sequence
<220> FEATURE:
<223> OTHER INFORMATION: Constructed sequence

<400> SEQUENCE: 2

Met Gln Ile Tyr Val Lys Thr Phe Ala Arg Lys Pro Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Glu Met
        35                  40                  45

Arg Leu Glu Asp Gly Arg Thr Leu Ser Asp Tyr Asn Ile Lys Asn Asp
    50                  55                  60

Ser Thr Leu Phe Leu Val Leu Lys Asn Ser Val Thr
65                  70                  75

<210> SEQ ID NO 3
<211> LENGTH: 76
<212> TYPE: PRT
<213> ORGANISM: Artificial Sequence
<220> FEATURE:
<223> OTHER INFORMATION: Constructed sequence

<400> SEQUENCE: 3

Met Leu Ile Phe Val Thr Thr Asp Met Gly Met Thr Ile Ser Leu Glu
1               5                   10                  15

Val Glu Pro Ser Asp Thr Ile Glu Asn Val Lys Ala Lys Ile Gln Asp
            20                  25                  30

-continued

Lys Glu Gly Ile Pro Pro Asp Gln Gln Arg Leu Ile Phe Gly Asp Lys
            35                  40                  45

Asp Leu Glu Asp Gly Arg Thr Leu Ser Asp Tyr Asn Ile Gln Lys Glu
 50                  55                  60

Ser Ser Leu Asn Leu Val Leu Lys Leu Arg Gly Gly
 65                  70                  75

<210> SEQ ID NO 4
<211> LENGTH: 76
<212> TYPE: PRT
<213> ORGANISM: Artificial Sequence
<220> FEATURE:
<223> OTHER INFORMATION: Constructed sequence

<400> SEQUENCE: 4

Met Gln Ile Phe Val Thr Thr Asp Met Trp Met Arg Ile Ser Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Gly Asp Lys
            35                  40                  45

Asp Leu Glu Asp Gly Arg Thr Leu Ser Asp Tyr Asn Ile Gln Lys Glu
 50                  55                  60

Ser Ser Leu Asn Leu Val Leu Asn Leu Arg Gly Gly
 65                  70                  75

<210> SEQ ID NO 5
<211> LENGTH: 76
<212> TYPE: PRT
<213> ORGANISM: Artificial Sequence
<220> FEATURE:
<223> OTHER INFORMATION: Constructed sequence

<400> SEQUENCE: 5

Met Leu Ile Phe Val Lys Thr Leu Thr Gly Lys Thr Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
            35                  40                  45

Ser Leu Glu Asp Gly Arg Thr Leu Ser Asp Tyr Asn Ile Leu Lys Asp
 50                  55                  60

Ser Lys Leu His Pro Leu Leu Arg Leu Arg Gly Gly
 65                  70                  75

<210> SEQ ID NO 6
<211> LENGTH: 76
<212> TYPE: PRT
<213> ORGANISM: Artificial Sequence
<220> FEATURE:
<223> OTHER INFORMATION: Constructed sequence

<400> SEQUENCE: 6

Met Arg Ile Ile Val Lys Thr Phe Met Arg Lys Pro Ile Thr Leu Glu
 1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Tyr Phe Ala Ala Ser
            35                  40                  45

```
Gln Leu Glu Asp Gly Arg Thr Leu Ser Asp Tyr Asn Ile Gln Lys Glu
 50                  55                  60

Ser Thr Leu Leu Leu Val Val Arg Leu Leu Arg Val
 65                  70                  75
```

<210> SEQ ID NO 7
<211> LENGTH: 74
<212> TYPE: PRT
<213> ORGANISM: Artificial Sequence
<220> FEATURE:
<223> OTHER INFORMATION: Constructed sequence

<400> SEQUENCE: 7

```
Met Leu Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ile Phe Ala Gly Lys
             35                  40                  45

Ser Leu Glu Asp Gly Arg Thr Leu Ser Asp Tyr Asn Ile Leu Lys Asp
 50                  55                  60

Ser Lys Leu His Pro Leu Leu Arg Leu Arg
 65                  70
```

<210> SEQ ID NO 8
<211> LENGTH: 76
<212> TYPE: PRT
<213> ORGANISM: Artificial Sequence
<220> FEATURE:
<223> OTHER INFORMATION: Constructed sequence

<400> SEQUENCE: 8

```
Met Leu Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ala Phe Ala Gly Lys
             35                  40                  45

Ser Leu Glu Asp Gly Arg Thr Leu Ser Asp Tyr Asn Ile Leu Lys Asp
 50                  55                  60

Ser Lys Leu His Pro Leu Leu Arg Leu Arg Gly Gly
 65                  70                  75
```

<210> SEQ ID NO 9
<211> LENGTH: 74
<212> TYPE: PRT
<213> ORGANISM: Artificial Sequence
<220> FEATURE:
<223> OTHER INFORMATION: Constructed peptide

<400> SEQUENCE: 9

```
Met Leu Ile Phe Val Lys Thr Leu Thr Gly Lys Thr Ile Thr Leu Glu
  1               5                  10                  15

Val Glu Pro Ser Asp Thr Ile Glu Asn Val Lys Ala Lys Ile Gln Asp
                 20                  25                  30

Lys Glu Gly Ile Pro Pro Asp Gln Gln Arg Leu Ala Phe Ala Gly Lys
             35                  40                  45

Ser Leu Glu Asp Gly Arg Thr Leu Ser Asp Tyr Asn Ile Leu Lys Asp
 50                  55                  60

Ser Lys Leu His Pro Leu Leu Arg Leu Arg
 65                  70
```

<210> SEQ ID NO 10
<211> LENGTH: 76
<212> TYPE: PRT
<213> ORGANISM: Artificial Sequence
<220> FEATURE:
<223> OTHER INFORMATION: constructed sequence

<400> SEQUENCE: 10

Met Leu Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Ser Leu Glu Asp Gly Arg Thr Leu Ser Asp Tyr Asn Ile Leu Lys Asp
    50                  55                  60

Ser Lys Leu His Leu Val Leu Arg Leu Arg Gly Gly
65                  70                  75

<210> SEQ ID NO 11
<211> LENGTH: 74
<212> TYPE: PRT
<213> ORGANISM: Artificial Sequence
<220> FEATURE:
<223> OTHER INFORMATION: constructed sequence

<400> SEQUENCE: 11

Met Leu Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ala Phe Ala Gly Lys
        35                  40                  45

Ser Leu Glu Asp Gly Arg Thr Leu Ser Asp Tyr Asn Ile Leu Lys Asp
    50                  55                  60

Ser Lys Leu His Leu Val Leu Arg Leu Arg
65                  70

<210> SEQ ID NO 12
<211> LENGTH: 228
<212> TYPE: DNA
<213> ORGANISM: Homo sapiens

<400> SEQUENCE: 12
atgcagattt tcgtgaaaac ccttacgggg aagaccatca ccctcgaggt tgaaccctcg      60
gatacgatag aaaatgtaaa ggccaagatc caggataagg aaggaattcc tcctgatcag     120
cagagactga tctttgctgg caagcagctg gaagatggac gtactttgtc tgactacaat     180
attcaaaagg agtctactct tcatcttgtg ttgagacttc gtggtggt                  228

<210> SEQ ID NO 13
<211> LENGTH: 228
<212> TYPE: RNA
<213> ORGANISM: Homo sapiens

<400> SEQUENCE: 13
augcagauuu ucgugaaaac ccuuacgggg aagaccauca cccucgaggu ugaacccucg      60
gauacgauag aaaauguaaa ggccaagauc caggauaagg aaggaauucc uccugaucag     120
cagagacuga ucuuugcugg caagcagcug gaagauggac guacuuuguc ugacuacaau    180
auucaaaagg agucuacucu ucaucuugug uugagacuuc gugguggu                228

<210> SEQ ID NO 14
<211> LENGTH: 228
<212> TYPE: DNA
<213> ORGANISM: Artificial Sequence
<220> FEATURE:
<223> OTHER INFORMATION: constructed sequence

<400> SEQUENCE: 14
atgcagattt acgtgaagac ctttgcccgg aagcccatca ccctcgaggt tgaaccctcg    60
gatacgatag aaaatgtaaa ggccaagatc caggataagg aaggaattcc tcctgatcag    120
cagcgactga tctttgctga aatgcggctg aagatggac gtactttgtc tgactacaat    180
attaaaaacg actctactct ttttcttgtg ttgaaaaata gtgttact                228

<210> SEQ ID NO 15
<211> LENGTH: 228
<212> TYPE: RNA
<213> ORGANISM: Artificial Sequence
<220> FEATURE:
<223> OTHER INFORMATION: constructed sequence

<400> SEQUENCE: 15
augcagauuu acgugaagac cuuugcccgg aagcccauca cccucgaggu ugaacccucg    60
gauacgauag aaaauguaaa ggccaagauc caggauaagg aaggaauucc uccugaucag    120
cagcgacuga ucuuugcuga aaugcggcug aagauggac guacuuuguc ugacuacaau    180
auuaaaaacg acucuacucu uuuucuugug uugaaaaaua guguuacu                228

<210> SEQ ID NO 16
<211> LENGTH: 228
<212> TYPE: DNA
<213> ORGANISM: Artificial Sequence
<220> FEATURE:
<223> OTHER INFORMATION: constructed sequence

<400> SEQUENCE: 16
atgctgattt tcgtgaccac cgatatgggg atgacaatct cactcgaggt tgaaccctcg    60
gatacgatag aaaatgtaaa ggccaagatc caggataagg aaggaattcc tcctgatcag    120
cagagactga tctttggtga caaggatctg gaagatggac gtactttgtc tgactacaat    180
attcaaaagg agtctagcct taatcttgtg ctgaaacttc gtggtggt                228

<210> SEQ ID NO 17
<211> LENGTH: 228
<212> TYPE: RNA
<213> ORGANISM: Artificial Sequence
<220> FEATURE:
<223> OTHER INFORMATION: constructed sequence

<400> SEQUENCE: 17
augcugauuu ucgugaccac cgauaugggg augacaaucu cacucgaggu ugaacccucg    60
gauacgauag aaaauguaaa ggccaagauc caggauaagg aaggaauucc uccugaucag    120
cagagacuga ucuuuggüga caaggaucug gaagauggac guacuuuguc ugacuacaau    180
auucaaaagg agucuagccu uaaucuugug cugaaacuuc gugguggu                228

<210> SEQ ID NO 18

```
<211> LENGTH: 228
<212> TYPE: DNA
<213> ORGANISM: Artificial Sequence
<220> FEATURE:
<223> OTHER INFORMATION: constructed sequence

<400> SEQUENCE: 18
atgcagattt tcgtgaccac cgatatgtgg atgagaatct cactcgaggt tgaaccctcg      60
gatacgatag aaaatgtaaa ggccaagatc caggataagg aaggaattcc tcctgatcag     120
cagagactga tctttggtga caaggatctg gaagatggac gtactttgtc tgactacaat     180
attcaaaagg agtctagcct taatcttgtg ctgaaccttc gtggtggt                  228

<210> SEQ ID NO 19
<211> LENGTH: 228
<212> TYPE: RNA
<213> ORGANISM: Artificial Sequence
<220> FEATURE:
<223> OTHER INFORMATION: constructed sequence

<400> SEQUENCE: 19
augcagauuu ucgugaccac cgauaugugg augagaaucu cacucgaggu ugacccucg       60 gauacgauag aaaauguaaa ggccaagauc caggauaagg aaggaauucc uccugaucag     120
cagagacuga ucuuuggugu caaggaucug gaagauggac guacuuuguc ugacuacaau     180
auucaaaagg agucuagccu uaaucuugug cugaaccuuc gugguggu                  228

<210> SEQ ID NO 20
<211> LENGTH: 228
<212> TYPE: DNA
<213> ORGANISM: Artificial Sequence
<220> FEATURE:
<223> OTHER INFORMATION: constructed sequence

<400> SEQUENCE: 20
atgttgattt tcgtgaaaac ccttaccggg aaaaccatca ccctcgaggt tgaaccctcg      60
gatacgatag aaaatgtaaa ggccaagatc caggataagg aaggaattcc tcctgatcag     120
cagagactga tctttgctgg caaatcgctg gaagatggac gtactttgtc tgactacaat     180
attctaaagg actctaaact tcatcctctg ttgagacttc gtggtggt                  228

<210> SEQ ID NO 21
<211> LENGTH: 228
<212> TYPE: RNA
<213> ORGANISM: Artificial Sequence
<220> FEATURE:
<223> OTHER INFORMATION: constructed sequence

<400> SEQUENCE: 21
auguugauuu ucgugaaaac ccuuaccggg aaaaccauca cccucgaggu ugaacccucg      60
gauacgauag aaaauguaaa ggccaagauc caggauaagg aaggaauucc uccugaucag     120
cagagacuga ucuuugcugg caaaucgcug gaagauggac guacuuuguc ugacuacaau     180
auucuaaagg acucuaaacu ucauccucug uugagacuuc gugguggu                  228

<210> SEQ ID NO 22
<211> LENGTH: 228
<212> TYPE: DNA
<213> ORGANISM: Artificial Sequence
<220> FEATURE:
<223> OTHER INFORMATION: constructed sequence

<400> SEQUENCE: 22
```

-continued

```
atgcgaatta tcgtgaaaac ctttatgcgg aagccgatca cgctcgaggt tgaaccctcg    60
gatacgatag aaaatgtaaa ggccaagatc caggataagg aaggaattcc tcctgatcag   120
cagagactgt attttgcggc cagtcagctg gaagatggac gtactttgtc tgactacaat   180
attcaaaagg agtctactct tcttcttgtg gtaaggctgc tccgcgtt               228
```

<210> SEQ ID NO 23
<211> LENGTH: 228
<212> TYPE: RNA
<213> ORGANISM: Artificial Sequence
<220> FEATURE:
<223> OTHER INFORMATION: constructed sequence

<400> SEQUENCE: 23

```
augcgaauua ucgugaaaac cuuuaugcgg aagccgauca cgcucgaggu ugaacccucg    60
gauacgauag aaaauguaaa ggccaagauc caggauaagg aaggaauucc uccugaucag   120
cagagacugu auuuugcggc cagucagcug gaagauggac guacuuuguc ugacuacaau   180
auucaaaagg agucuacucu ucuucuugug guaaggcugc uccgcguu               228
```

<210> SEQ ID NO 24
<211> LENGTH: 222
<212> TYPE: DNA
<213> ORGANISM: Artificial Sequence
<220> FEATURE:
<223> OTHER INFORMATION: constructed sequence

<400> SEQUENCE: 24

```
atgttgattt tcgtgaaaac ccttaccggg aaaaccatca ccctcgaggt tgaaccctcg    60
gatacgatag aaaatgtaaa ggccaagatc caggataagg aaggaattcc tcctgatcag   120
cagagactgg cctttgctgg caaatcgctg gaagatggac gtactttgtc tgactacaat   180
attctaaagg actctaaact tcatcctctg ttgagacttc gt                    222
```

<210> SEQ ID NO 25
<211> LENGTH: 222
<212> TYPE: RNA
<213> ORGANISM: Artificial Sequence
<220> FEATURE:
<223> OTHER INFORMATION: constructed sequence

<400> SEQUENCE: 25

```
auguugauuu ucgugaaaac ccuuaccggg aaaaccauca cccucgaggu ugaacccucg    60
gauacgauag aaaauguaaa ggccaagauc caggauaagg aaggaauucc uccugaucag   120
cagagacugg ccuuugcugg caaaucgcug gaagauggac guacuuuguc ugacuacaau   180
auucuaaagg acucuaaacu ucauccucug uugagacuuc gu                    222
```

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26

```
gcattgaagt ctcatggaag c                                            21
```

<210> SEQ ID NO 27
<211> LENGTH: 18
<212> TYPE: DNA

```
<213> ORGANISM: Artificial Sequence
<220> FEATURE:
<223> OTHER INFORMATION: primer

<400> SEQUENCE: 27
tcactgccat ggaggagc                                                 18

<210> SEQ ID NO 28
<211> LENGTH: 17
<212> TYPE: DNA
<213> ORGANISM: Artificial Sequence
<220> FEATURE:
<223> OTHER INFORMATION: primer

<400> SEQUENCE: 28
ccagcaccaa caagagc                                                  17

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
ggatgcctgg tactgtttgg                                               20

<210> SEQ ID NO 30
<211> LENGTH: 28
<212> TYPE: DNA
<213> ORGANISM: Artificial Sequence
<220> FEATURE:
<223> OTHER INFORMATION: primer

<400> SEQUENCE: 30
tctcaaagta tttcattttc ttggtgcc                                      28

<210> SEQ ID NO 31
<211> LENGTH: 24
<212> TYPE: DNA
<213> ORGANISM: Artificial Sequence
<220> FEATURE:
<223> OTHER INFORMATION: primer

<400> SEQUENCE: 31
tgagcaagga tcataaaatg ttgg                                          24

<210> SEQ ID NO 32
<211> LENGTH: 20
<212> TYPE: DNA
<213> ORGANISM: Artificial Sequence
<220> FEATURE:
<223> OTHER INFORMATION: sgRNA targeting sequence

<400> SEQUENCE: 32
cagaatgcaa gaagcccaga                                               20

<210> SEQ ID NO 33
<211> LENGTH: 20
<212> TYPE: DNA
<213> ORGANISM: Artificial Sequence
<220> FEATURE:
<223> OTHER INFORMATION: sgRNA targeting sequence

<400> SEQUENCE: 33
aagggtagct gttagaaggc                                               20
```

<210> SEQ ID NO 34
<211> LENGTH: 20
<212> TYPE: DNA
<213> ORGANISM: Artificial Sequence
<220> FEATURE:
<223> OTHER INFORMATION: sgRNA targeting sequence

<400> SEQUENCE: 34
tccaatcctg aacaaacagc                                               20

<210> SEQ ID NO 35
<211> LENGTH: 20
<212> TYPE: DNA
<213> ORGANISM: Artificial Sequence
<220> FEATURE:
<223> OTHER INFORMATION: RNP Reagent

<400> SEQUENCE: 35
atggcgtgca gtgcttcagc                                               20

<210> SEQ ID NO 36
<211> LENGTH: 127
<212> TYPE: DNA
<213> ORGANISM: Artificial Sequence
<220> FEATURE:
<223> OTHER INFORMATION: RNP Reagent

<400> SEQUENCE: 36
gccacctacg gcaagctgac cctgaagttc atctgcacca ccggcaagct gcccgtgccc    60
tggcccaccc tcgtgaccac cctgacgtac ggcgtgcagt gcttcagccg ctaccccgac   120
cacatga                                                            127

<210> SEQ ID NO 37
<211> LENGTH: 127
<212> TYPE: DNA
<213> ORGANISM: Artificial Sequence
<220> FEATURE:
<223> OTHER INFORMATION: RNP Reagent

<400> SEQUENCE: 37
agtggccaga gtccagcttg ggcccacgca ggggcctggc cagcagcaag cagcactctg    60
ccctcgtggg tttgtggttg cccacacatg tcattggagg tgacatcgat gtcctcccca   120
ttggcct                                                            127

<210> SEQ ID NO 38
<211> LENGTH: 20
<212> TYPE: DNA
<213> ORGANISM: Artificial Sequence
<220> FEATURE:
<223> OTHER INFORMATION: RNP Reagent

<400> SEQUENCE: 38
tgacatcaat tattatacat                                               20

<210> SEQ ID NO 39
<211> LENGTH: 182
<212> TYPE: DNA
<213> ORGANISM: Artificial Sequence
<220> FEATURE:
<223> OTHER INFORMATION: RNP Reagent

<400> SEQUENCE: 39

```
acaaaaccaa agatgaacac cagtgagtag agcggaggca ggaggcgggc tgcgatttgc    60
ttcacattga ttttttggca gggctcacat gtataataat tgatgtcata gattggactt   120
gacacttgat aatccatctt gttccaccct gtgcataaat aaaaagtgat cttttataaa   180
gt                                                                  182

<210> SEQ ID NO 40
<211> LENGTH: 182
<212> TYPE: DNA
<213> ORGANISM: Artificial Sequence
<220> FEATURE:
<223> OTHER INFORMATION: RNP Reagent

<400> SEQUENCE: 40
atggattggt catcctggtc atgggttacc agaagaaact gagaagcatg acggacaagt    60
acaggctgca cctgtcagtg gccgacatgt tctttgtcat cacgcttccc ttctgggcag   120
ttgatgccgt ggcaaactgg tactttggga acttcctatg caaggcagtc catgtcatct   180
ac                                                                  182

<210> SEQ ID NO 41
<211> LENGTH: 20
<212> TYPE: DNA
<213> ORGANISM: Artificial Sequence
<220> FEATURE:
<223> OTHER INFORMATION: RNP Reagent

<400> SEQUENCE: 41
gaagcgtgat gacaaagagg                                                20

<210> SEQ ID NO 42
<211> LENGTH: 182
<212> TYPE: DNA
<213> ORGANISM: Artificial Sequence
<220> FEATURE:
<223> OTHER INFORMATION: RNP Reagent

<400> SEQUENCE: 42
atggattggt catcctggtc atgggttacc agaagaaact gagaagcatg acggacaagt    60
acaggctgca cctgtcagtg gccgacatgt tctttgtcat cacgcttccc ttctgggcag   120
ttgatgccgt ggcaaactgg tactttggga acttcctatg caaggcagtc catgtcatct   180
ac                                                                  182

<210> SEQ ID NO 43
<211> LENGTH: 182
<212> TYPE: DNA
<213> ORGANISM: Artificial Sequence
<220> FEATURE:
<223> OTHER INFORMATION: RNP Reagent

<400> SEQUENCE: 43
acaaaaccaa agatgaacac cagtgagtag agcggaggca ggaggcgggc tgcgatttgc    60
ttcacattga ttttttggca gggctcacat gtataataat tgatgtcata gattggactt   120
gacacttgat aatccatctt gttccaccct gtgcataaat aaaaagtgat cttttataaa   180
gt                                                                  182

<210> SEQ ID NO 44
<211> LENGTH: 20
<212> TYPE: DNA
<213> ORGANISM: Artificial Sequence
```

<220> FEATURE:
<223> OTHER INFORMATION: primer

<400> SEQUENCE: 44
ctccatggtg ctatagagca                                               20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
gccctgtcaa gagttgacac                                               20

<210> SEQ ID NO 46
<211> LENGTH: 32
<212> TYPE: DNA
<213> ORGANISM: Artificial Sequence
<220> FEATURE:
<223> OTHER INFORMATION: primer

<400> SEQUENCE: 46
agaggagtta gccaagatgt gactttgaaa cc                                 32

<210> SEQ ID NO 47
<211> LENGTH: 33
<212> TYPE: DNA
<213> ORGANISM: Artificial Sequence
<220> FEATURE:
<223> OTHER INFORMATION: primer

<400> SEQUENCE: 47
ggacaggatg acaataccag gcaggataag gcc                                33

<210> SEQ ID NO 48
<211> LENGTH: 76
<212> TYPE: PRT
<213> ORGANISM: Artificial Sequence
<220> FEATURE:
<223> OTHER INFORMATION: constructed seqeuence
<220> FEATURE:
<221> NAME/KEY: MISC_FEATURE
<222> LOCATION: (2)..(2)
<223> OTHER INFORMATION: Xaa2 is Gln, Leu, or Arg
<220> FEATURE:
<221> NAME/KEY: MISC_FEATURE
<222> LOCATION: (4)..(4)
<223> OTHER INFORMATION: Xaa4 is Phe, Tyr or Ile
<220> FEATURE:
<221> NAME/KEY: MISC_FEATURE
<222> LOCATION: (6)..(6)
<223> OTHER INFORMATION: Xaa6 is Lys or Thr
<220> FEATURE:
<221> NAME/KEY: MISC_FEATURE
<222> LOCATION: (8)..(8)
<223> OTHER INFORMATION: Xaa8 is Leu, Phe or Asp
<220> FEATURE:
<221> NAME/KEY: MISC_FEATURE
<222> LOCATION: (9)..(9)
<223> OTHER INFORMATION: Xaa9 is Thr, Ala or Met
<220> FEATURE:
<221> NAME/KEY: MISC_FEATURE
<222> LOCATION: (10)..(10)
<223> OTHER INFORMATION: Xaa10 is Gly, Arg or Trp
<220> FEATURE:
<221> NAME/KEY: MISC_FEATURE
<222> LOCATION: (11)..(11)
<223> OTHER INFORMATION: Xaa11 is Lys or Met
<220> FEATURE:

```
<221> NAME/KEY: MISC_FEATURE
<222> LOCATION: (12)..(12)
<223> OTHER INFORMATION: Xaa12 is Thr, Pro or Arg
<220> FEATURE:
<221> NAME/KEY: MISC_FEATURE
<222> LOCATION: (14)..(14)
<223> OTHER INFORMATION: Xaa14 is Thr or Ser
<220> FEATURE:
<221> NAME/KEY: MISC_FEATURE
<222> LOCATION: (44)..(44)
<223> OTHER INFORMATION: Xaa44 is Ile, Ala or Tyr
<220> FEATURE:
<221> NAME/KEY: MISC_FEATURE
<222> LOCATION: (46)..(46)
<223> OTHER INFORMATION: Xaa46 is Ala or Gly
<220> FEATURE:
<221> NAME/KEY: MISC_FEATURE
<222> LOCATION: (47)..(47)
<223> OTHER INFORMATION: Xaa47 is Gly, Glu, Asp or Ala
<220> FEATURE:
<221> NAME/KEY: MISC_FEATURE
<222> LOCATION: (48)..(48)
<223> OTHER INFORMATION: Xaa48 is Lys, Met or Ser
<220> FEATURE:
<221> NAME/KEY: MISC_FEATURE
<222> LOCATION: (49)..(49)
<223> OTHER INFORMATION: Xaa49 is Gln, Arg, Asp or Ser
<220> FEATURE:
<221> NAME/KEY: MISC_FEATURE
<222> LOCATION: (62)..(62)
<223> OTHER INFORMATION: Xaa62 is Gln, Lys, or Leu
<220> FEATURE:
<221> NAME/KEY: MISC_FEATURE
<222> LOCATION: (63)..(63)
<223> OTHER INFORMATION: Xaa63 is Lys or Asn
<220> FEATURE:
<221> NAME/KEY: MISC_FEATURE
<222> LOCATION: (64)..(64)
<223> OTHER INFORMATION: Xaa64 is Glu or Asp
<220> FEATURE:
<221> NAME/KEY: MISC_FEATURE
<222> LOCATION: (66)..(66)
<223> OTHER INFORMATION: Xaa66 is Thr, Ser or Lys
<220> FEATURE:
<221> NAME/KEY: MISC_FEATURE
<222> LOCATION: (67)..(67)
<223> OTHER INFORMATION: Xaa67 is Leu or Lys
<220> FEATURE:
<221> NAME/KEY: MISC_FEATURE
<222> LOCATION: (68)..(68)
<223> OTHER INFORMATION: Xaa68 is His, Phe, Asn, or Leu
<220> FEATURE:
<221> NAME/KEY: MISC_FEATURE
<222> LOCATION: (69)..(69)
<223> OTHER INFORMATION: Xaa69 is Leu or Pro
<220> FEATURE:
<221> NAME/KEY: MISC_FEATURE
<222> LOCATION: (70)..(70)
<223> OTHER INFORMATION: Xaa70 is Val or Leu
<220> FEATURE:
<221> NAME/KEY: MISC_FEATURE
<222> LOCATION: (71)..(71)
<223> OTHER INFORMATION: Xaa71 is Leu or Val
<220> FEATURE:
<221> NAME/KEY: MISC_FEATURE
<222> LOCATION: (72)..(72)
<223> OTHER INFORMATION: Xaa72 is Arg, Lys or Asn
<220> FEATURE:
<221> NAME/KEY: MISC_FEATURE
<222> LOCATION: (73)..(73)
<223> OTHER INFORMATION: Xaa73 is Leu or Asn
<220> FEATURE:
<221> NAME/KEY: MISC_FEATURE
<222> LOCATION: (74)..(74)
<223> OTHER INFORMATION: Xaa74 is Arg, Ser or Leu
<220> FEATURE:
<221> NAME/KEY: MISC_FEATURE
<222> LOCATION: (75)..(75)
<223> OTHER INFORMATION: Xaa75 is Gly, Val or Arg or is absent
```

```
<220> FEATURE:
<221> NAME/KEY: MISC_FEATURE
<222> LOCATION: (76)..(76)
<223> OTHER INFORMATION: Xaa76 is Gly, Thr or Val or is absent

<400> SEQUENCE: 48

Met Xaa Ile Xaa Val Xaa Thr Xaa Xaa Xaa Xaa Xaa Ile Xaa Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Xaa Phe Xaa Xaa Xaa
        35                  40                  45

Xaa Leu Glu Asp Gly Arg Thr Leu Ser Asp Tyr Asn Ile Xaa Xaa Xaa
50                  55                  60

Ser Xaa Xaa Xaa Xaa Xaa Xaa Xaa Xaa Xaa Xaa
65                  70                  75

<210> SEQ ID NO 49
<211> LENGTH: 228
<212> TYPE: RNA
<213> ORGANISM: Artificial Sequence
<220> FEATURE:
<223> OTHER INFORMATION: constructed sequence

<400> SEQUENCE: 49
auguugauuu ucgugaaaac ccuuaccggg aaaaccauca cccucgaggu ugaacccucg     60
gauacgauag aaaauguaaa ggccaagauc caggauaagg aaggaauucc uccugaucag    120
cagagacuga ucuuugcugg caaaucgcug gaagauggac guacuuuguc ugacuacaau    180
auucuaaagg acucuaaacu ucaucuagug uugagacuuc gugguggu                 228

<210> SEQ ID NO 50
<211> LENGTH: 222
<212> TYPE: RNA
<213> ORGANISM: Artificial Sequence
<220> FEATURE:
<223> OTHER INFORMATION: constructed sequence

<400> SEQUENCE: 50
auguugauuu ucgugaaaac ccuuaccggg aaaaccauca cccucgaggu ugaacccucg     60
gauacgauag aaaauguaaa ggccaagauc caggauaagg aaggaauucc uccugaucag    120
cagagacugg ccuuugcugg caaaucgcug gaagauggac guacuuuguc ugacuacaau    180
auucuaaagg acucuaaacu ucaucuagug uugagacuuc gu                       222

<210> SEQ ID NO 51
<211> LENGTH: 75
<212> TYPE: PRT
<213> ORGANISM: Artificial Sequence
<220> FEATURE:
<223> OTHER INFORMATION: UbvG08

<400> SEQUENCE: 51

Met Leu Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45
```

```
Ser Leu Glu Asp Gly Arg Thr Leu Ser Asp Tyr Asn Ile Leu Lys Asp
 50                  55                  60
Ser Lys Leu His Pro Leu Leu Arg Leu Arg Gly
 65                  70                  75
```